US012605155B2

(12) United States Patent
Gettinger et al.

(10) Patent No.: US 12,605,155 B2
(45) Date of Patent: *Apr. 21, 2026

(54) JAW OPENING FEATURE FOR SURGICAL STAPLER

(71) Applicant: Cilag GmbH International, Zug (CH)

(72) Inventors: Rebecca J. Gettinger, Loveland, OH (US); Katherine J. Schmid, Loveland, OH (US); Charles J. Scheib, Loveland, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/733,005

(22) Filed: Jun. 4, 2024

(65) Prior Publication Data

US 2024/0325020 A1 Oct. 3, 2024

Related U.S. Application Data

(63) Continuation of application No. 17/697,062, filed on Mar. 17, 2022, now Pat. No. 12,029,417, which is a
(Continued)

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 17/105* (2013.01);
(Continued)

(58) Field of Classification Search
CPC ............ A61B 17/105; A61B 17/07207; A61B 17/068; A61B 2017/2933;
(Continued)

(56) References Cited

U.S. PATENT DOCUMENTS

| 4,805,823 A | 2/1989 | Rothfuss |
| 5,415,334 A | 5/1995 | Williamson et al. |
| (Continued) | | |

FOREIGN PATENT DOCUMENTS

| CN | 1732859 A | 2/2006 |
| CN | 101507634 A | 8/2009 |
| (Continued) | | |

OTHER PUBLICATIONS

Chinese Office Action, The First Office Action, and First Search Report dated Sep. 27, 2018 for Application No. 201580034423.8, 13 pages.

(Continued)

*Primary Examiner* — Thomas M Wittenschlaeger
(74) *Attorney, Agent, or Firm* — FBT Gibbons LLP

(57) ABSTRACT

An end effector for use with a surgical instrument includes a lower jaw, an anvil, and a resilient member. The anvil is pivotable relative to the lower jaw between a fully opened position and a fully closed position. The resilient member is configured to bias the anvil to remain in the fully opened position when the anvil is in the fully opened position. The end effector may include a closure ring coupled with the anvil that is translatable relative to the lower jaw and configured to engage the anvil at an interface as the closure ring translates proximally relative to the lower jaw to thereby pivot the anvil relative to the lower jaw toward the fully opened position. In various embodiments, the resilient member may comprise elastomeric material positioned between the closure ring and the anvil or a pair of springs or resilient arms that engage the anvil.

20 Claims, 60 Drawing Sheets

Related U.S. Application Data continuation of application No. 16/562,887, filed on Sep. 6, 2019, now Pat. No. 11,304,694, which is a continuation of application No. 14/314,164, filed on Jun. 25, 2014, now Pat. No. 10,456,132.

(51) Int. Cl.
  *A61B 17/10* (2006.01)
  *A61B 17/00* (2006.01)
  *A61B 17/29* (2006.01)

(52) U.S. Cl.
  CPC .............. *A61B 2017/00862* (2013.01); *A61B 2017/07214* (2013.01); *A61B 2017/07257* (2013.01); *A61B 2017/2933* (2013.01); *A61B 2017/294* (2013.01)

(58) Field of Classification Search
  CPC .... A61B 2017/294; A61B 2017/07257; A61B 2017/00862; A61B 2017/07214
  See application file for complete search history.

(56) References Cited

U.S. PATENT DOCUMENTS

| | | | |
|---|---|---|---|
| 5,465,895 A | 11/1995 | Knodel et al. | |
| 5,476,206 A | 12/1995 | Green et al. | |
| 5,507,426 A * | 4/1996 | Young .............. | A61B 17/07207 |
| | | | 227/181.1 |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,762,256 A | 6/1998 | Mastri et al. | |
| 5,792,135 A | 8/1998 | Madhani et al. | |
| 5,814,055 A | 9/1998 | Knodel et al. | |
| 5,817,084 A | 10/1998 | Jensen | |
| 5,820,009 A | 10/1998 | Melling et al. | |
| 5,878,193 A | 3/1999 | Wang et al. | |
| 5,894,979 A | 4/1999 | Powell | |
| 5,918,791 A | 7/1999 | Sorrentino | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,128,253 B2 | 10/2006 | Mastri et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,631,793 B2 | 12/2009 | Rethy et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 7,922,742 B2 | 4/2011 | Hillstead et al. | |
| 7,980,443 B2 | 7/2011 | Scheib et al. | |
| 8,015,976 B2 | 9/2011 | Shah | |

| | | | |
|---|---|---|---|
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,479,969 B2 | 7/2013 | Shelton | |
| 8,573,461 B2 | 11/2013 | Shelton et al. | |
| 8,573,465 B2 | 11/2013 | Shelton | |
| 8,602,288 B2 | 12/2013 | Shelton et al. | |
| 8,616,431 B2 | 12/2013 | Timm et al. | |
| 8,632,535 B2 | 1/2014 | Shelton, IV et al. | |
| 8,701,960 B1 | 4/2014 | Manoux et al. | |
| 8,783,541 B2 | 7/2014 | Shelton et al. | |
| 8,800,838 B2 | 8/2014 | Shelton | |
| 8,820,605 B2 | 9/2014 | Shelton | |
| 8,833,632 B2 | 9/2014 | Swensgard | |
| 8,844,789 B2 | 9/2014 | Shelton et al. | |
| 9,078,653 B2 | 7/2015 | Leimbach et al. | |
| 9,101,358 B2 | 8/2015 | Kerr et al. | |
| 9,186,142 B2 | 11/2015 | Fanelli et al. | |
| 9,301,759 B2 | 4/2016 | Spivey et al. | |
| 9,433,419 B2 | 9/2016 | Gonzalez et al. | |
| 9,492,146 B2 | 11/2016 | Kostrzewski et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,720,076 B2 | 8/2017 | Guo et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,867,615 B2 | 1/2018 | Fanelli et al. | |
| 10,064,620 B2 | 9/2018 | Gettinger et al. | |
| 10,092,292 B2 | 10/2018 | Boudreaux et al. | |
| 10,123,798 B2 | 11/2018 | Baxter, III et al. | |
| 10,292,701 B2 | 5/2019 | Scheib et al. | |
| 10,335,147 B2 | 7/2019 | Rector et al. | |
| 10,456,132 B2 | 10/2019 | Gettinger et al. | |
| 11,304,694 B2 | 4/2022 | Gettinger et al. | |
| 12,029,417 B2 | 7/2024 | Gettinger et al. | |
| 2005/0023324 A1 * | 2/2005 | Doll ................ | A61B 17/07207 |
| | | | 227/175.2 |
| 2007/0175950 A1 | 8/2007 | Shelton et al. | |
| 2012/0080336 A1 | 4/2012 | Shelton, IV et al. | |

FOREIGN PATENT DOCUMENTS

| | | |
|---|---|---|
| EP | 2005896 A2 | 12/2008 |
| JP | H09-164144 A | 6/1997 |
| JP | 2002-085415 A | 3/2002 |
| JP | 2014-028144 A | 2/2014 |
| WO | 2008/118728 A1 | 10/2008 |

OTHER PUBLICATIONS

Chinese Office Action dated Jun. 3, 2019 for Application No. 201580034423.8, 7 pages.

European Search Report and Written Opinion dated Jan. 20, 2016 for Application No. 15173532.1, 8 pages.

European Search Report, Partial, and Written Opinion dated Jun. 18, 2019 for Application No. 18214493.1, 10 pages.

International Search Report and Written Opinion dated Aug. 19, 2015 for International Application No. PCT/US2015/033109, 9 pages.

Japanese Office Action, Notification of Reasons for Refusal, dated Mar. 19, 2019 for Application No. 2016-574925, 5 pages.

* cited by examiner

265

266

260

754

766

702a

704a

740

760

750

800a

840

860

850

JAW OPENING FEATURE FOR SURGICAL STAPLER

PRIORITY

This application is a continuation of U.S. patent application Ser. No. 17/697,062, entitled "Jaw Opening Feature for Surgical Stapler," filed Mar. 17, 2022, issued as U.S. Pat. No. 12,029,417, on Jul. 9, 2024, which is a continuation of U.S. patent application Ser. No. 16/562,887, entitled "Jaw Opening Feature for Surgical Stapler," filed Sep. 6, 2019, issued as U.S. Pat. No. 11,304,694 on Apr. 19, 2022, which is a continuation of U.S. patent application Ser. No. 14/314, 164, entitled "Jaw Opening Feature for Surgical Stapler," filed Jun. 25, 2014, issued as U.S. Pat. No. 10,456,132 on Oct. 29, 2019, the disclosures of which are incorporated by reference herein in their entireties.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely illustrative surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380, 695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. patent application Ser. No. 13/780,067, entitled "Surgical Instrument End Effector Articulation Drive with Pinion and Opposing Racks," filed Feb. 28, 2013, issued as U.S. Pat. No. 9,186,142 on Nov. 17, 2015; U.S. patent application Ser. No. 13/780,082, entitled "Lockout Feature for Movable Cutting Member of Surgical Instrument," filed Feb. 28, 2013, issued as U.S. Pat. No. 9,717,497 on Aug. 1, 2017; U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016; U.S. patent application Ser. No. 13/780,120, entitled "Jaw Closure Feature for End Effector of Surgical Instrument," filed Feb. 28, 2013, issued as U.S. Pat. No. 9,839,421 on Dec. 12, 2017; U.S. patent application Ser. No. 13/780,162, entitled "Surgical Instrument with Articulation Lock having a Detenting Binary Spring," filed Feb. 28, 2013, issued as U.S. Pat. No. 9,867,615 on Jan. 16, 2018; U.S. patent application Ser. No. 13/780,171, entitled "Distal Tip Features for End Effector of Surgical Instrument," filed Feb. 28, 2013, issued as U.S. Pat. No. 9,622,746 on Apr. 18, 2017; U.S. patent application Ser. No. 13/780, 379, entitled "Staple Forming Features for Surgical Stapling Instrument," filed Feb. 28, 2013, issued as U.S. Pat. No. 10,092,292 on Oct. 9, 2018; U.S. patent application Ser. No. 13/780,402, entitled "Surgical Instrument with Multi-Diameter Shaft," filed Feb. 28, 2013, issued as U.S. Pat. No. 9,795,379 on Oct. 24, 2017; and U.S. patent application Ser.

No. 13/780,417, entitled "Installation Features for Surgical Instrument End Effector Cartridge," filed Feb. 28, 2013, issued as U.S. Pat. No. 9,808,248 on Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
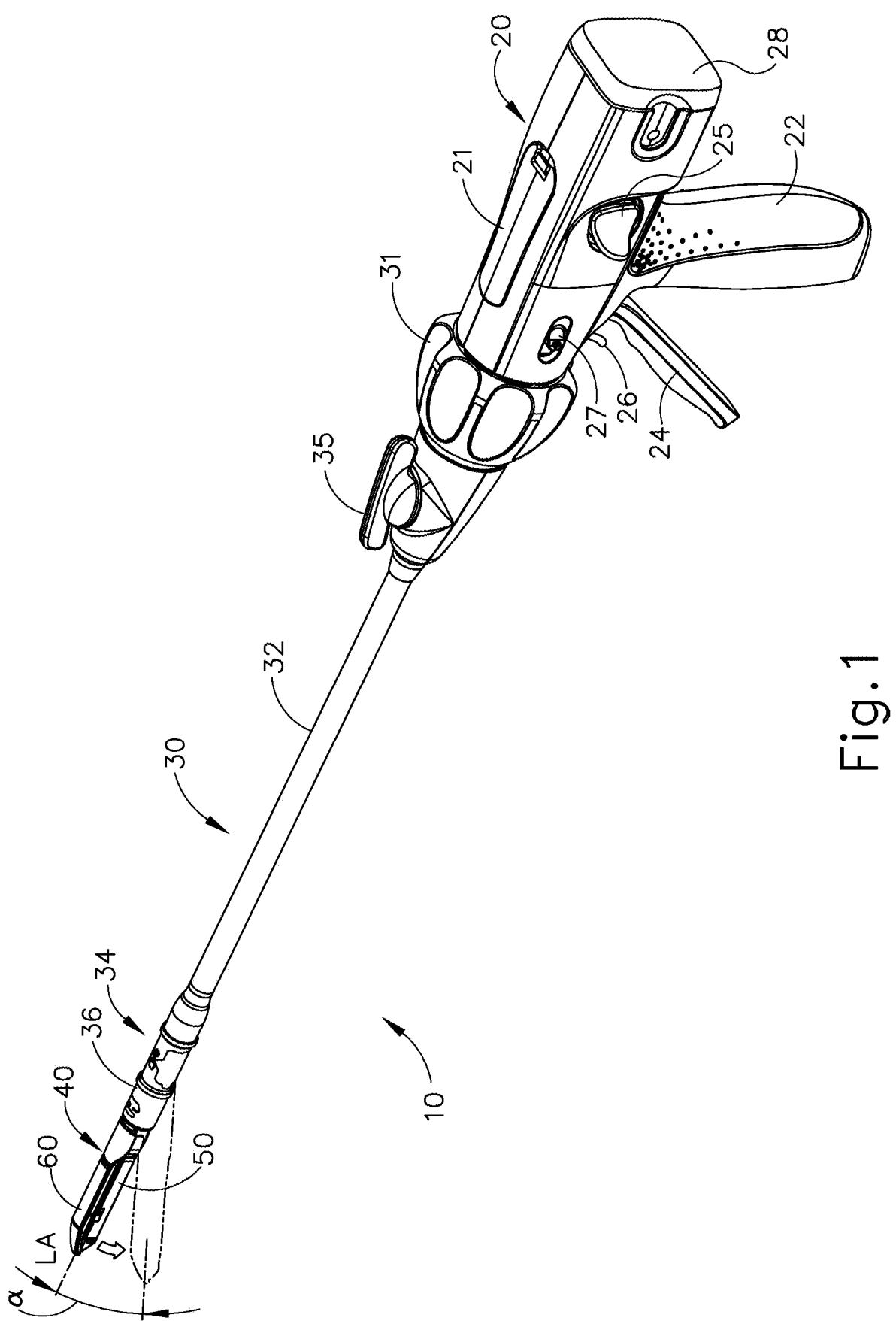
FIG. 1 depicts a perspective view of an illustrative articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Illustrative Surgical Stapler

FIG. 1 depicts an illustrative surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Illustrative Handle Assembly and Shaft Assembly

Figure 2:
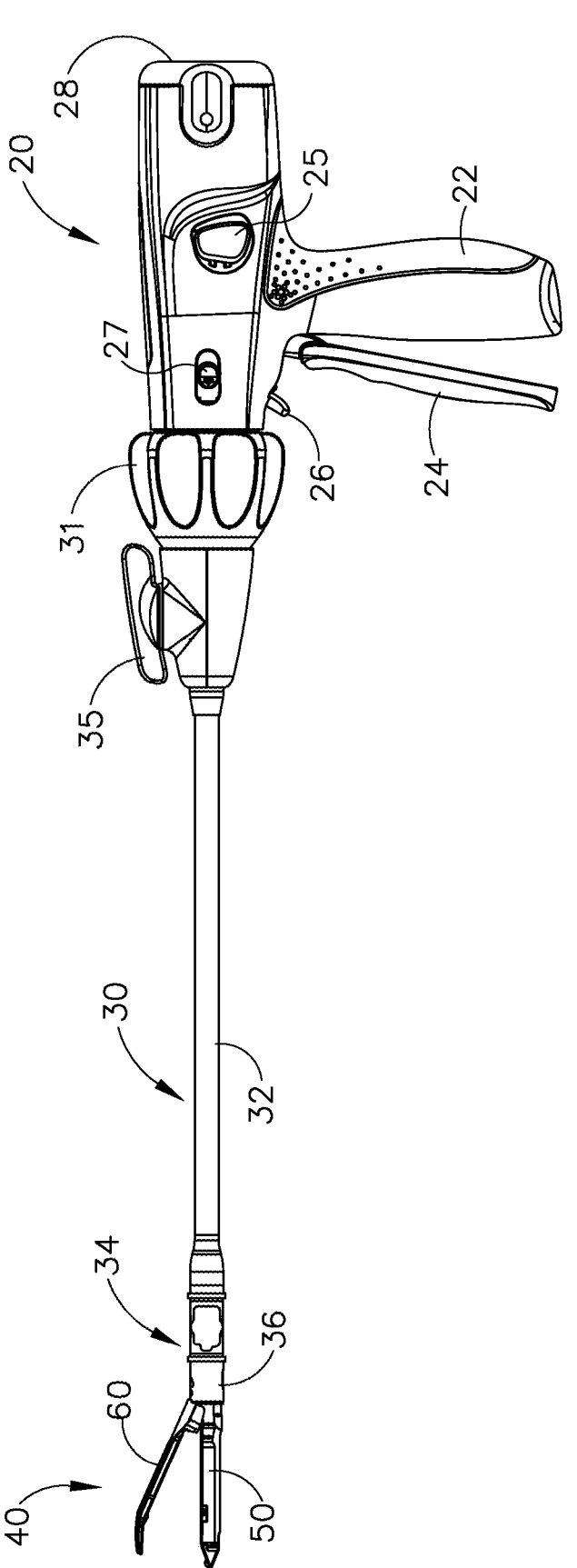
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein. Furthermore, it should be understood that handle assembly (20) is merely an illustrative type of body assembly that can be included within instrument (10) and instrument (10) may comprise any other suitable body assembly in addition to or instead of handle assembly (20), including but not limited to a body assembly configured to allow instrument (10) to be used during robotic-assisted medical treatments and procedures.

Figure 3:
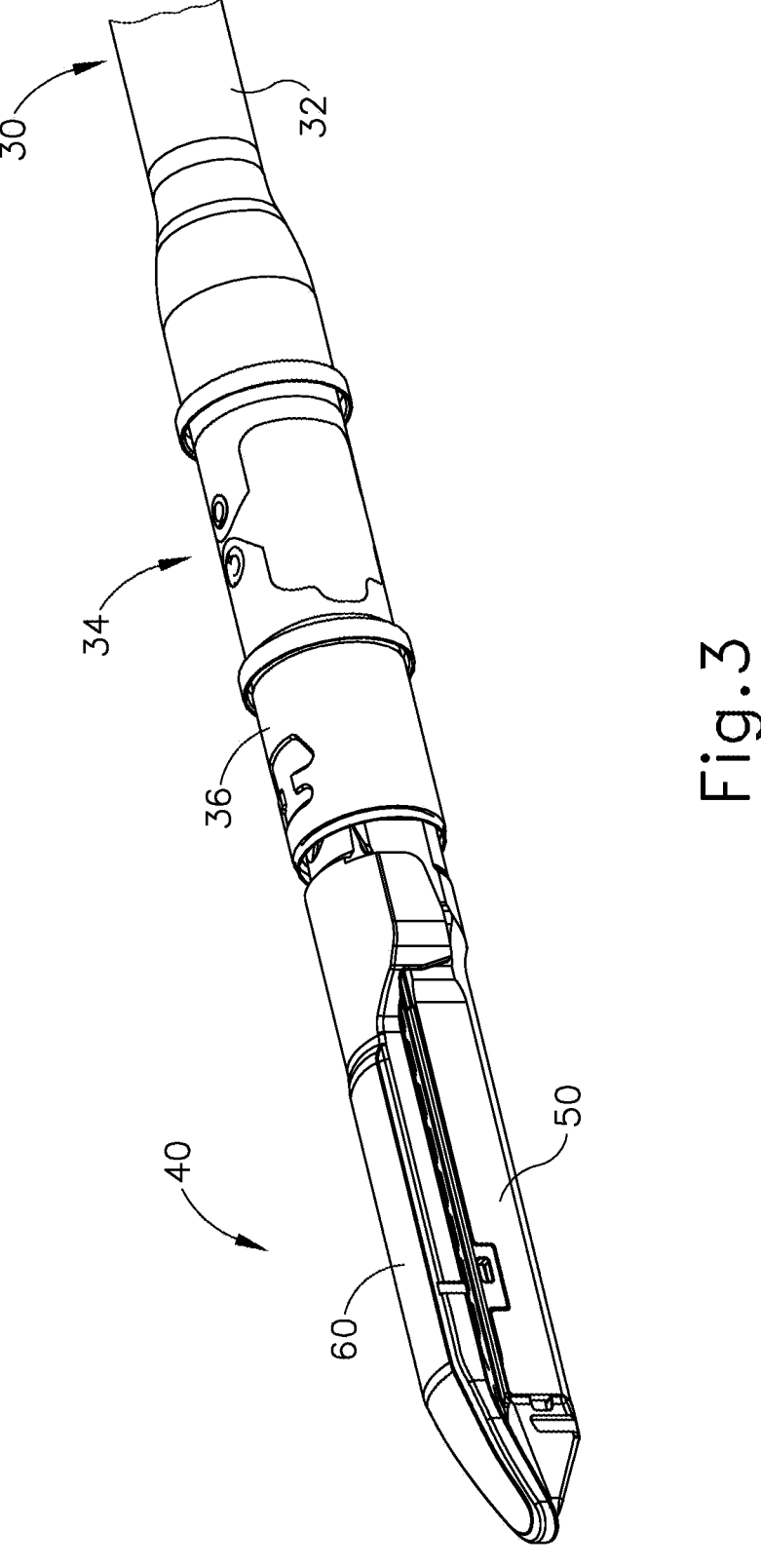
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Illustrative features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (a). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. patent application Ser. No. 13/780,067, entitled "Surgical Instrument End Effector Articulation Drive with Pinion and Opposing Racks," filed Feb. 28, 2013, issued as U.S. Pat. No. 9,186,142 on Nov. 17, 2015, the disclosure of which is incorporated by reference herein. Articulation section (34) may also be constructed and operable in accordance with at least some of the teachings of U.S. patent application Ser. No. 14/314,125, entitled "Articulation Drive Features for Surgical Stapler," filed Jun. 25, 2014, issued as U.S. Pat. No. 10,292,701 on May 21, 2019, the disclosure of which is incorporated by reference herein; and/or U.S. patent application Ser. No. 14/314,276, entitled "Method of Unlocking Articulation Joint in Surgical Stapler," filed Jun. 25, 2014, issued as U.S. Pat. No. 10,064,620 on Sep. 4, 2018, the disclosure of which is incorporated by reference herein. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. patent application Ser. No. 13/780,402, entitled "Surgical Instrument with Multi-Diameter Shaft," filed Feb. 28, 2013, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Illustrative End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. patent application Ser. No. 13/780,417, entitled "Installation Features for Surgical Instrument End Effector Cartridge," filed Feb. 28, 2013, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

Figure 4:
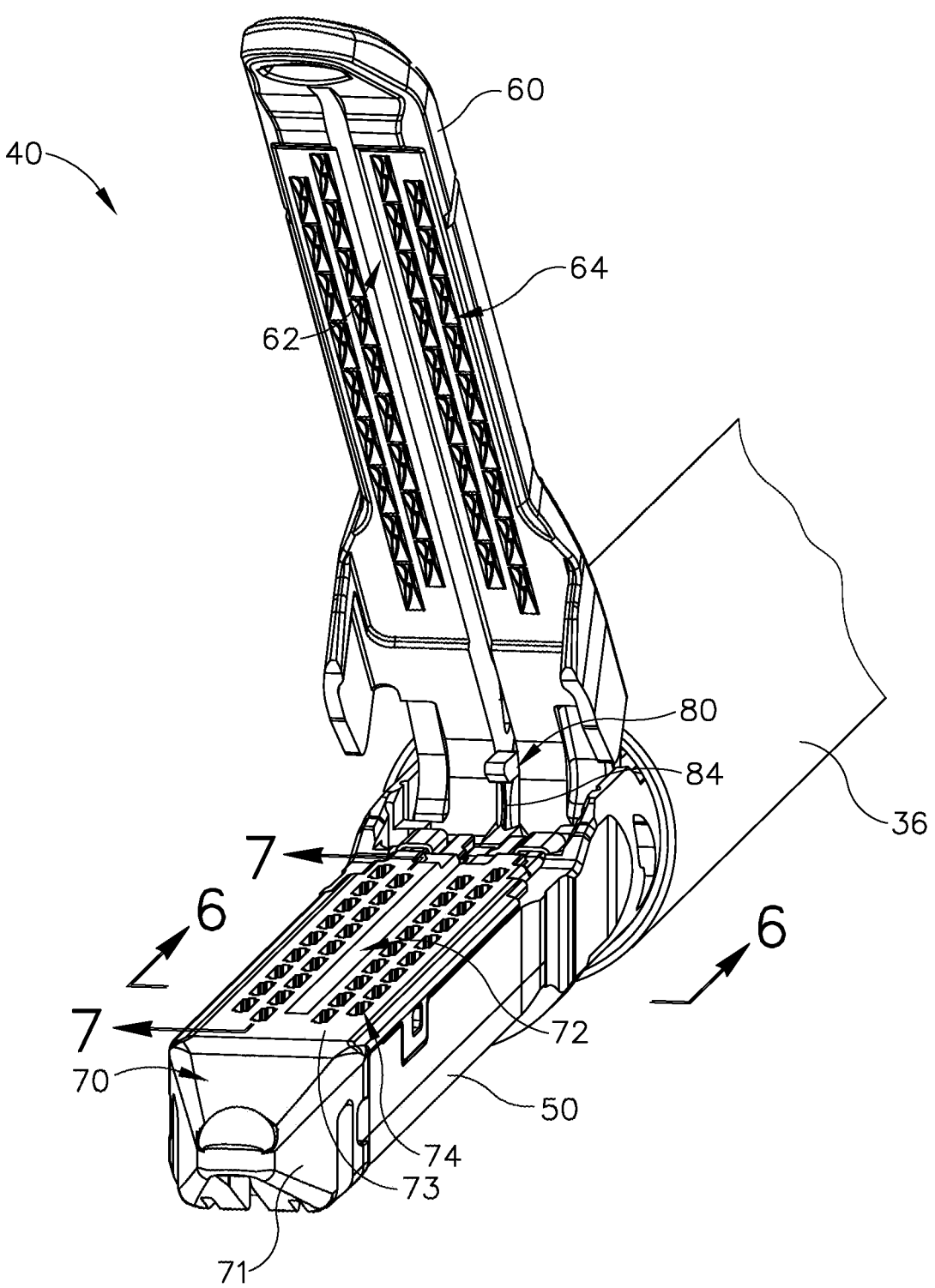
FIG. 4 depicts a perspective view of the end effector of FIG. 3, with the end effector in an open configuration.
Figure 5:
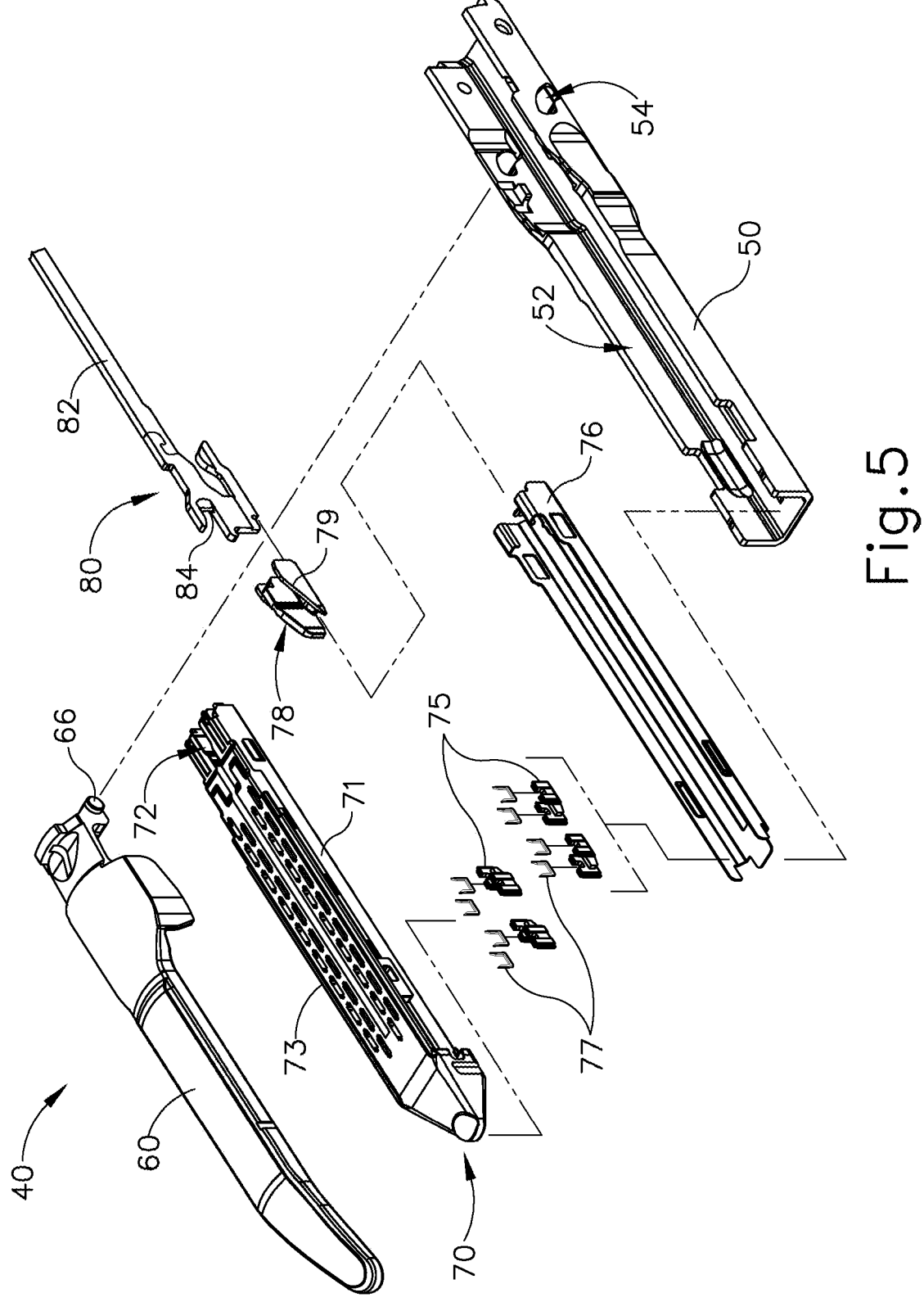
FIG. 5 depicts an exploded perspective view of the end effector of FIG. 3.
Figure 6:
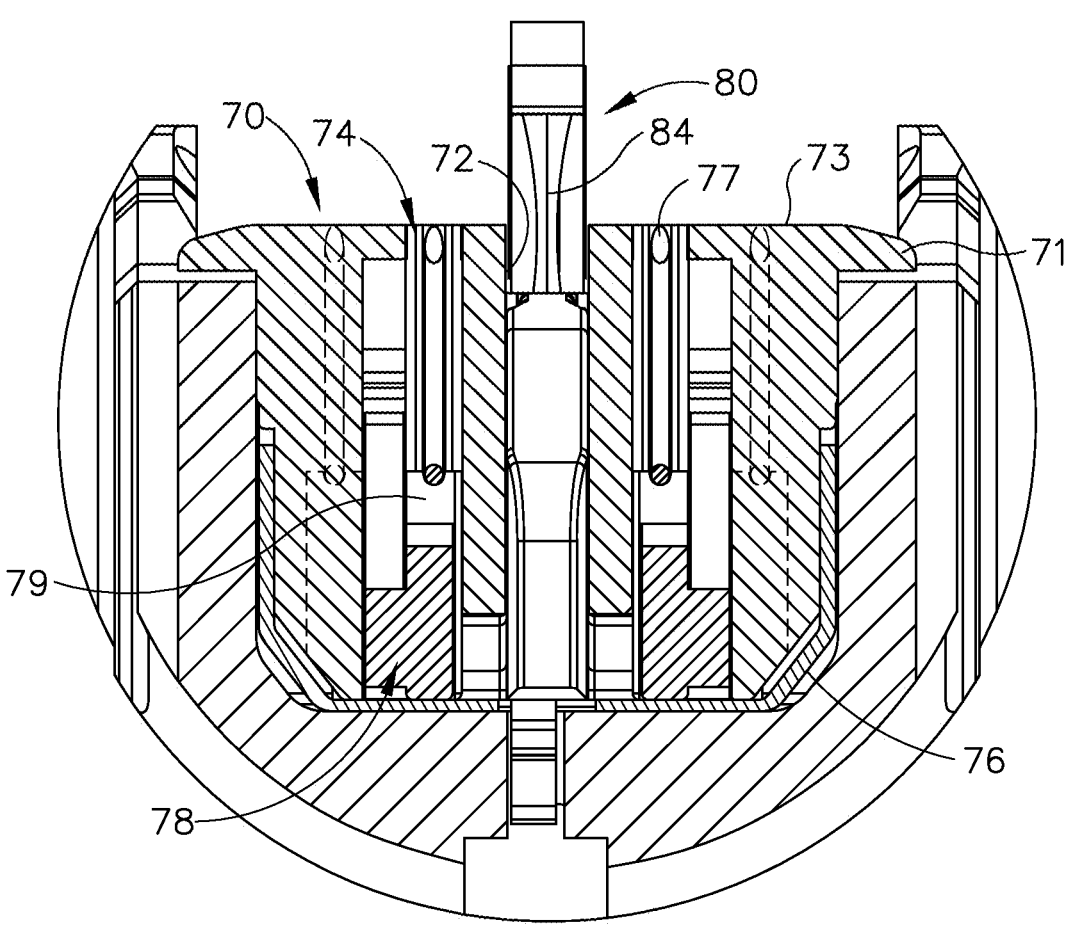
FIG. 6 depicts a cross-sectional end view of the end effector of FIG. 3, taken along line 6-6 of FIG. 4.
Figure 7A:
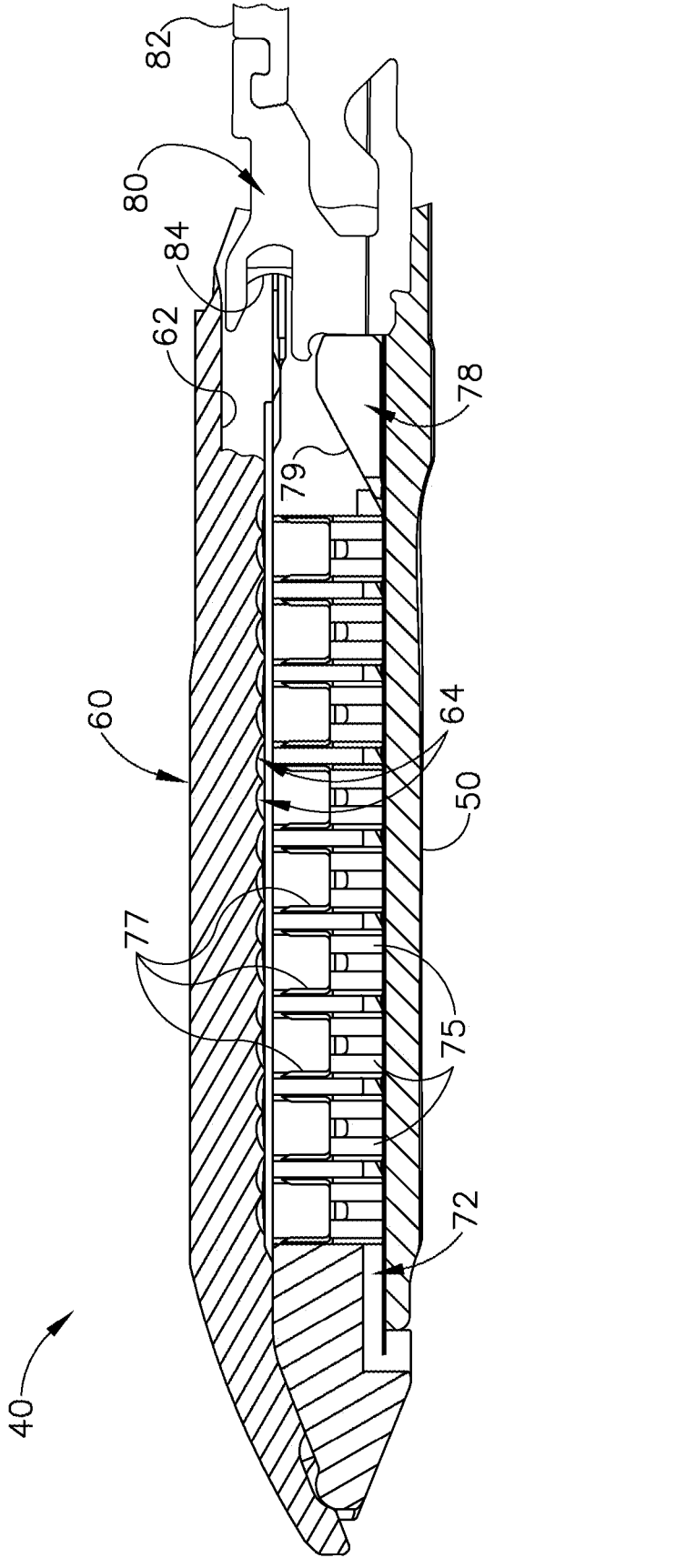
FIG. 7A depicts a cross-sectional side view of the end effector of FIG. 3, taken along line 7-7 of FIG. 4, with the firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U. U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. patent application Ser. No. 13/780,417, entitled "Installation Features for Surgical Instrument End Effector Cartridge," filed Feb. 28, 2013, issued as U.S. Pat. No. 9,808, 248 on Nov. 7, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016; at least some of the teachings of U.S. patent application Ser. No. 13/780,120, entitled "Jaw Closure Feature for End Effector of Surgical Instrument," filed Feb. 28, 2013, issued as U.S. Pat. No. 9,839,421 on Dec. 12, 2017; and/or at least some of the teachings of U.S. patent application Ser. No. 13/780,379, entitled "Staple Forming Features for Surgical Stapling Instrument," filed Feb. 28, 2013, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

Figure 7B:
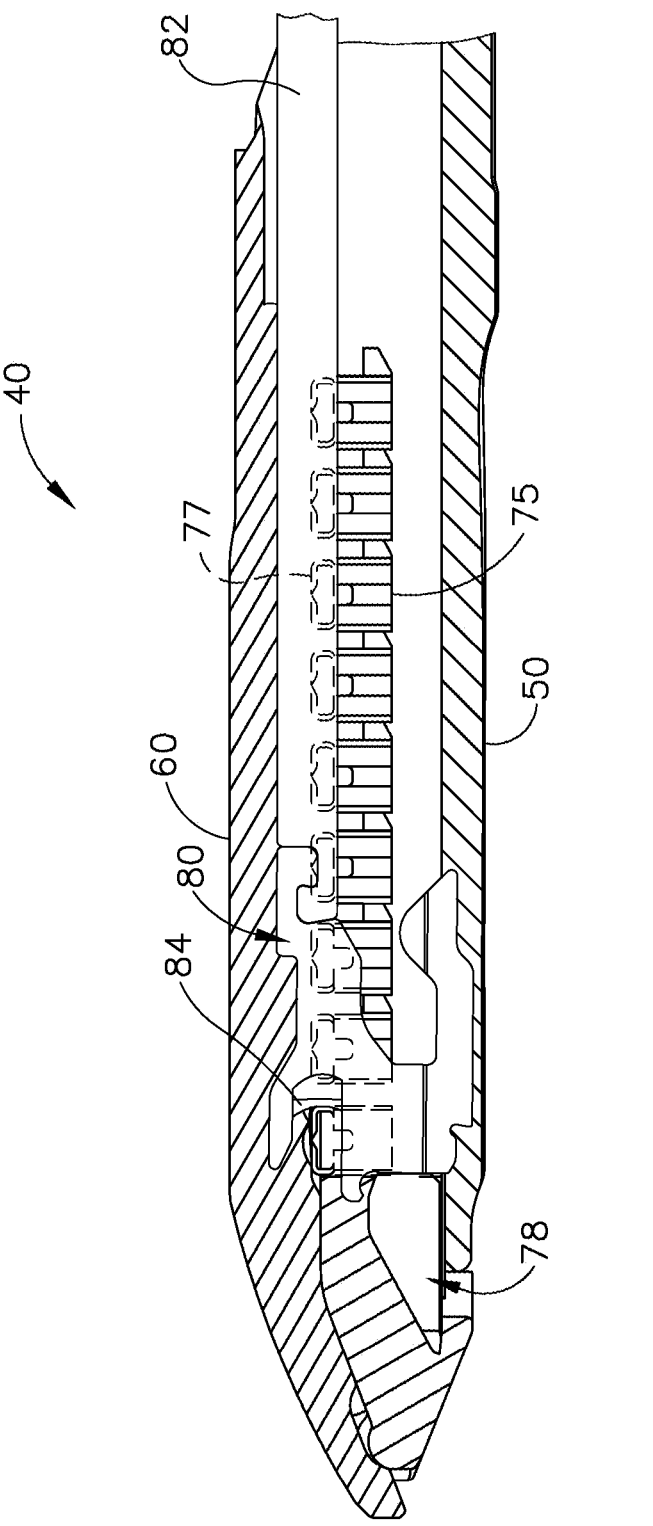
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80)

from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. patent application Ser. No. 13/780, 082, entitled "Lockout Feature for Movable Cutting Member of Surgical Instrument," filed Feb. 28, 2013, issued as U.S. Pat. No. 9,717,497 on Aug. 1, 2017, the disclosure of which is incorporated by reference herein; and/or at least some of the teachings of U.S. patent application Ser. No. 14/314,108, entitled "Method of Using Lockout Features for Surgical Stapler Cartridge," filed Jun. 25, 2014, issued as U.S. Pat. No. 10,335,147 on Jul. 2, 2019, the disclosure of which is incorporated by reference herein. Other suitable forms that lockout features may take will be apparent to those of ordinary skill in the art in view of the teachings herein. Alternatively, end effector (40) may simply omit such lockout features.

C. Illustrative Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. patent application Ser. No. 13/780,120, entitled "Jaw Closure Feature for End Effector of Surgical Instrument," filed Feb. 28, 2013, issued as U.S. Pat. No. 9,839,421 on Dec. 12, 2017, the disclosure of which is incorporated by reference herein; and/or in accordance with at least some of the teachings below. Illustrative features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Illustrative Actuation of Firing Beam

Figure 9:
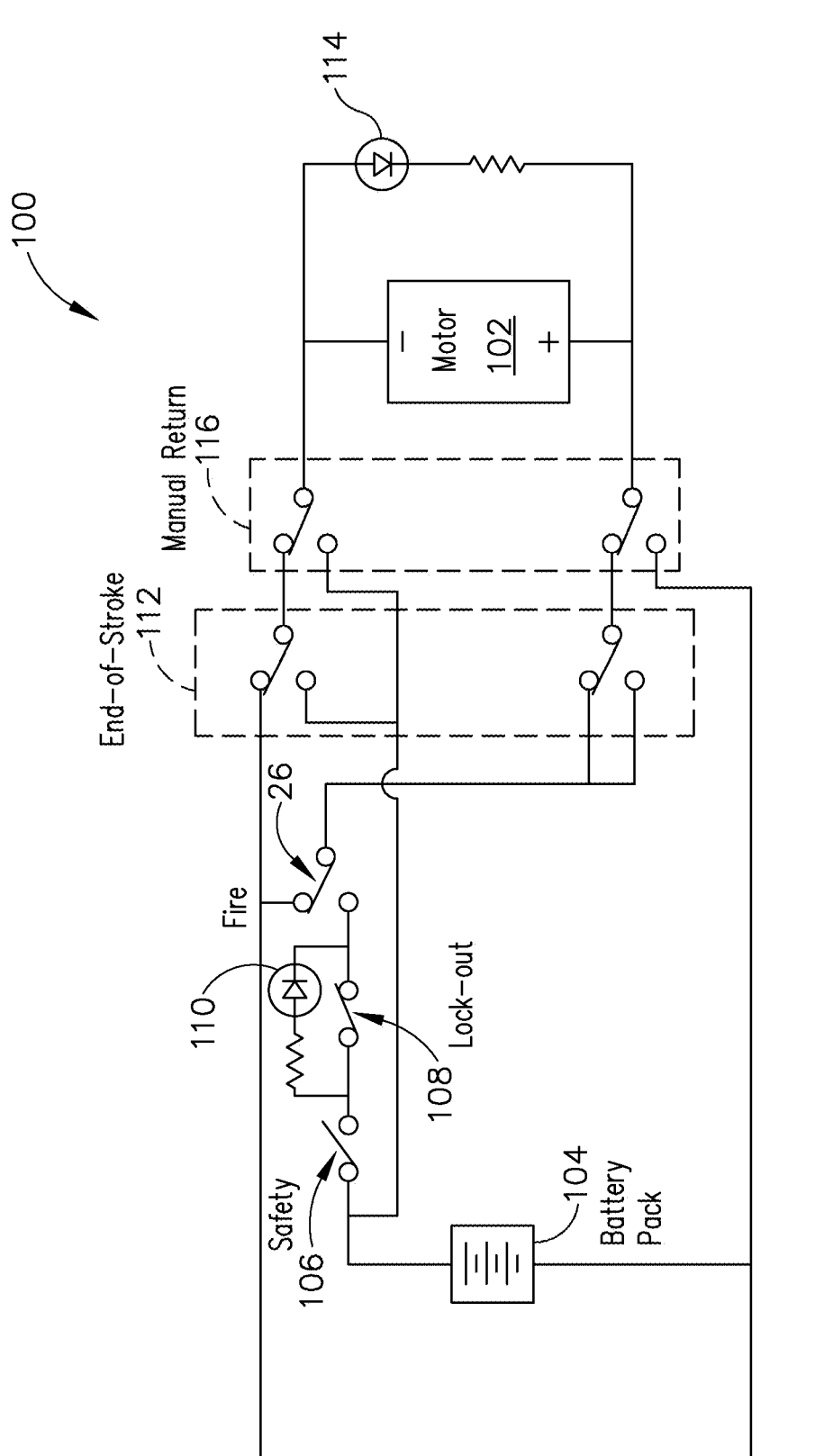
FIG. 9 depicts a schematic view of an illustrative control circuit for use in the instrument of FIG. 1.

In the present example, instrument (10) provides motorized control of firing beam (82). FIGS. 9-12 show illustrative components that may be used to provide motorized control of firing beam (82). In particular, FIG. 9 shows an illustrative control circuit (100) that may be used to power an electric motor (102) with electric power from a battery pack (28) (also shown in FIGS. 1-2). Electric motor (102) is operable to translate firing beam (82) longitudinally as will be described in greater detail below. It should be understood that the entire control circuit (100), including motor (102) and battery pack (28), may be housed within handle assembly (20). FIG. 9 shows firing trigger (26) as an open switch, though it should be understood that this switch is closed when firing trigger (26) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle assembly (20). Safety switch (106) may also provide a mechanical lockout of firing trigger (26), such that firing trigger (26) is mechanically blocked from actuation until safety switch (106) is actuated.

Circuit (100) of the present example also includes a lockout switch (108), which is configured to be closed by default but is automatically opened in response to a lockout condition. By way of example only, a lockout condition may include one or more of the following: the absence of a cartridge (70) in lower jaw (50), the presence of a spent (e.g., previously fired) cartridge (70) in lower jaw (50), an insufficiently closed anvil (60), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Figure 12:
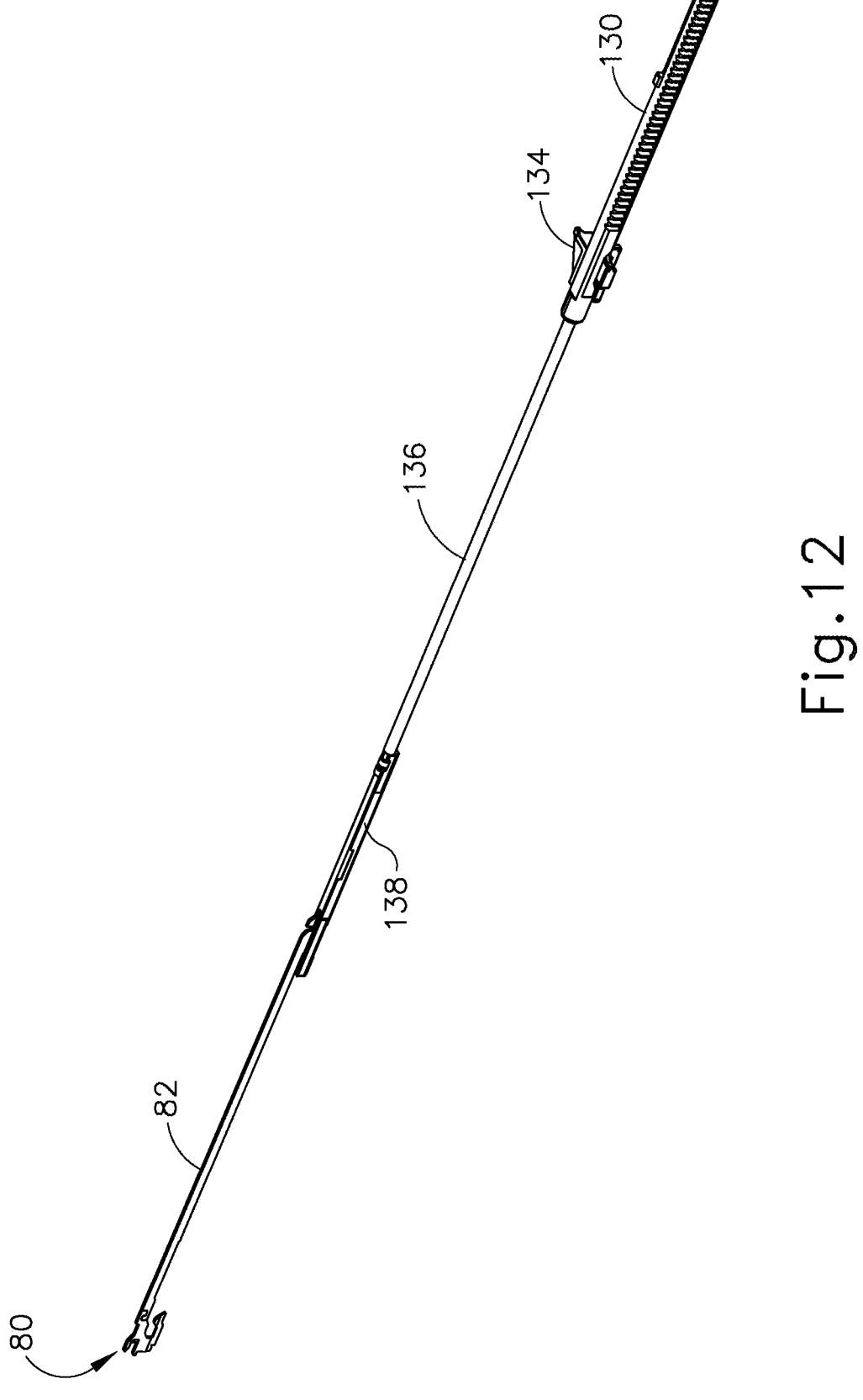
FIG. 12 depicts a perspective view of an elongate member from the drive assembly of FIG. 11, coupled with the firing beam.
Figure 13:
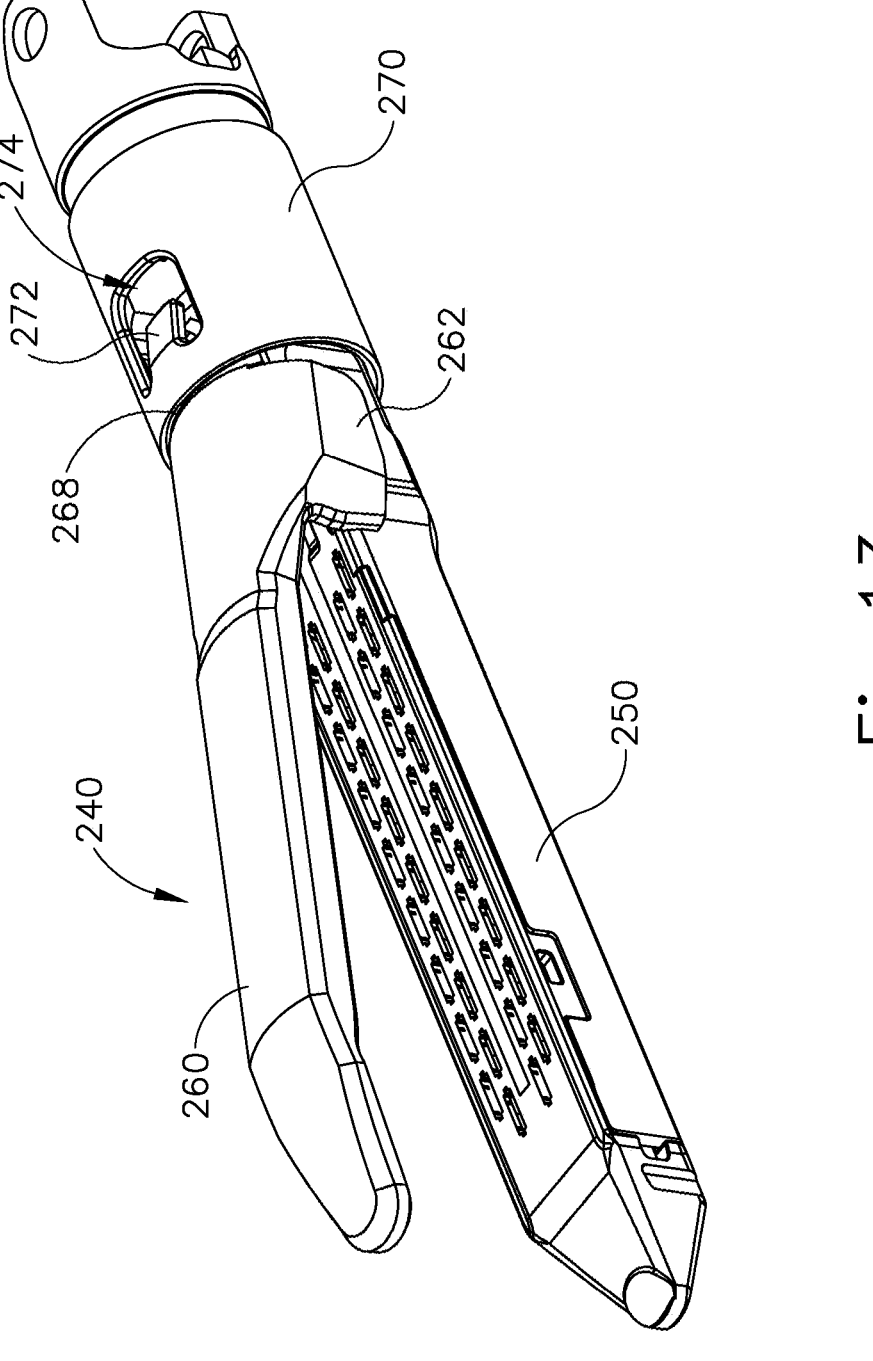
FIG. 13 depicts a perspective view of another illustrative end effector for use with the instrument of FIG. 1.
Figure 14A:
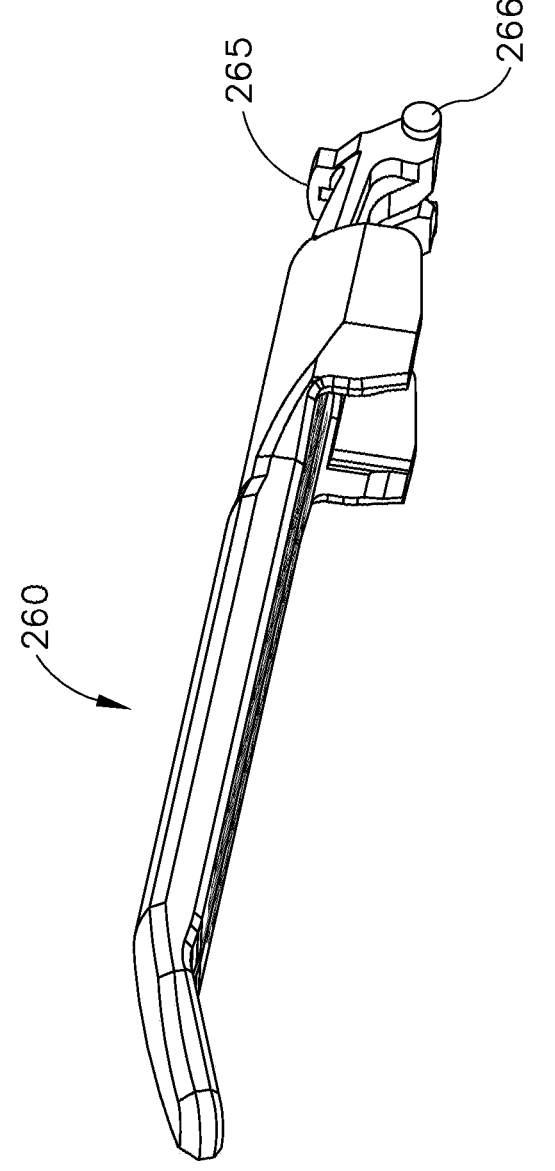
FIG. 14A depicts a perspective view of an anvil of the end effector of FIG. 13.
Figure 14B:
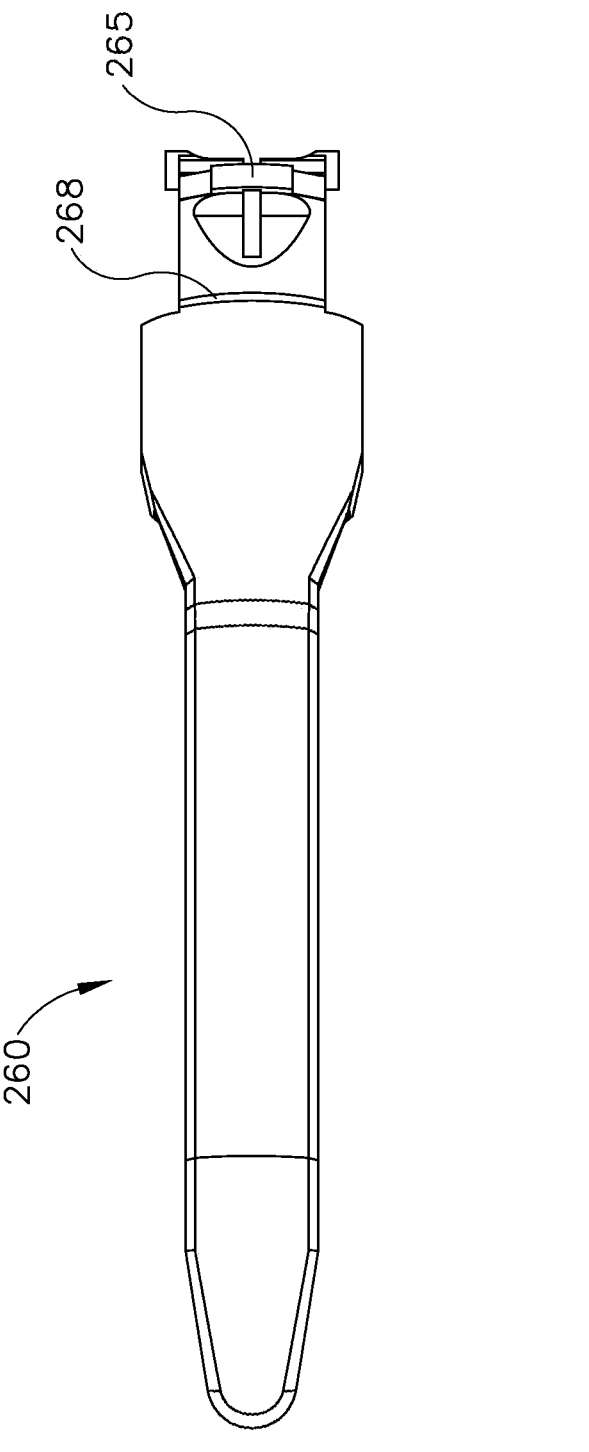
FIG. 14B depicts a top plan view of the anvil of FIG. 14A.
Figure 15:
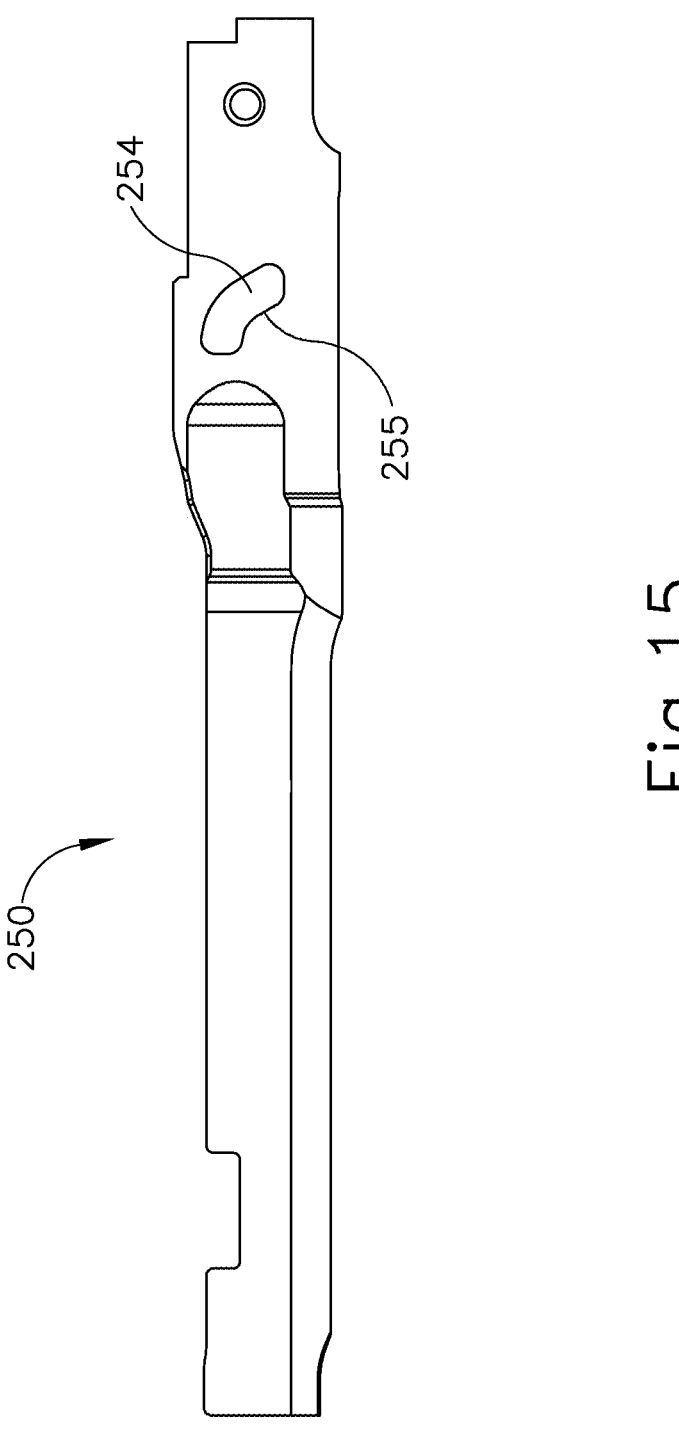
FIG. 15 depicts a side elevational view of a lower jaw of the end effector of FIG. 13.
Figure 16:
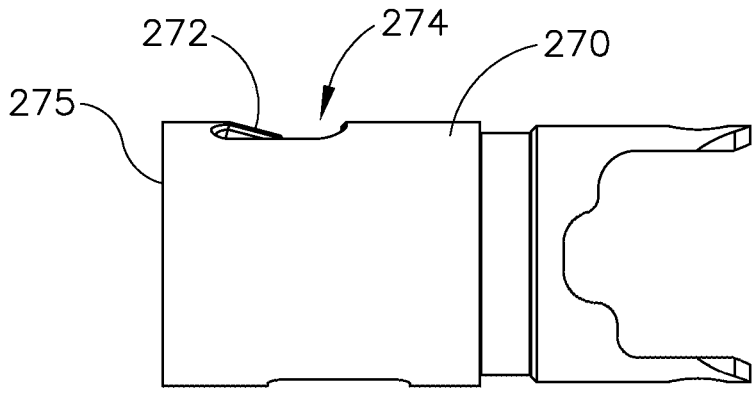
FIG. 16 depicts a side elevational view of a closure ring of the end effector of FIG. 13.
Figure 17:
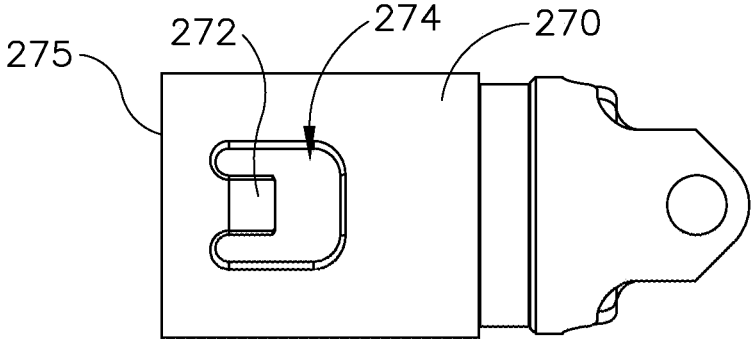
FIG. 17 depicts a top plan view of the closure ring of FIG. 16.

Once firing beam (82) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (26) at this stage of operation. In this operational state, current flows through a reverse direction indicator (114) (e.g., an LED, etc.) to provide a visual indication to the operator that motor (102) rotation has been reversed. In the present example, and as best seen in FIG. 12, a switch actuation arm (134) extends laterally from rack member (130), and is positioned to engage end-of-stroke switch (112) when firing beam (82) reaches a distal-most position (e.g., after tissue (90) has been severed and staples (77) have been driven into tissue (90)). Various other suitable ways in which end-of-stroke switch (112) may be automatically switched to a closed position when firing beam (82) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle assembly (20) of the present example also includes a manual return switch (116), which is also shown in circuit (100). In the present example, return switch (116) is activated by actuating reverse switch (27), which is shown on handle assembly (20) in FIG. 1. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114). In some versions, handle assembly (20) further includes a mechanical return feature that enables the operator to manually reverse firing beam (82) and thereby retract firing beam (82) mechanically. In the present example, this manual return feature comprises a lever that is covered by a removable panel (21) as shown in FIG. 1. Manual return switch (116) and the mechanical return feature are each configured to act as a "bailout" feature, enabling the operator to quickly begin retracting firing beam (82) proximally during a firing stroke. In other words, manual return switch (116) or the mechanical return feature may be actuated when firing beam (82) has only been partially advanced distally.

In some versions, one or more of switches (26, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 10:
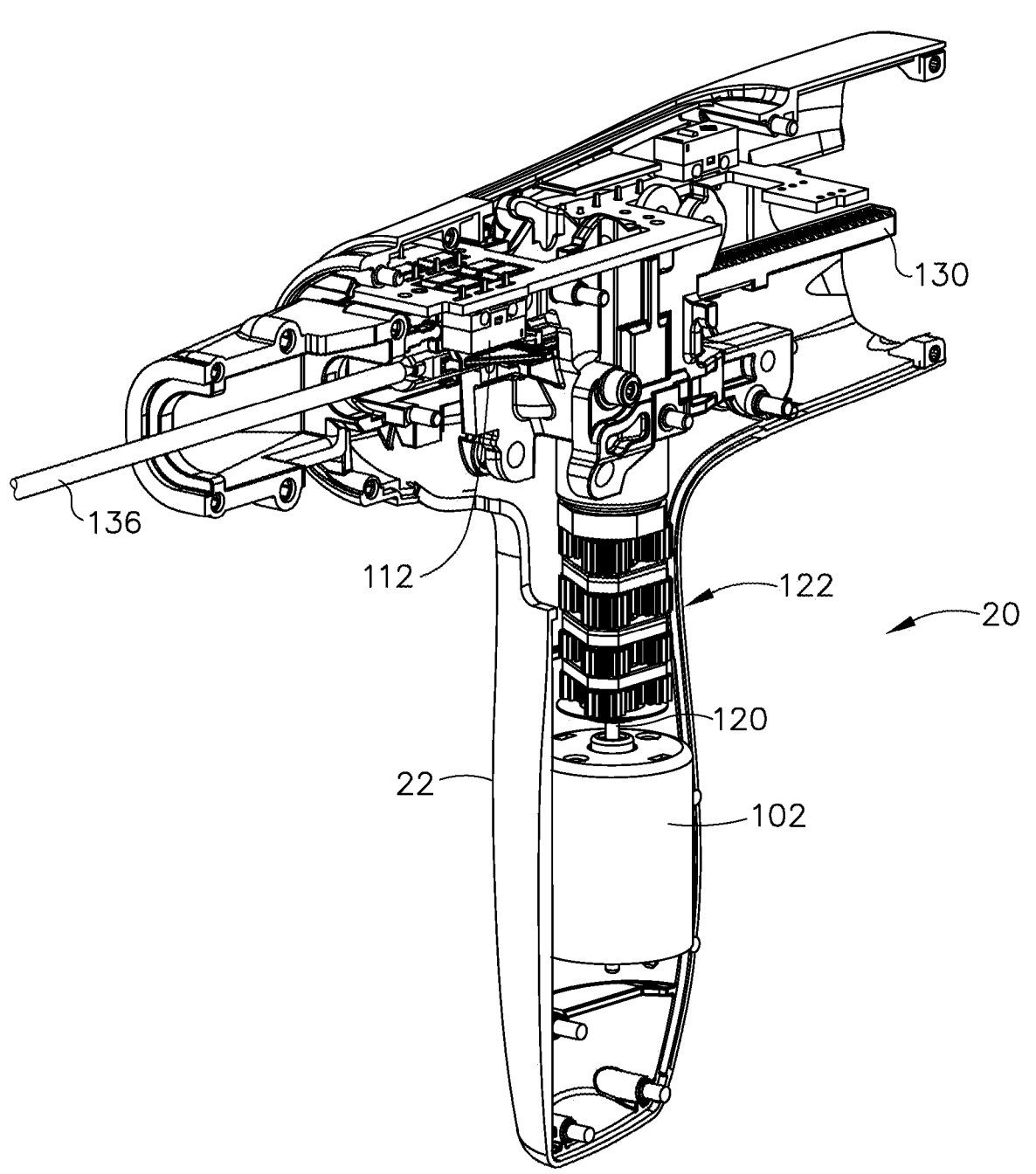
FIG. 10 depicts a perspective view of the handle assembly of the instrument of FIG. 1, with a housing half and some internal components removed.
Figure 11:
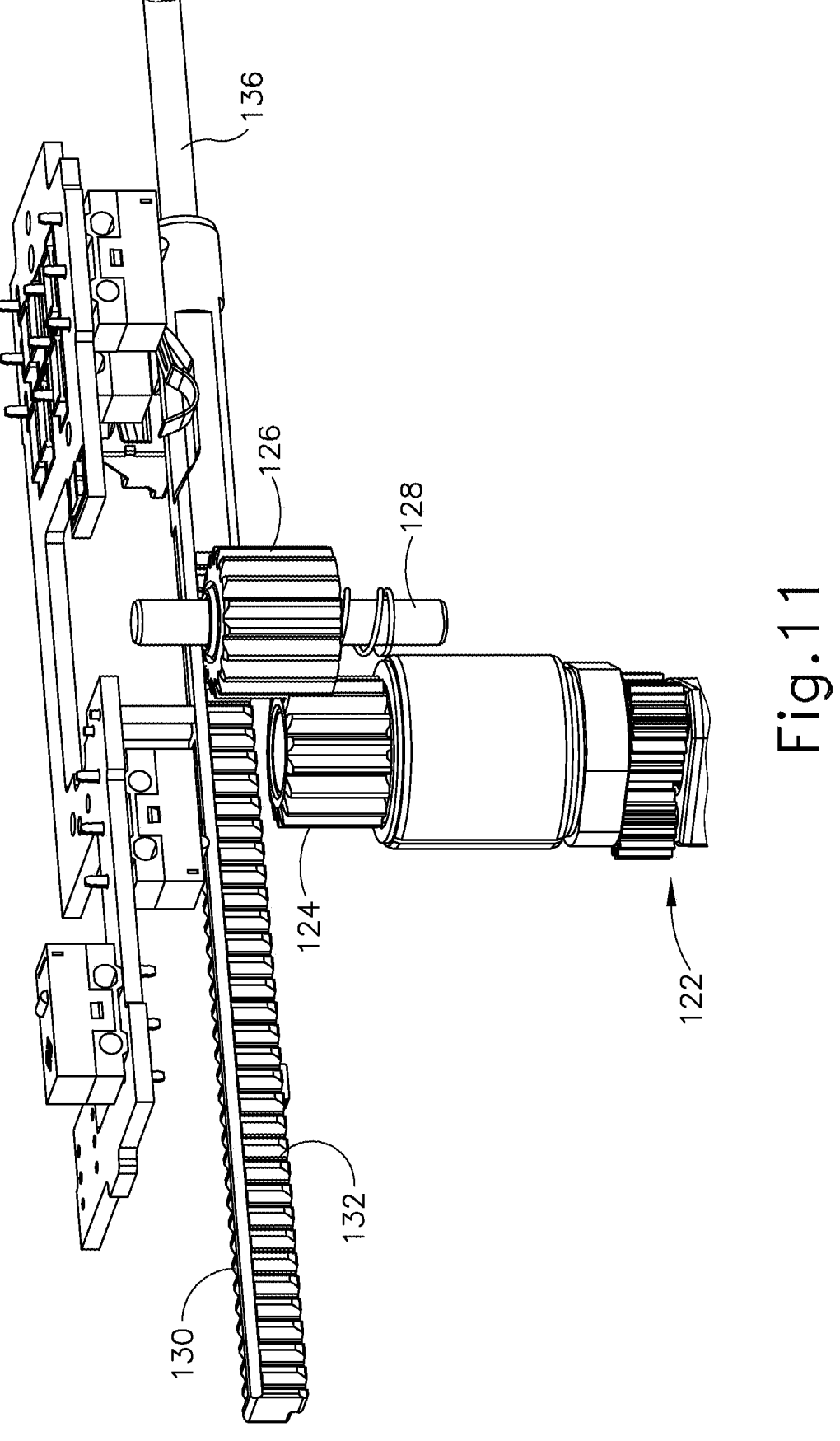
FIG. 11 depicts a perspective view of drive assembly components from the handle assembly of FIG. 10.

FIG. 10 shows motor (102) positioned within pistol grip (22) of handle assembly (20). Alternatively, motor (102) may be positioned elsewhere within handle assembly (20). Motor (102) has a drive shaft (120) that is coupled with a gear assembly (122). Thus, when motor (102) is activated, drive shaft (120) actuates gear assembly (122). As shown in FIG. 11, gear assembly (122) is in communication with a drive gear (124), which meshes with an idler pinion (126). Pinion (126) is disposed on a shaft (128) that is supported within handle assembly (20) and that is oriented parallel to drive shaft (120) of motor (102). Pinion (126) is further engaged with a rack member (130). In particular, pinion (126) meshes with teeth (132) at the proximal end of rack member (130). Rack member (130) is slidably supported in handle assembly (20). It should be understood from the foregoing that, when motor (102) is activated, the corresponding rotation of drive shaft (120) is communicated to pinion (126) via gear assembly (122), and the corresponding rotation of pinion (126) is converted to translation of rack member (130) by teeth (132). As shown in FIGS. 10-12, an elongate member (136) extends distally from rack member (130). As shown in FIG. 12, a coupling member (138) joins firing beam (82) with elongate member (136). Rack member (130), elongate member (136), coupling member (138), firing beam (82), and knife member (80) all translate together relative to handle assembly (20) in response to activation of motor (102). In other words, activation of motor (102) ultimately causes firing beam (82) to translate longitudinally, the direction of such translation depending on the direction of rotation of drive shaft (120).

It should be understood that a distal portion of elongate member (136), coupling member (138), and firing beam (82) extend through shaft assembly (130). A portion of firing beam (82) also extends through articulation section (34). In some versions, rack member (130), elongate member (136), and coupling member (138) are all substantially straight and rigid; while firing beam (82) has sufficient flexibility to bend at articulation section (34) and translate longitudinally through articulation section (34) when articulation section (34) is in a bent or articulated state.

In addition to or in lieu of the foregoing, the features operable to drive firing beam (82) may be configured in accordance with at least some of the teachings of U.S. Pat. No. 8,453,914, the disclosure of which is incorporated by reference herein. Other suitable components, features, and configurations for providing motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be actuated in accordance with at least some of the teachings of any other reference cited herein.

Figure 8:
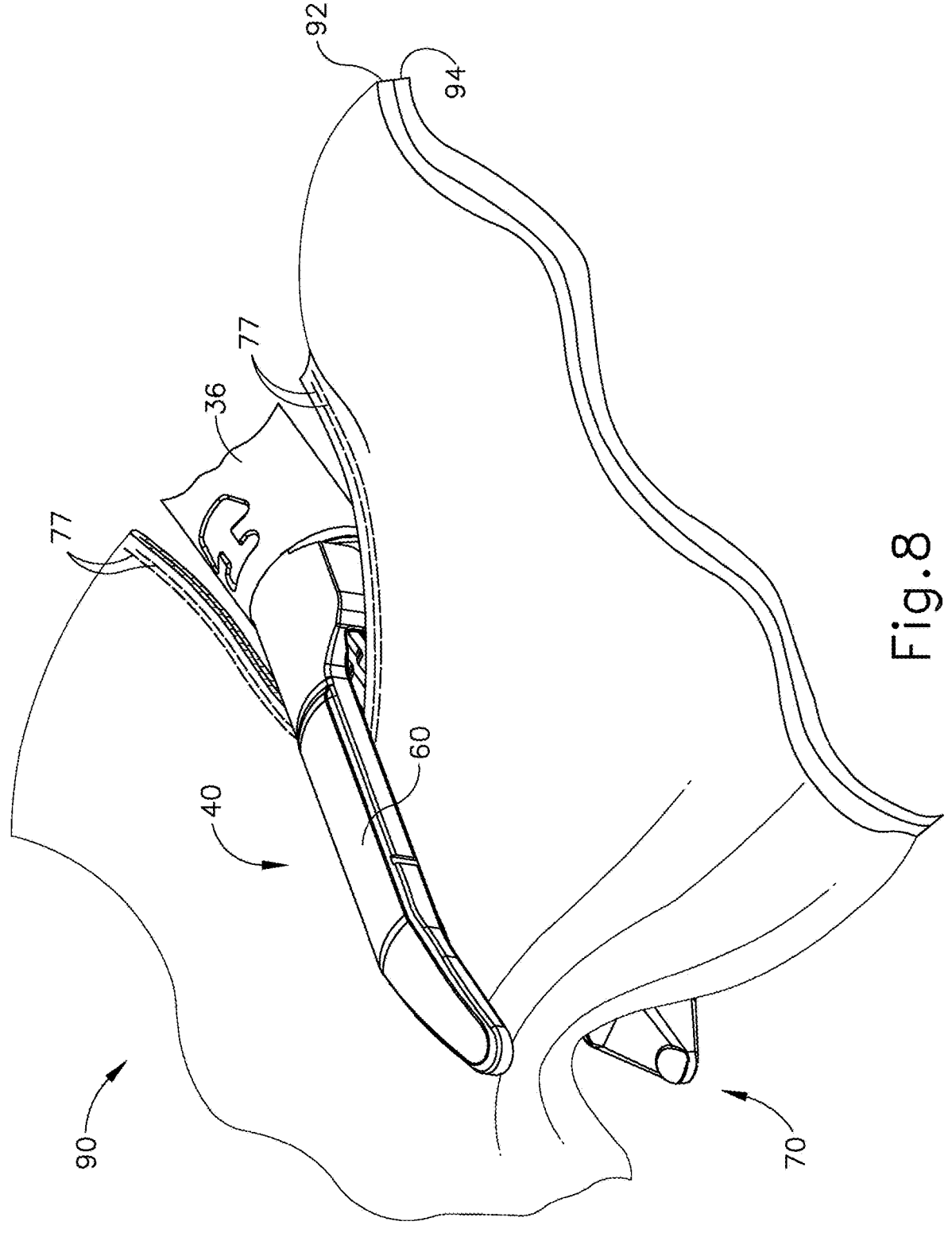
FIG. 8 depicts a perspective view of the end effector of FIG. 3, positioned at tissue and having been actuated once in the tissue.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may sever tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional illustrative modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Illustrative Alternative End Effector

FIGS. 13-19B depict another illustrative end effector (240) that may be readily incorporated into surgical stapling and severing instrument (10). End effector (240) is substantially similar to end effector (40) described above. As a result, the components of end effector (240) are substantially similar and function substantially similarly to those of end effector (40) described above. Accordingly, the description of those previously discussed components of end effector (240) will not be repeated here. Similar to end effector (40) described above, end effector (240) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (240) and the distal portion of shaft assembly (30) may be inserted directly through a thoracotomy or other type of incision. The manner in which tissue captured within end effector (240) is cut and stapled by actuating firing trigger (26) to drive firing beam (82) is substantially similar to that described above with respect to end effector (40).

A. Illustrative Actuation of End Effector

End effector (240) comprises a pivotable anvil (260), a lower jaw (250), and a closure ring (270). Pivotable anvil (260) is similar to pivotable anvil (60) and includes a pair of flanges (262) and a pair of integral, outwardly extending pins (266) that are similar to pins (66) described above. Lower jaw (250) is similar to lower jaw (50) of end effector (40) and includes a pair of openings (254) that are similar to slots (54) described above. In this example, openings (254) comprise elongated, curved slots. Each opening (254) is configured to receive a respective pin (266) of anvil (260) such that anvil (260) is pivotable relative to lower jaw (250). Anvil (260) is pivotable toward and away from lower jaw (250) between a fully opened position (shown in FIGS. 13 and 19B) and a fully closed position (shown in FIG. 18B). Use of the term "pivotable" (and similar terms with "pivot" as a base) should not be read as necessarily requiring pivotal movement about a fixed axis. For instance, in the present example, anvil (260) pivots about an axis that is defined by pins (266), which slide along openings (254) of lower jaw (250) as anvil (260) moves toward lower jaw (250). In such versions, the pivot axis translates along the path defined by openings (254) while anvil (260) simultaneously pivots about that axis. In addition or in the alternative, the pivot axis may slide along openings (254) first, with anvil (260) then pivoting about the pivot axis after the pivot axis has slid a certain distance along the openings (254). It should be understood that such sliding/translating pivotal movement is encompassed within terms such as "pivot," "pivots," "pivotal," "pivotable," "pivoting," and the like. Of course, some versions may provide pivotal movement of anvil (260) about an axis that remains fixed and does not translate within a slot or channel, etc.

Similar to closure ring (36) described above, closure ring (270) also facilitates the transition of anvil (260) between the fully opened position and the fully closed position. As shown, closure ring (270) comprises vertical surface (275) and tab (272). Tab (272) is positioned within a lateral hole or opening (274) that is formed through the sidewall of closure ring (270). Vertical surface (275) is positioned distal of tab (272) and is configured to engage vertical surface (268) of anvil (260). Opening (274) is configured to receive tab (265) of anvil (260). Tab (272) of closure ring (270) extends proximally within opening (274) and slopes downwardly toward the central longitudinal axis of closure ring (270).

Figure 18A:
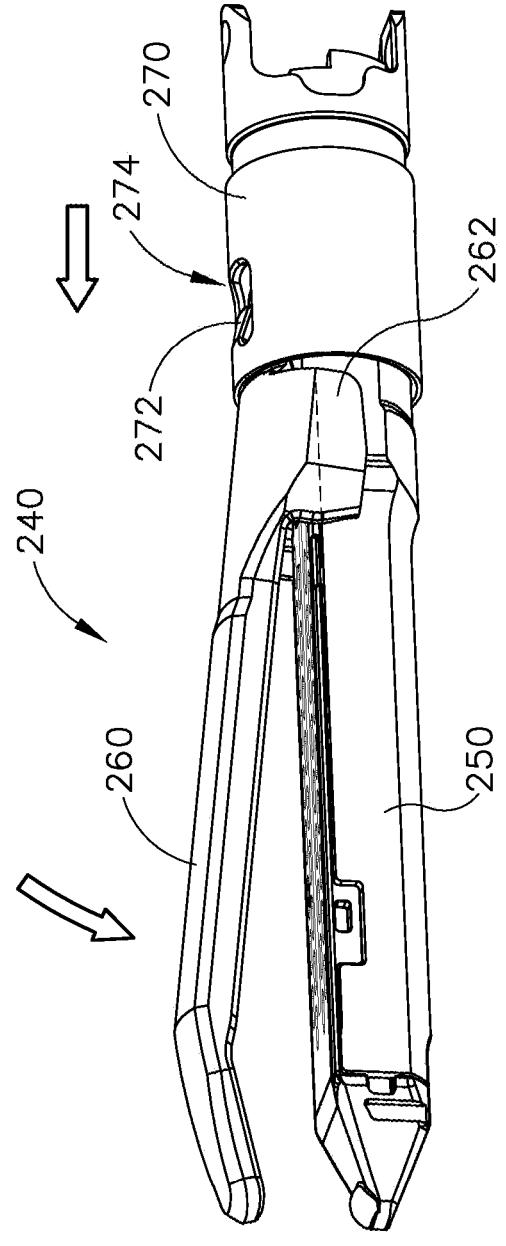
FIG. 18A depicts a perspective view of the end effector of FIG. 13 during a first instant of time during closure.
Figure 18B:
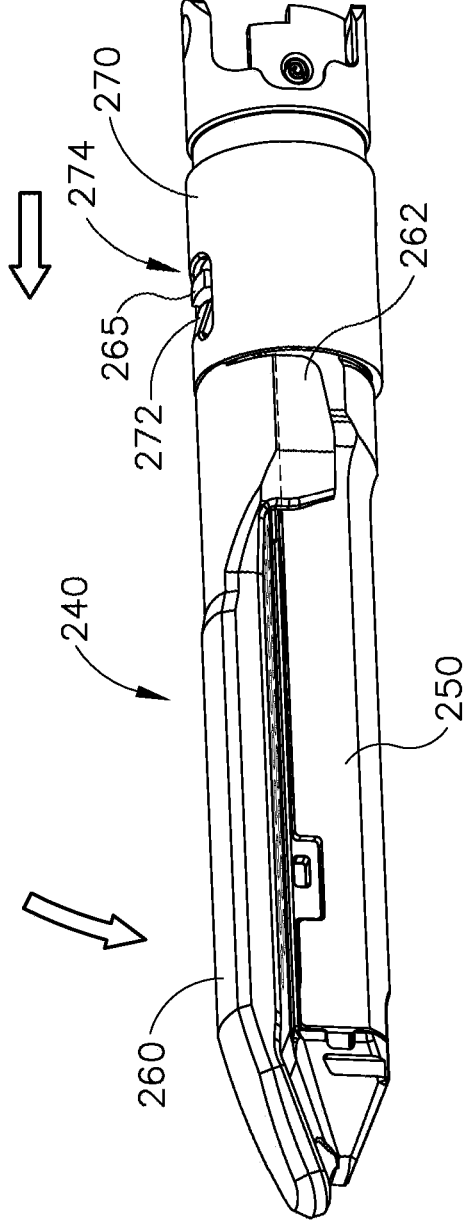
FIG. 18B depicts a perspective view of the end effector of FIG. 13 fully closed.

In an illustrative use, instrument (10) may be inserted to a surgical site in a nonarticulated state, with anvil (260) and lower jaw (250) closed. Once articulation section (34) and end effector (240) are inserted to the desired site within the patient, anvil (260) and lower jaw (250) may be opened, as described below, and articulation section (34) may be remotely articulated by an articulation control knob (35), such that end effector (240) may be deflected to a desired angle (a) to position tissue between anvil (260) and lower jaw (250). Alternatively, end effector (240) may be deflected at articulation section (34) prior to opening anvil (260) and lower jaw (250). Closure trigger (24) may then be actuated toward pistol grip (22) to cause the closing of anvil (260) toward lower jaw (250), as shown in FIGS. 18A-18B. Such closing of anvil (260) is provided through a closure tube (32) and closure ring (270), which both longitudinally translate relative to handle assembly (20) and lower jaw (250) in response to pivoting of closure trigger (24) relative to pistol grip (22). Articulation section (34) is operable to communicate longitudinal movement from closure tube (32) to closure ring (270).

As closure ring (270) translates distally in response to advancement of closure tube (32), closure ring (270) translates relative to anvil (260) to engage anvil (260). As shown in FIGS. 18A-18B, as closure ring (270) translates distally, vertical surface (275) of closure ring (270) contacts vertical surface (268) of anvil (260) thereby causing anvil (260) to also translate distally and pivot toward lower jaw (250). Vertical surface (268) of anvil (260) has a curved profile, which concentrates the axial closure load at the center of vertical surface (275). In some instances, as anvil (260) closes relative to lower jaw (250), anvil (260) may slightly deflect laterally relative to closure ring (270). If anvil (260) is deflected laterally, the curved profile of vertical surface (268) transfers the load centrally to closure ring (270) regardless of the lateral deflection of anvil (260) and eventually corrects the deflection to properly align anvil (260). Also, by concentrating the load centrally, the tissue compression ability at the tip of anvil (260) is increased due to better mechanical advantage and better load transfer efficiency.

As anvil (260) translates distally, each pin (266) contacts the ramped outer wall (255) of its respective opening (254) of lower jaw (250). The curved surface of pin (266) and ramped outer walls (255) of openings (254) allow pins (266) to translate along openings (254) of lower jaw (250). As anvil (260) continues to translate distally, the ramped outer walls (255) cam against pins (266) to drive anvil (260) to pivot downwardly about pins (266) toward lower jaw (250). Near the end of the closure stroke, pins (266) of anvil (260) transition to shallower angled surfaces of ramped outer wall (255) and anvil (260) reaches the fully closed position. Once end effector (240) is closed, the tissue captured between anvil (260) and lower jaw (250) may be cut and stapled by actuating firing trigger (26) to drive firing beam (82).

Figure 19A:
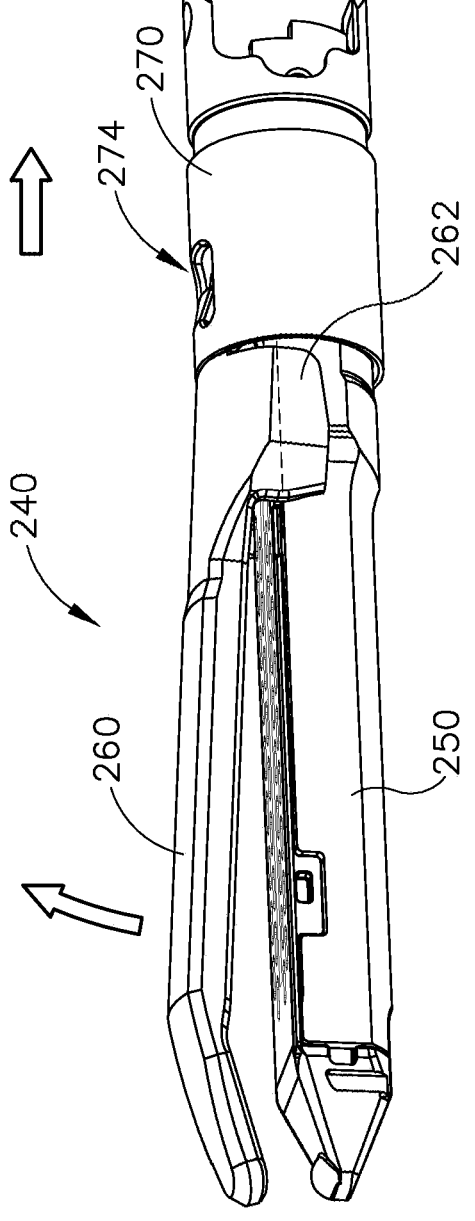
FIG. 19A depicts a perspective view of the end effector of FIG. 13 during a first instant of time during opening.
Figure 19B:
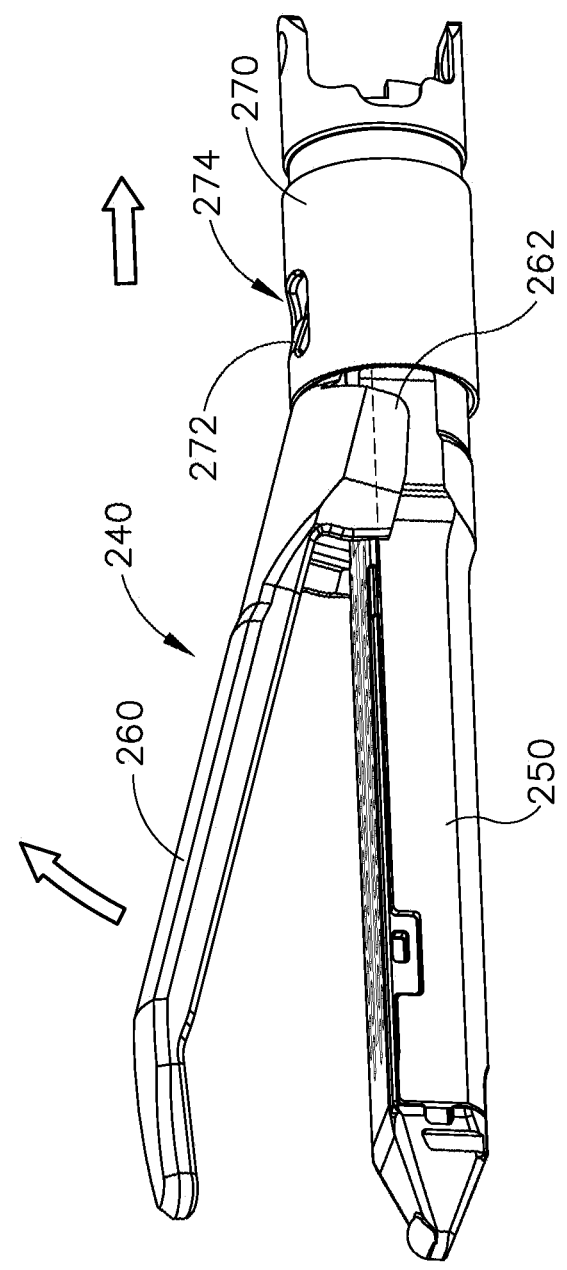
FIG. 19B depicts a perspective view of the end effector of FIG. 13 fully opened.

Once tissue positioned between anvil (260) and lower jaw (250) is cut and stapled, anvil (260) and lower jaw (250) may be opened to release the tissue, then end effector (240) may be pivoted back to the nonarticulated position by articulation control knob (35) and removed from the surgical site, with anvil (260) and lower jaw (250) closed. End effector (240) may then be opened to replace staple cartridge (70) with a new staple cartridge. To open end effector (240), closure trigger (24) may be released away from pistol grip (22) to cause closure ring (270) to translate proximally, as shown in FIGS. 19A-19B. As closure ring (270) translates proximally, vertical surface (275) of closure ring (270) disengages from vertical surface (268) of anvil (260). As closure ring (270) continues to translate proximally, tab (272) of closure ring (270) engages tab (265) of anvil (260) to cause anvil (260) to translate proximally. As anvil (260) translates proximally, pins (266) translate proximally along ramped outer walls (255) of openings (254) and anvil (260) pivots about pins (266) away from lower jaw (250) to the fully opened position, as shown in FIG. 19B. Staple cartridge (70) may be replaced with a new staple cartridge, and end effector (240) may be again inserted to the surgical site for further cutting and stapling.

III. Illustrative Alternative End Effector with Resilient Member

It should be understood that the configuration of an end effector may result in an undesirable lack of precision and stability regarding the interaction of the anvil and the lower jaw. For example, in some embodiments the configuration of certain end effector components and the manner in which they interact may result in unwanted movement or "flopping" of the anvil relative to the lower jaw of the end effector when the anvil is in a fully opened position. It may therefore be desirable to configure the end effector such that the anvil remains in the fully opened position once it reaches that position, at least until a closure stroke is initiated, thereby reducing the unwanted flopping. Various end effectors are described below that include various embodiments of resilient members that may be configured to improve the precision and stability of the respective end effector by urging the anvil to remain in the fully opened position thereby reducing the unwanted flopping.

It should also be understood that the configuration of an end effector may have a significant impact on the profile of the closure stroke (i.e., the transition of the anvil toward a fully closed position). Furthermore, it will be understood that the profile of the closure stroke may have a significant impact on how the end effector captures the layer(s) of tissue within the end effector, which ultimately impacts the quality and precision of the cutting and stapling accomplished by the surgical stapler. It may therefore be desirable to configure the end effector such that it provides a substantially smooth profile during the closure stroke. At least some of the various embodiments of resilient members described below may be configured to improve the smoothness the profile of at least a portion of the closure stroke of the respective end effector by applying a force on the anvil during at least a portion of the closure stroke.

A. Illustrative Elastomeric Insert for End Effector

Figure 20:
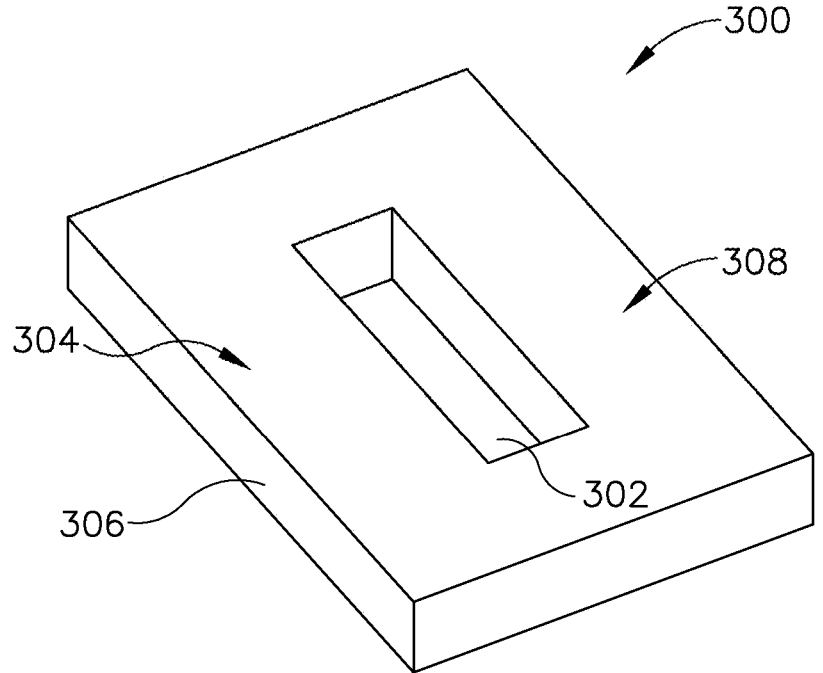
FIG. 20 depicts a perspective view of an illustrative elastomeric insert.
Figure 21:
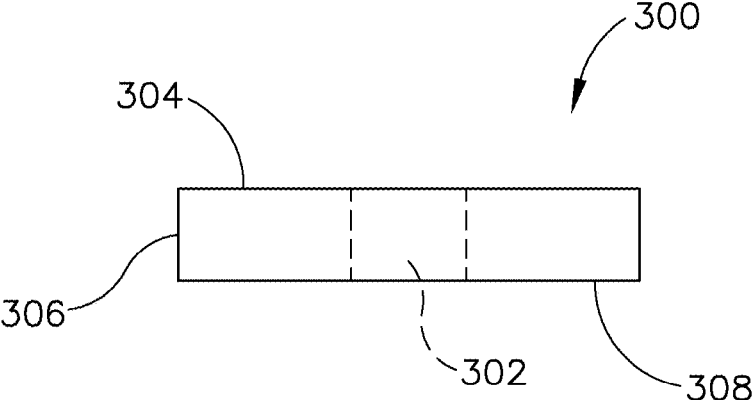
FIG. 21 depicts a side elevational view of the elastomeric insert of FIG. 20.
Figure 22:
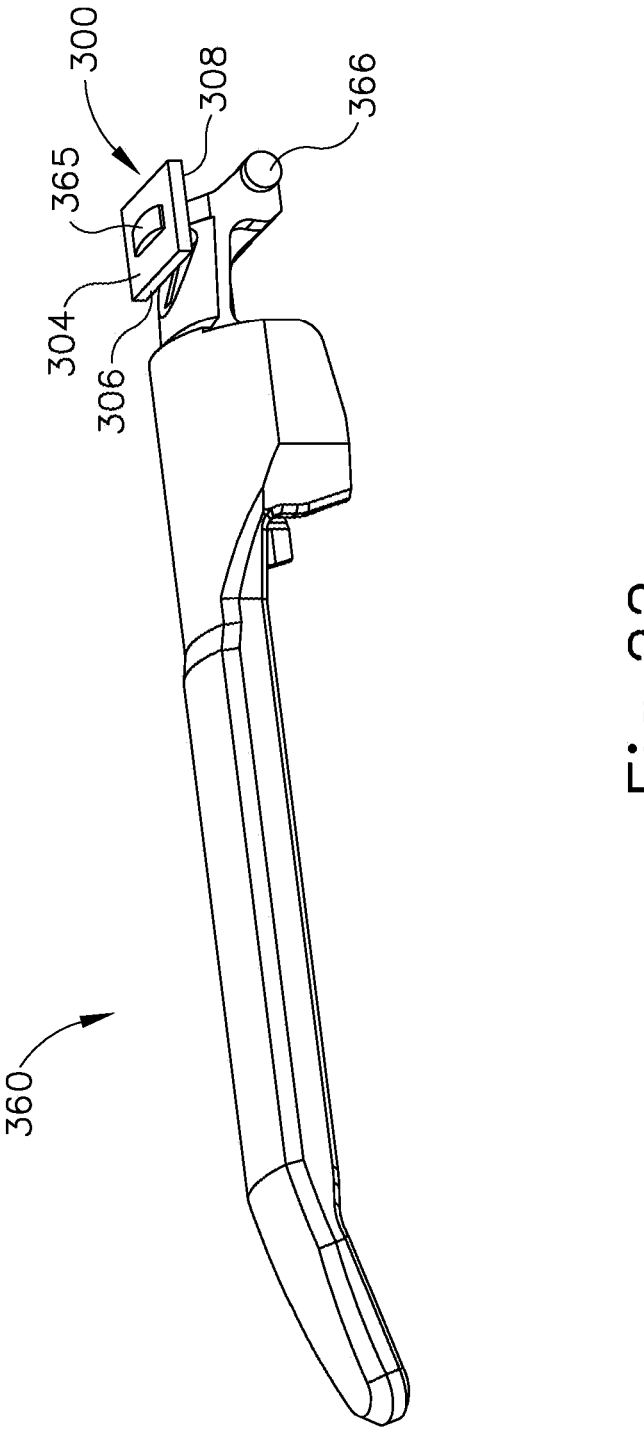
FIG. 22 depicts a side elevational view of the elastomeric insert of FIG. 20 assembled together with an illustrative anvil.
Figure 23:
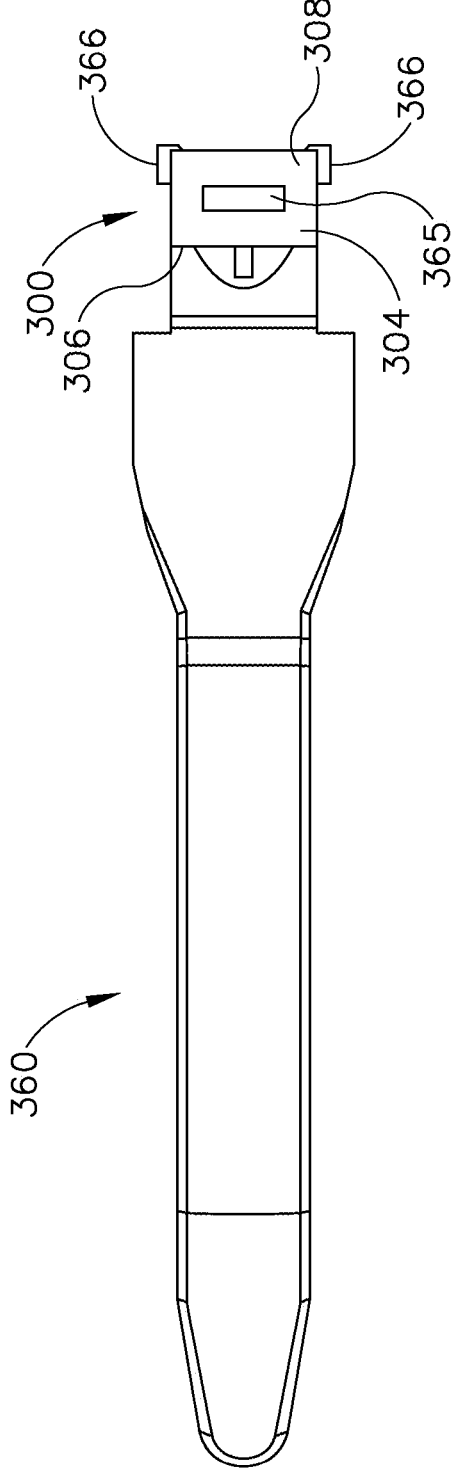
FIG. 23 depicts a top plan view of the elastomeric insert and anvil of FIG. 22.

FIGS. 20-21 depict an illustrative elastomeric insert (300) configured to be used in conjunction with an illustrative end effector and closure ring, including but not limited to end effector (240) and closure ring (270) described above. FIGS. 22-23 depict elastomeric insert (300) positioned on an anvil (360) that is substantially similar to anvil (260) described above. FIGS. 24A-25B depict detailed views of an end effector (340) comprising elastomeric insert (300), anvil (360) and closure ring (370) and the interaction between elastomeric insert (300), anvil (360) and closure ring (370) when end effector (340) is in a fully closed position and a fully opened position. Closure ring (370) is substantially similar to closure ring (270) described above and includes a tab (372) positioned within an opening (374) similar to tab (272) and opening (274) described above. End effector (340) is substantially similar to end effectors (40, 240) described above. Except for the addition of elastomeric insert (300), the components of end effector (340) are substantially similar and function substantially similarly to those of end effectors (40, 240) described above. Accordingly, the description of those previously discussed components of end effector (340) will not be repeated here.

As shown in FIGS. 20-25B, elastomeric insert (300) comprises a substantially rectangularly shaped insert comprising an opening (302), a distal flange (304) having a distal surface (306) and a proximal flange (308). Of course, insert (300) may have a variety of alternative shapes, including but not limited to circular, ovular, triangular, etc. In this embodiment, opening (302) is sized and shaped to receive at least a portion of an anvil, such as tab (365) of anvil (360). In particular, in the illustrated embodiment, opening (302) comprises a profile that is substantially similar to the profile of tab (365). As shown, opening (302) is positioned substantially in the center of elastomeric insert (300) between distal flange (304) and proximal flange (308). In other embodiments, the opening (302) may be positioned elsewhere within the body of the insert (e.g., so that the central axis of the opening (302) is substantially off-center relative to the overall dimensions of the insert), provided that the opening is still positioned between a distal flange and a proximal flange. In addition, in the illustrated embodiment, opening (302) extends through the entire thickness of elastomeric insert (300). In other embodiments, the opening may extend through only a portion of the thickness of the insert, provided the opening is still configured to receive at least a portion of a corresponding anvil, such as tab (365) of anvil (360).

Insert (300) may comprise an elastomeric material that is compressible in response to a load being applied to the insert (300). The material of insert (300) may also be conformable to allow insert (300) to sufficiently occupy at least a portion of the gap around the components located at an interface of closure ring (370) and anvil (360). In preferred embodiments, insert (300) comprises a material that is suitable and acceptable for use in medical procedures, including surgical procedures of the type described herein. By way of example only, elastomeric insert (300) may comprise santoprene, polyurethane, isoprene, Versaflex GLS 360-135, some other compliant plastic material(s), some other rubber compliant material(s), foam, and/or any other suitable materials capable of improving the stability of anvil (360) by providing a resistive load sufficient to bias anvil (360) to remain in a fully opened position once anvil (360) is in a fully opened position thereby reducing undesired movement or "flopping" of anvil (360) when anvil (360) is in a fully opened position, while also dampening the closure profile to provide a smooth closure as anvil (360) transitions toward a fully closed position.

As shown in FIGS. 22-23, elastomeric insert (300) is positioned on anvil (360) such that at least a portion of tab (365) of anvil (360) is received within the opening (302) of elastomeric insert (300). Accordingly, distal flange (304) of elastomeric insert (300) is positioned distally relative to tab (365) and proximal flange (308) of elastomeric insert (300) is positioned proximally relative to tab (365). As illustrated by FIGS. 24A-25B, when anvil (360) is assembled together with closure ring (370), elastomeric insert (300) is positioned at an interface between anvil (360) and closure ring (370). Specifically, as shown, distal flange (304) of elastomeric insert (300) is positioned between tab (372) of closure ring (370) and tab (365) of anvil (360).

Similar to anvil (260) described above, during opening and closing, anvil (360) pivots relative to a lower jaw similar to lower jaw (250) described above about an axis that is defined by outwardly extending pins (366), which are similar to pins (266) described above. Pins (366) are configured to interact with openings, such as openings (254), in the lower jaw. Accordingly, similar to anvil (260) described above, the pivot axis of anvil (360) translates along the path defined by the openings in the lower jaw while anvil (360) simultaneously pivots about that axis. In addition or in the alternative, the pivot axis may slide along the openings first, with anvil (360) then pivoting about the pivot axis after the pivot axis has slid a certain distance along the openings. It should be understood that such sliding/translating pivotal movement is encompassed within terms such as "pivot," "pivots," "pivotal," "pivotable," "pivoting," and the like. Of course, some versions may provide pivotal movement of anvil (360) about an axis that remains fixed and does not translate within a slot or channel, etc.

Figure 24A:
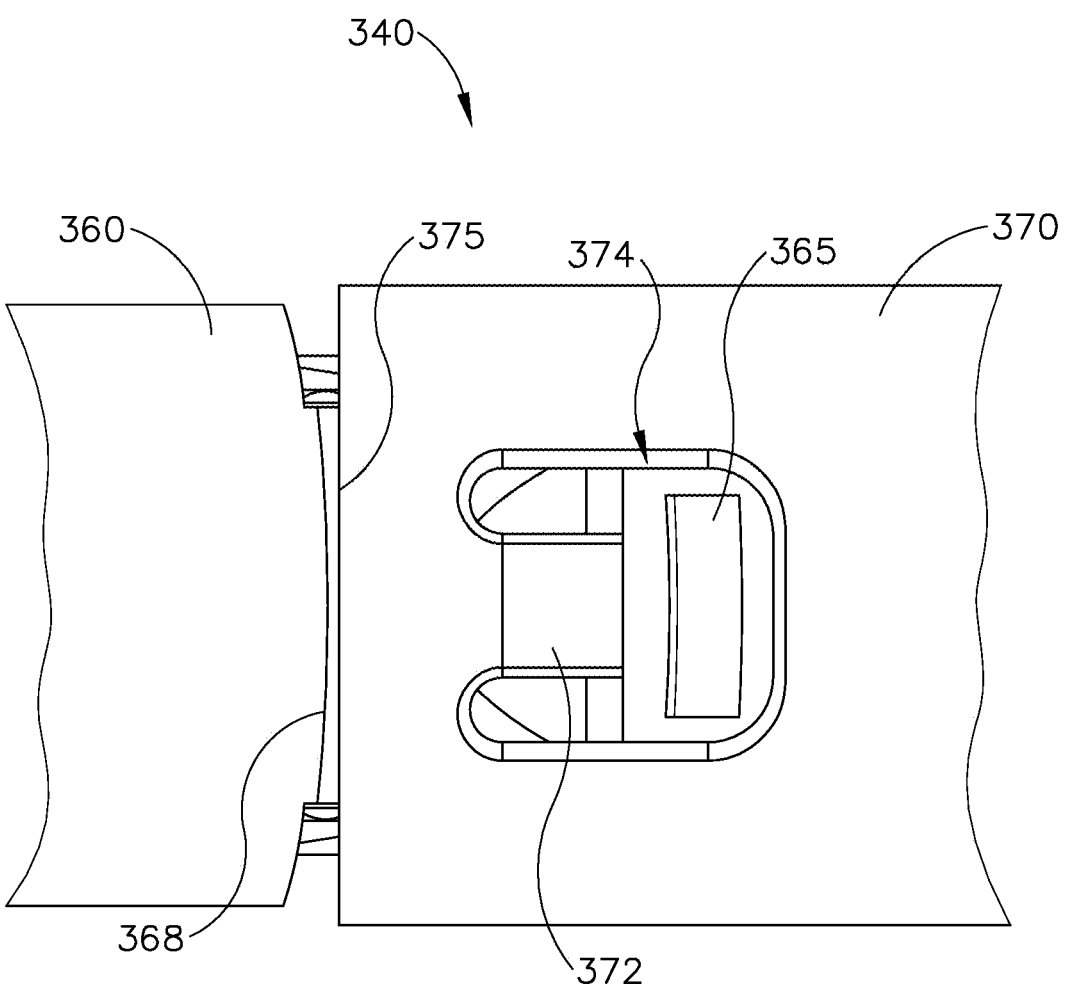
FIG. 24A depicts a detailed top plan view of an illustrative end effector that includes the elastomeric insert and anvil of FIG. 22 when the end effector is fully closed.
Figure 25A:
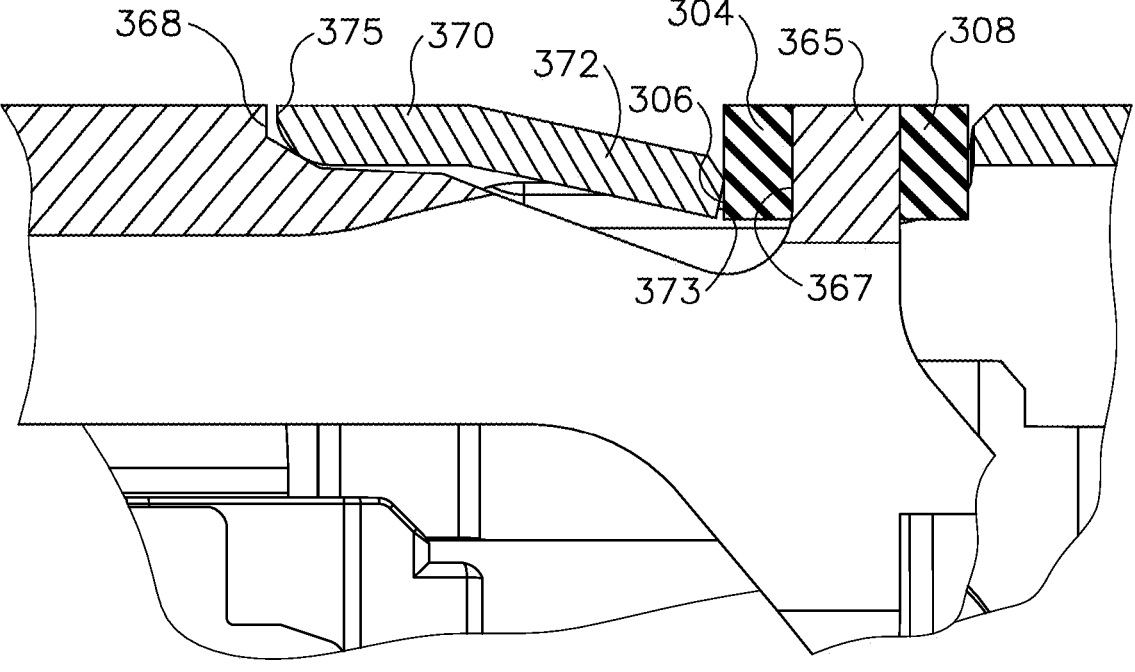
FIG. 25A depicts a detailed cross-sectional side view of the end effector of FIG. 24A when the end effector is fully closed.

FIGS. 24A and 25A depict the interaction between anvil (360) and closure ring (370) when anvil (360) is in a fully closed position. As shown in FIGS. 24A and 25A and as described above with regard to anvil (260) and closure ring (270), when anvil (360) is transitioned toward a fully closed position from an opened position and, consequently when anvil (360) is in a fully closed position, the vertical surface (375) of closure ring (370) engages vertical surface (368) of anvil (360) in order to urge anvil (360) distally, which causes anvil (360) to pivot toward a fully closed position, as described above with regard to end effector (240). As anvil (360) transitions from an opened position toward a fully closed position, tab (372) of closure ring (370) travels distally relative to tab (365) of anvil (360) before vertical surface (375) of closure ring (370) engages vertical surface (368) of anvil (360), which allows distal flange (304) of elastomeric insert (300) to expand distally to occupy at least a portion of the gap between tab (372) and tab (365). During at least a portion of the closure stroke (i.e., the transition of anvil (360) toward a fully closed position), distal surface (306) of elastomeric insert (300) remains in contact with proximal surface (373) located on the proximal end of tab (372) of closure ring (370). In some embodiments, elastomeric insert (300) is dimensioned such that distal surface (306) of elastomeric insert (300) remains in contact with proximal surface (373) of tab (372) of closure ring (370) during the entire closure stroke. By maintaining contact between elastomeric insert (300) and tab (372) of closure ring (370) during at least a portion of the closure stroke, elastomeric insert (300) is able to provide a force on closure ring (370) that can dampen the closure profile, thereby enabling a smooth closure stroke.

Figure 24B:
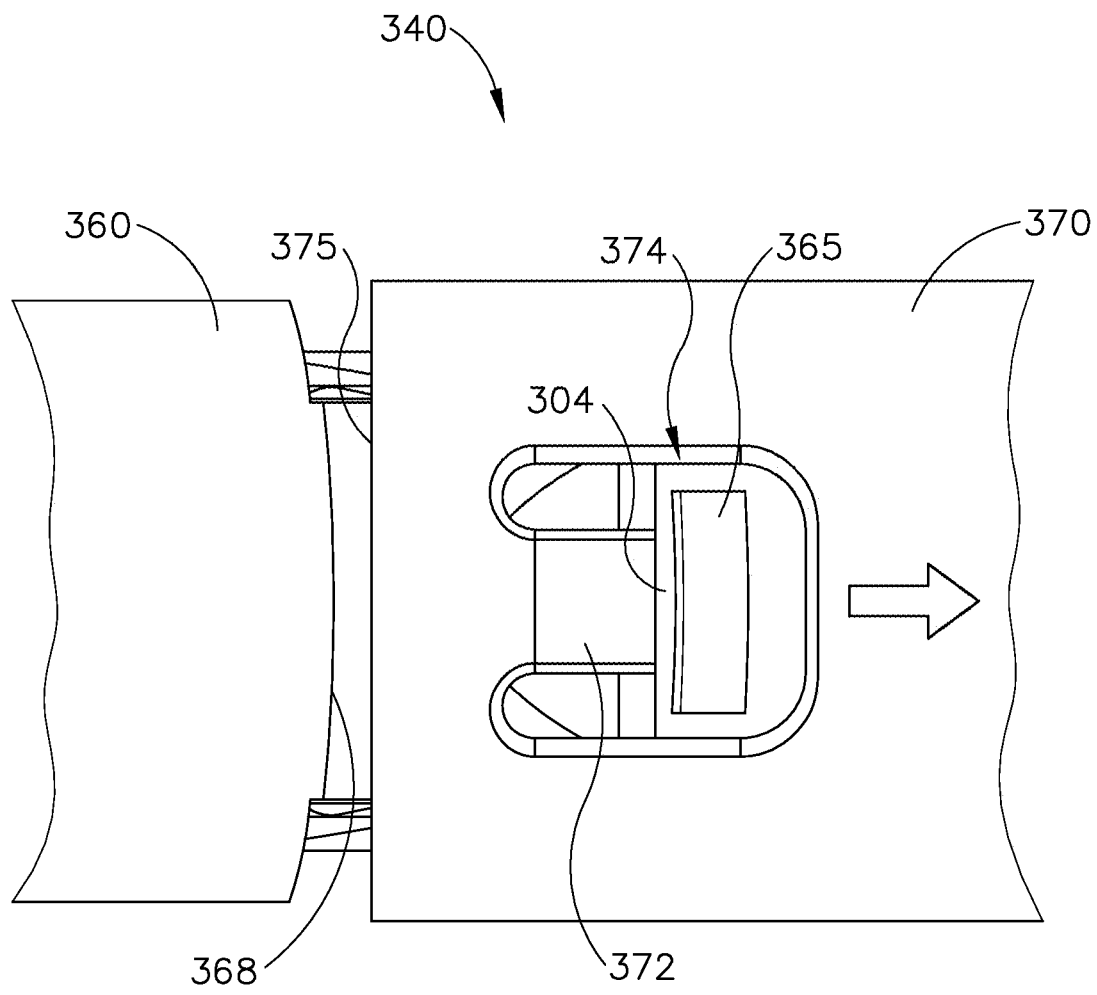
FIG. 24B depicts a detailed top plan view of the end effector of FIG. 24A when the end effector is fully opened.
Figure 25B:
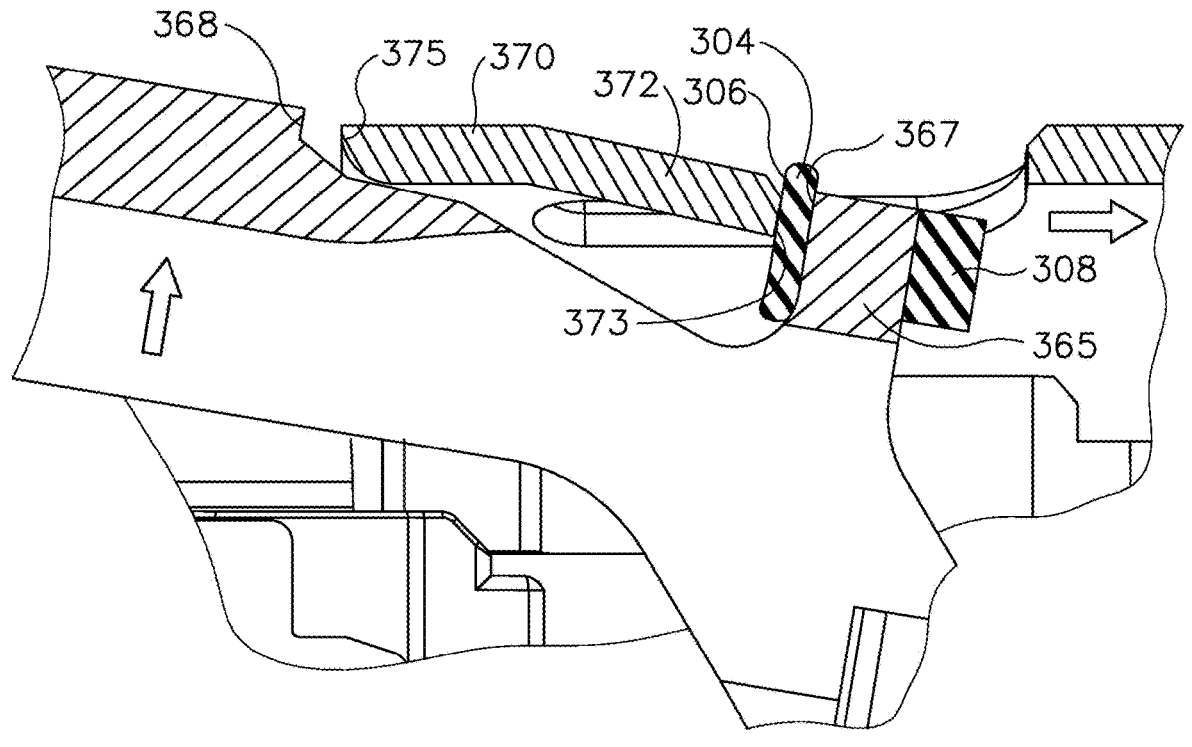
FIG. 25B depicts a detailed cross-sectional side view of the end effector of FIG. 24A when the end effector is fully opened.

Conversely, FIGS. 24B and 25B depict the interaction between anvil (360) and closure ring (370) when anvil (360) is in a fully opened position. As anvil (360) transitions from a fully closed position toward a fully opened position, tab (372) of closure ring (370) travels proximally relative to tab (365) of anvil (360). Accordingly, during at least a portion of the opening stroke (i.e., the transition of anvil (360) toward a fully opened position) elastomeric insert (300) is compressed between closure ring (370) and anvil (360). In some embodiments, elastomeric insert (300) is dimensioned such that distal surface (306) of elastomeric insert (300) is in contact with proximal surface (373) of tab (372) of closure ring (370) during the entire opening stroke. Specifically, as tab (372) of closure ring (370) travels toward tab (365) of anvil (360), distal flange (304) of elastomeric insert (300) is compressed between proximal surface (373) of tab (372) and distal surface (367) of tab (365). As a result of this compression, when anvil (360) is in a fully opened position, elastomeric insert (300) improves the stability of anvil (360) by providing a resistive load on anvil (360) sufficient to bias anvil (360) to remain in the fully opened position thereby reducing undesired movement or "flopping" of anvil (360) when anvil (360) is in the fully opened position. It will be understood that the resistive load provided by elastomeric insert (300) is able to be overcome during a closure stroke of anvil (360) such that anvil (360) is pivotable to a fully closed position. In conjunction with the compression of elastomeric insert (300), closure ring (370) also engages tab (365) through elastomeric insert (300) and drives anvil (360) proximally, thereby causing anvil (360) to pivot toward the fully opened position, as described above with regard to end effector (240).

B. Illustrative Elastomeric Insert with Star-Shaped Opening for End Effector

Figure 26:
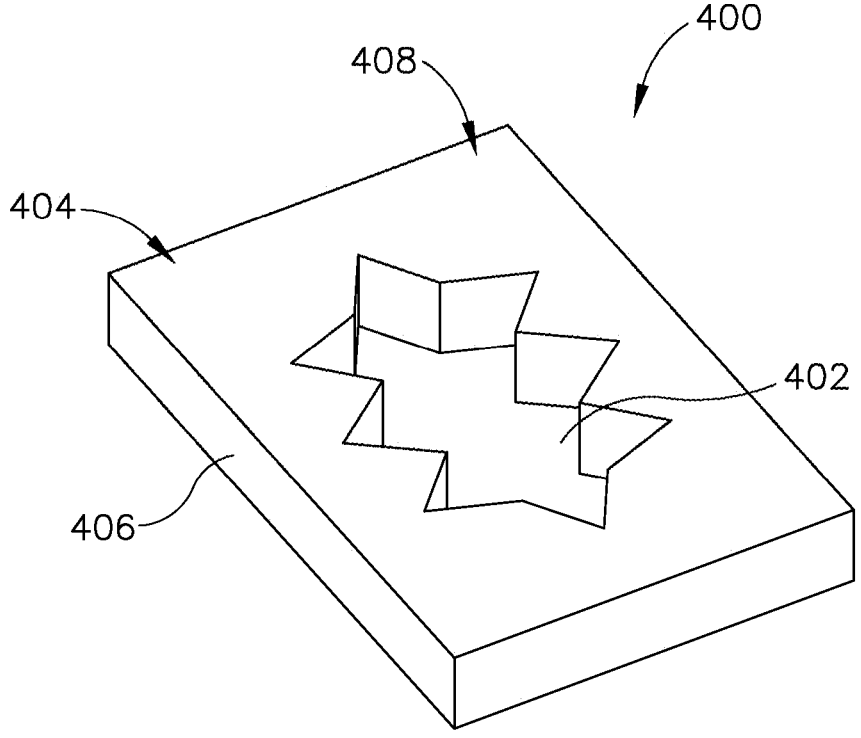
FIG. 26 depicts a perspective view of another illustrative elastomeric insert.
Figure 27:
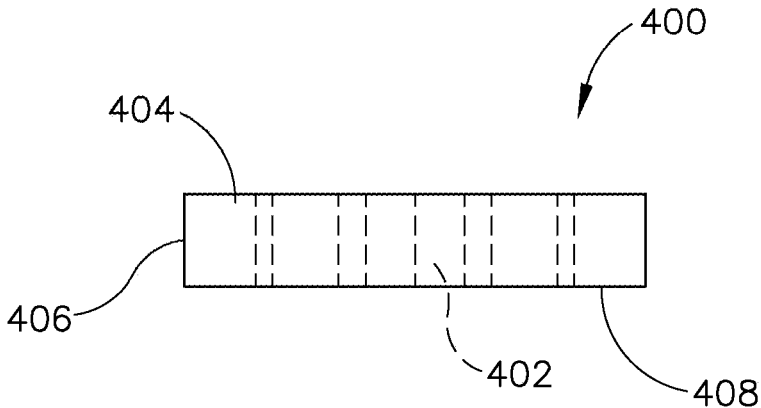
FIG. 27 depicts a side elevational view of the elastomeric insert of FIG. 26.
Figure 28:
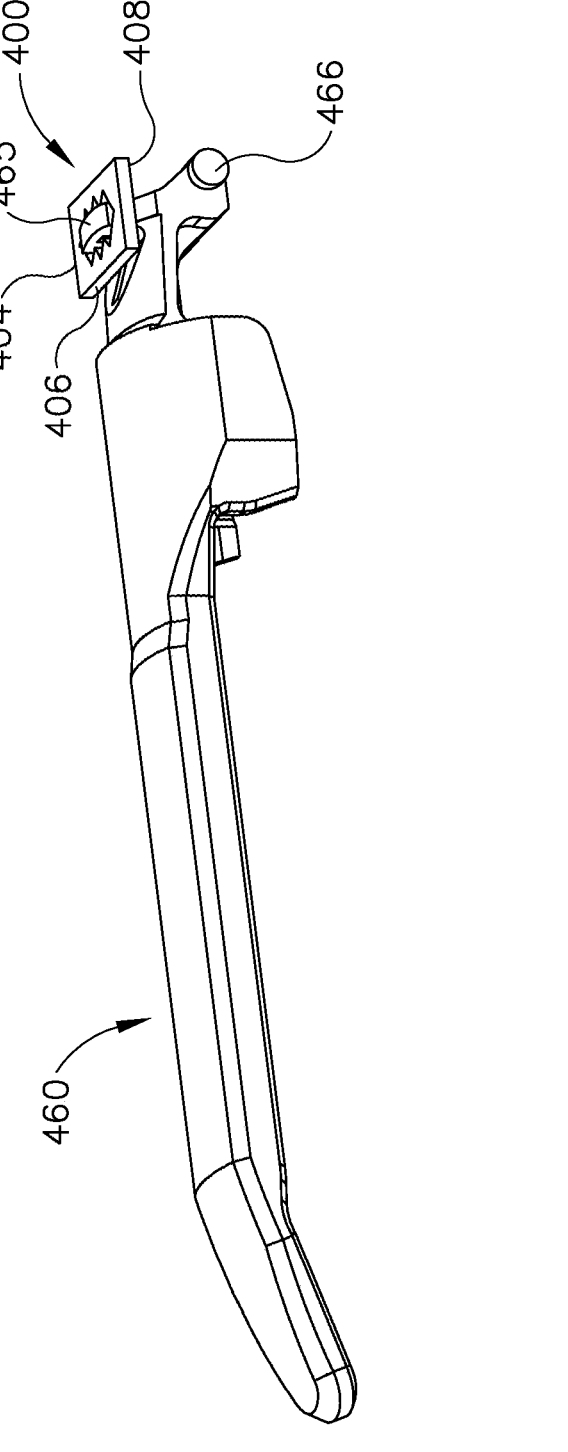
FIG. 28 depicts a side elevational view of the elastomeric insert of FIG. 26 assembled together with an illustrative anvil.
Figure 29:
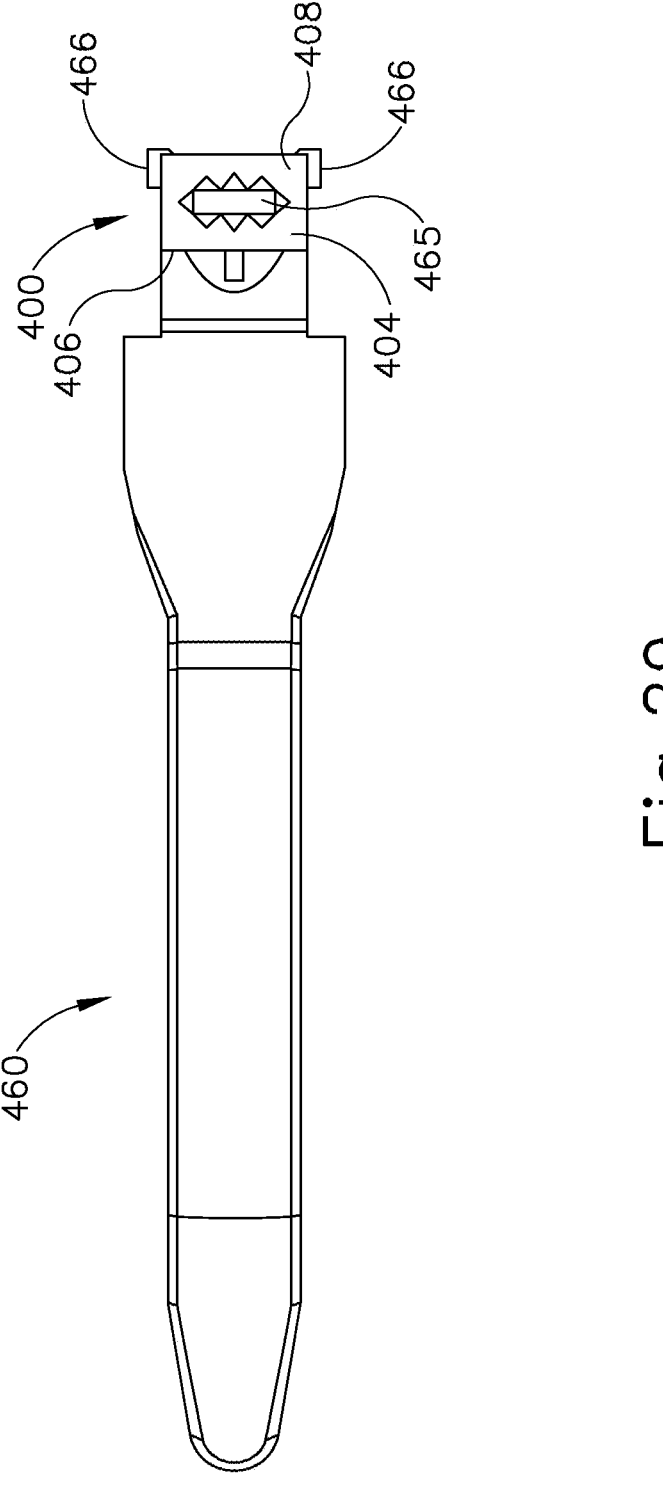
FIG. 29 depicts a top plan view of the elastomeric insert and anvil of FIG. 28.

FIGS. 26-27 depict an alternate illustrative elastomeric insert (400) configured to be used in conjunction with an illustrative end effector and closure ring, including but not limited to end effector (240) and closure ring (270) described above. FIGS. 28-29 depict elastomeric insert (400) positioned on an anvil (460) that is substantially similar to anvil (260) described above. FIGS. 30A-31B depict detailed views of an end effector (440) comprising elastomeric insert (400), anvil (460), and closure ring (470) and the interaction between elastomeric insert (400), anvil (460) and closure ring (470) when end effector (440) is in a fully closed position and a fully opened position. Closure ring (470) is substantially similar to closure ring (270) described above and includes a tab (472) positioned within an opening (474) similar to tab (272) and opening (274) described above. Except for the addition of elastomeric insert (400), the components of end effector (440) are substantially similar and function substantially similarly to those of end effectors (40, 240) described above. Accordingly, the description of those previously discussed components of end effector (440) will not be repeated here.

As shown in FIGS. 26-31B, elastomeric insert (400) comprises a substantially rectangularly shaped insert comprising an opening (402), a distal flange (404) having a distal surface (406) and a proximal flange (408). Of course, insert (400) may have a variety of alternative shapes, including but not limited to circular, ovular, triangular, etc. In this embodiment, opening (402) is sized and shaped to receive at least a portion of an anvil, such as tab (465) of anvil (460). In particular, in the illustrated embodiment, opening (402) comprises a profile that is substantially different from the profile of tab (465). Specifically, as shown, opening (402) comprises an accordion-shaped or star-shaped profile. As shown, opening (402) is positioned substantially in the center of elastomeric insert (400) between distal flange (404) and proximal flange (408). In other embodiments, the opening (402) may be positioned elsewhere within the body of the insert (e.g., so that the central axis of the opening (402) is substantially off-center relative to the overall dimensions of the insert), provided that the opening is still positioned between a distal flange and a proximal flange. In addition, in the illustrated embodiment, opening (402) extends through the entire thickness of elastomeric insert (400). In other embodiments, the opening may extend through only a portion of the thickness of the insert, provided the opening is still configured to receive at least a portion of a corresponding anvil, such as tab (465) of anvil (460).

Insert (400) may comprise an elastomeric material that is compressible in response to a load being applied to the insert (400). The material of insert (400) may also be conformable to allow insert (400) sufficiently occupy at least a portion of the gap around the components located at an interface of closure ring (470) and anvil (460). In preferred embodiments, insert (400) comprises a material that is suitable and acceptable for use in medical procedures, including surgical procedures of the type described herein. By way of example only, elastomeric insert (400) may comprise santoprene, polyurethane, isoprene, Versaflex GLS 360-135, some other compliant plastic material(s), some other rubber compliant material(s), foam, spring steel, other alloys, and/or any other suitable materials capable of improving the stability of anvil (460) by providing a resistive load sufficient to bias anvil (460) to remain in a fully opened position when anvil (460) is in a fully opened position thereby reducing undesired movement or "flopping" of anvil (460) when anvil (460) is in a fully opened position, while also dampening the closure profile to provide a smooth closure as anvil (460) transitions toward a fully closed position.

As shown in FIGS. 28-29, elastomeric insert (400) is positioned on anvil (460) such that at least a portion of tab (465) of anvil (460) is received within the opening (402) of elastomeric insert (400). Accordingly, distal flange (404) of elastomeric insert (400) is positioned distally relative to tab (465) and proximal flange (408) of elastomeric insert (400) is positioned proximally relative to tab (465). As illustrated by FIGS. 30A-31B, when anvil (460) is assembled together with closure ring (470), elastomeric insert (400) is positioned at an interface between anvil (460) and closure ring (470). Specifically, as shown, distal flange (404) of elastomeric insert (400) is positioned between tab (472) of closure ring (470) and tab (465) of anvil (460).

Similar to anvil (260) described above, during opening and closing, anvil (460) pivots relative to a lower jaw similar to lower jaw (250) described above about an axis that is defined by outwardly extending pins (466), which are similar to pins (266) described above. Pins (466) are configured to interact with openings, such as openings (254), in the lower jaw. Accordingly, similar to anvil (260) described above, the pivot axis of anvil (460) translates along the path defined by the openings in the lower jaw while anvil (460) simultaneously pivots about that axis. In addition or in the alternative, the pivot axis may slide along the openings first, with anvil (460) then pivoting about the pivot axis after the pivot axis has slid a certain distance along the openings. It should be understood that such sliding/translating pivotal movement is encompassed within terms such as "pivot," "pivots," "pivotal," "pivotable," "pivoting," and the like. Of course, some versions may provide pivotal movement of anvil (460) about an axis that remains fixed and does not translate within a slot or channel, etc.

Figure 30A:
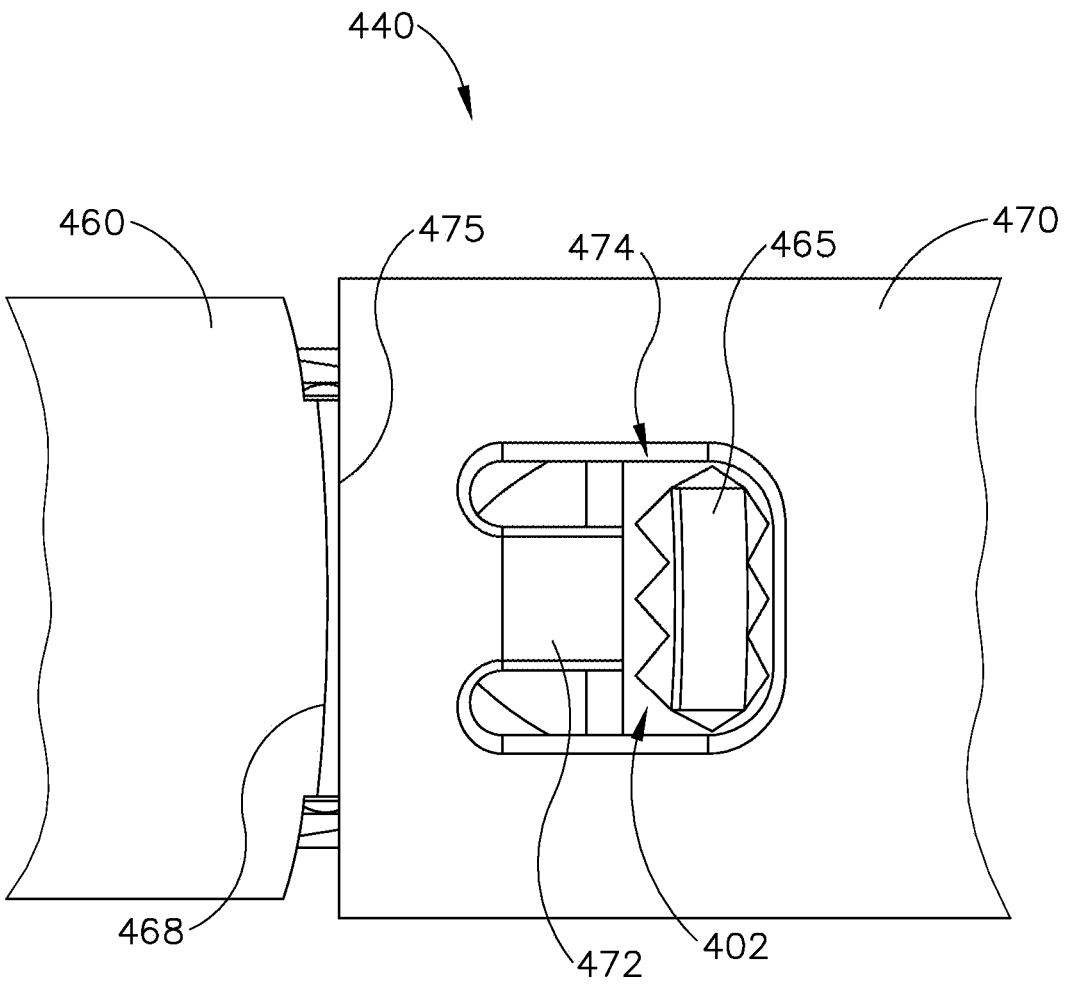
FIG. 30A depicts a detailed top plan view of an illustrative end effector that includes the elastomeric insert and anvil of FIG. 28 when the end effector is fully closed.
Figure 31A:
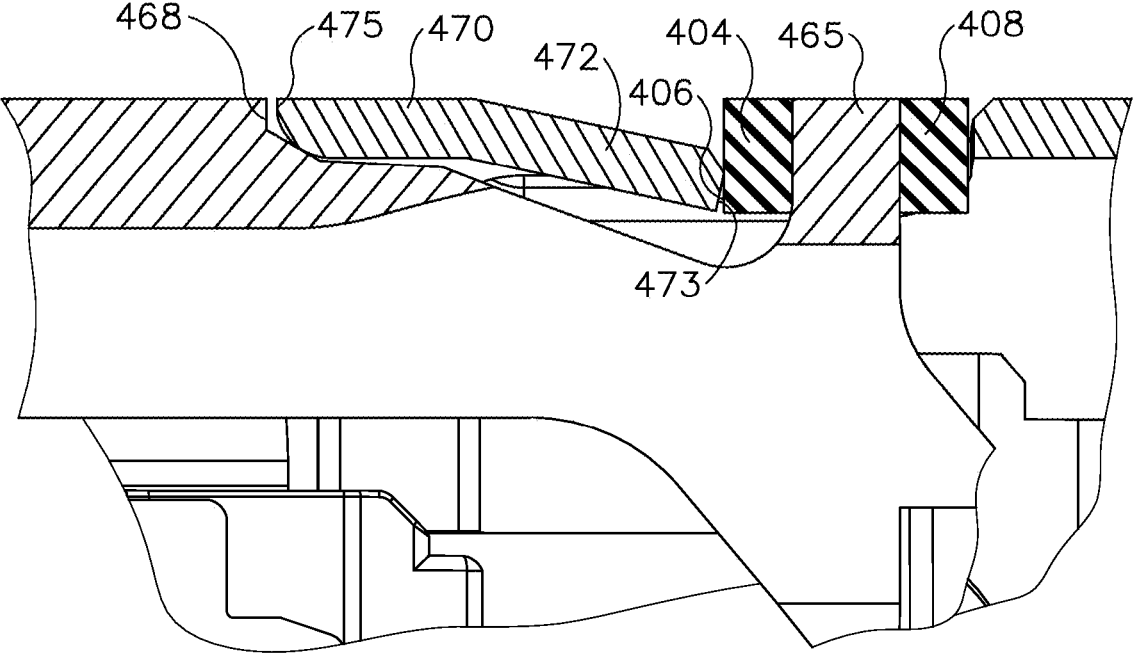
FIG. 31A depicts a detailed cross-sectional side view of the end effector of FIG. 30A when the end effector is fully closed.

FIGS. 30A and 31A depict the interaction between anvil (460) and closure ring (470) when anvil (460) is in a fully closed position. As shown in FIGS. 30A and 31A and as described above with regard to anvil (260) and closure ring (270), when anvil (460) is transitioned toward a fully closed position from a fully opened position and, consequently when anvil (460) is in a fully closed position, the vertical surface (475) of closure ring (470) engages vertical surface (468) of anvil (460) in order to urge anvil (460) distally, which causes anvil (460) to pivot toward a fully closed position, as described above with regard to end effector (240). As anvil (460) transitions from a fully opened position toward a fully closed position, tab (472) of closure ring (470) travels distally relative to tab (465) of anvil (460) before vertical surface (475) of closure ring (470) engages vertical surface (468) of anvil (460), which allows distal flange (404) of elastomeric insert (400) to expand distally to occupy at least a portion of the gap between tab (472) and tab (465). During at least a portion of the closure stroke (i.e., the transition of anvil (460) toward a fully closed position), distal surface (406) of elastomeric insert (400) remains in contact with proximal surface (473) located on the proximal end of tab (472) of closure ring (470). In some embodiments, elastomeric insert (400) is dimensioned such that distal surface (406) of elastomeric insert (400) remains in contact with proximal surface (473) of tab (472) of closure ring (470) during the entire closure stroke. By maintaining contact between elastomeric insert (400) and tab (472) of closure ring (470) during at least a portion of the closure stroke, elastomeric insert (400) is able to provide a force on closure ring (470) that can dampen the closure profile, thereby enabling a smooth closure stroke. The star-shaped profile of opening (402) may result in elastomeric insert (400) providing a substantially different amount of force on closure ring (470) during the closure stroke compared to an elastomeric insert that includes an opening that has a profile that is similar to the corresponding tab that is received within the opening, such as elastomeric insert (300) described above.

In some versions, insert (400) is not formed of elastomeric material. For instance, insert (400) may be formed of spring steel or some other alloy. In some such versions, the star-shaped geometry of the material defining opening (402) may still provide effects on anvil (460) that are similar to effects provided on anvil (460) by an elastomeric insert such as insert (300) described above. For instance, the regions of the spring steel defining opening (402) may deflect yet still bear against tab (465), similar to elastomeric material forming insert (300) described above. In addition to defining a star shape, the regions of the spring steel defining opening (402) may have an accordion-like profile (e.g., bent in a zig-zag formation), which may further promote deformation of those regions.

Figure 30B:
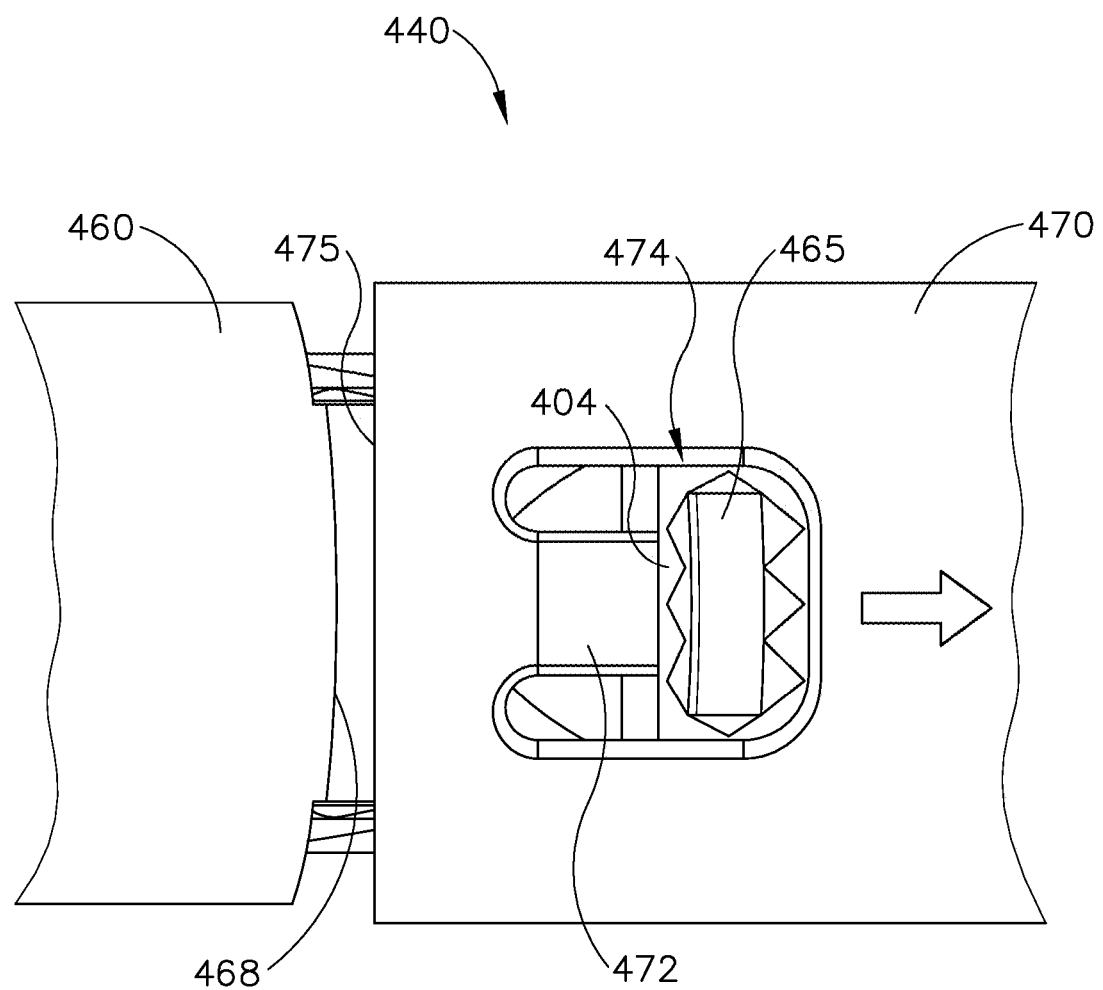
FIG. 30B depicts a detailed top plan view of the end effector of FIG. 30A when the end effector is fully opened.
Figure 31B:
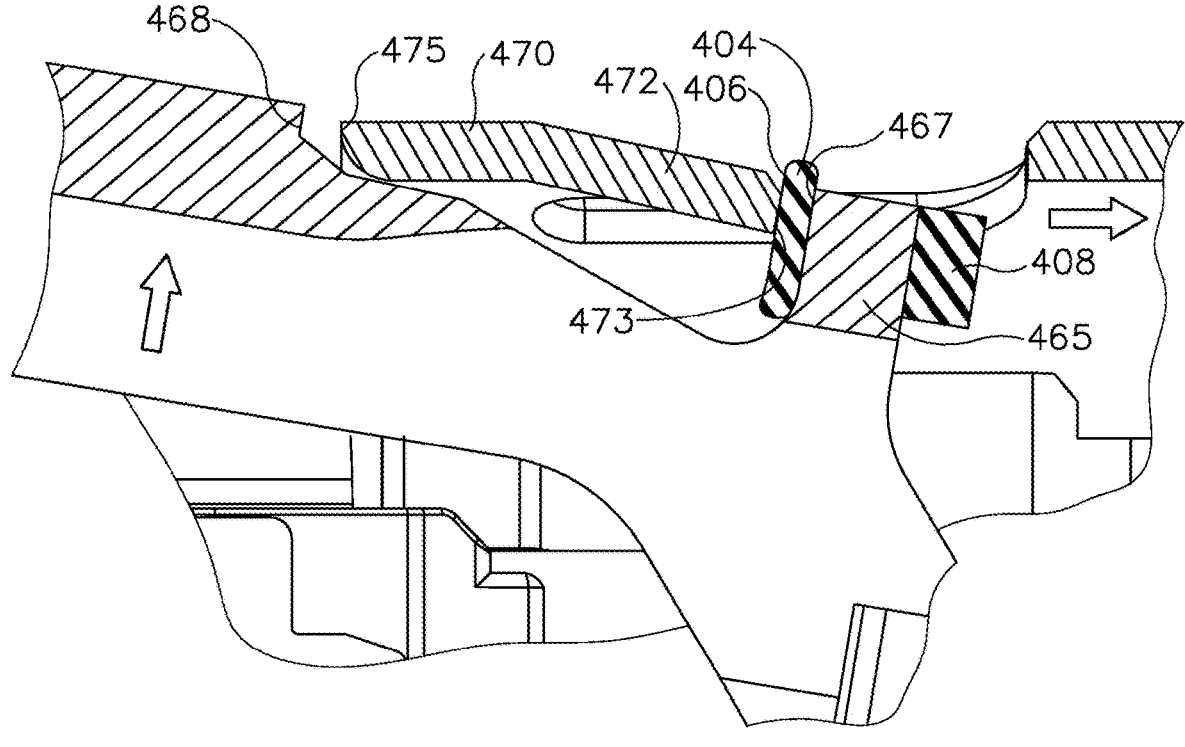
FIG. 31B depicts a detailed cross-sectional side view of the end effector of FIG. 30A when the end effector is fully opened.

Conversely, FIGS. 30B and 31B depict the interaction between anvil (460) and closure ring (470) when anvil (460) is in a fully opened position. As anvil (460) transitions from a fully closed position toward a fully opened position, tab (472) of closure ring (470) travels proximally relative to tab (465) of anvil (460). Accordingly, during at least a portion of the opening stroke (i.e., the transition of anvil (460) toward a fully opened position) elastomeric insert (400) is compressed between closure ring (470) and anvil (460). In some embodiments, elastomeric insert (400) is dimensioned such that distal surface (406) of elastomeric insert (400) is in contact with proximal surface (473) of tab (472) of closure ring (470) during the entire opening stroke. Specifically, as tab (472) of closure ring (470) travels toward tab (465) of anvil (460), distal flange (404) of elastomeric insert (400) is compressed between proximal surface (473) of tab (472) and distal surface (467) of tab (465). As a result of this compression, when anvil (460) is in a fully opened position, elastomeric insert (400) improves the stability of anvil (460) by providing a resistive load on anvil (460) sufficient to bias anvil (460) to remain in the fully opened position thereby reducing undesired movement or "flopping" of anvil (460) when anvil (460) is in the fully opened position. It will be understood that the resistive load provided by elastomeric insert (400) is able to be overcome during a closure stroke of anvil (460) such that anvil (460) is pivotable to a fully closed position. In conjunction with the compression of elastomeric insert (400), closure ring (470) also engages tab (465) through elastomeric insert (400) and drives anvil (460) proximally, thereby causing anvil (460) to pivot toward the fully opened position, as described above with regard to end effector (240). The star-shaped profile of opening (402) may result in elastomeric insert (400) providing a substantially different amount of force on anvil (460) during the opening stroke compared to an elastomeric insert that includes an opening that has a profile that is similar to the corresponding tab received within the opening, such as elastomeric insert (300) described above. As noted above, even in versions where insert (400) is not formed of an elastomeric material, the star-shaped geometry of the material defining opening (402) may still provide these same effects on anvil (460).

C. Illustrative Anvil with Layer of Elastomeric Material

Figure 32:
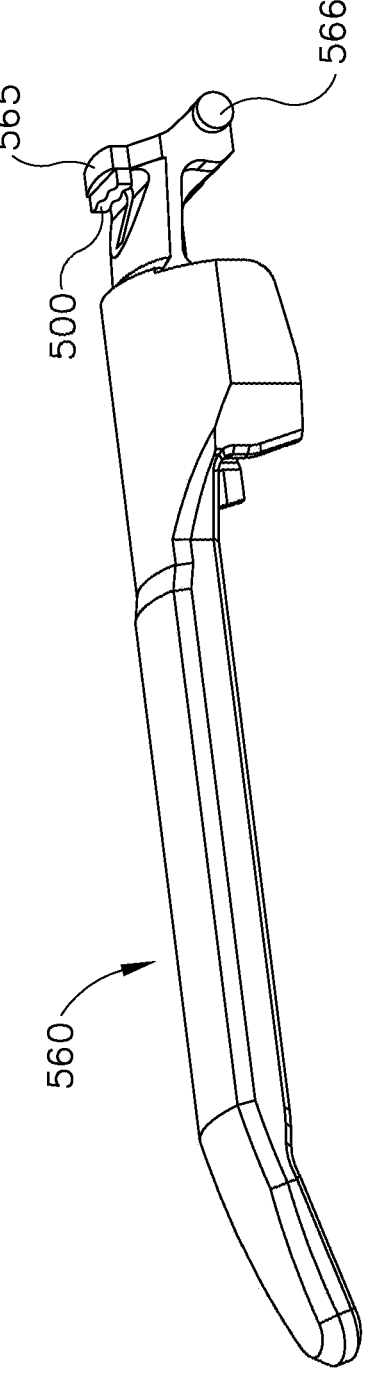
FIG. 32 depicts a side elevational view of an illustrative anvil with an elastomeric layer attached thereto.
Figure 33:
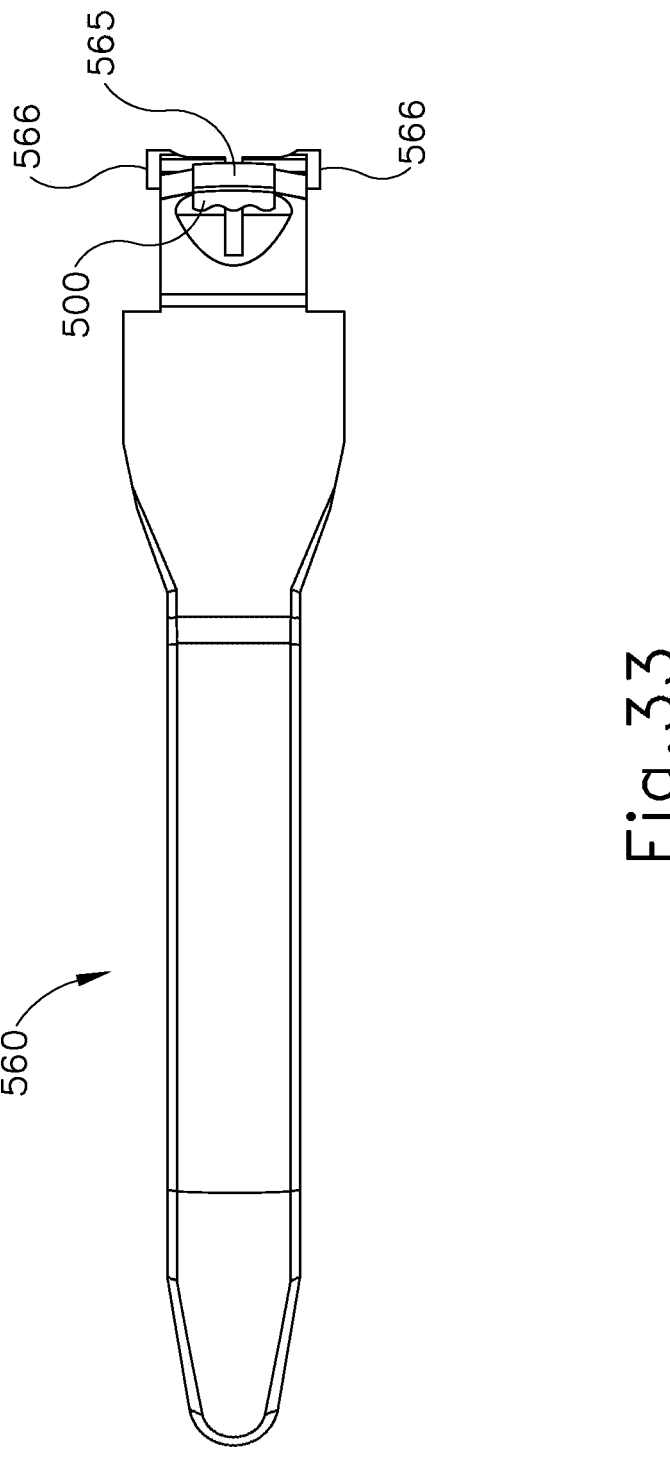
FIG. 33 depicts a top plan view of the anvil of FIG. 32.

FIGS. 32-33 depict an illustrative layer of elastomeric material (500) configured to be used in conjunction with an illustrative end effector and closure ring, including but not limited to end effector (240) and closure ring (270) described above. In the illustrated embodiment, elastomeric layer (500) is positioned on an anvil (560) that is substantially similar to anvil (260) described above. FIGS. 34A-35B depict detailed views of an end effector (540) comprising elastomeric layer (500), anvil (560), and closure ring (570) and the interaction between elastomeric layer (500), anvil (560) and closure ring (570) when end effector (540) is in a fully closed position and a fully opened position. Closure ring (570) is substantially similar to closure ring (270) described above and includes a tab (572) positioned within an opening (574) similar to tab (272) and opening (274) described above. Except for the addition of elastomeric layer (500), the components of end effector (540) are substantially similar and function substantially similarly to those of end effectors (40, 240) described above. Accordingly, the description of those previously discussed components of end effector (540) will not be repeated here.

As shown in FIGS. 32-35B, elastomeric layer (500) comprises a layer of elastomeric material applied to tab (565) of anvil (560). Specifically, in the illustrated embodiment, elastomeric layer (500) is applied to distal surface (567) of tab (565). As shown, elastomeric layer (500) is substantially coextensive with distal surface (567). It will be appreciated that in some embodiments, elastomeric layer (500) may cover only a portion of distal surface (567) of tab (565), provided that a sufficient amount of elastomeric material is provided and a sufficient amount of distal surface (567) is covered to improve the stability of anvil (560) by providing a resistive load on anvil (560) sufficient to bias anvil (560) to remain in a fully opened position when anvil (560) is in a fully opened position thereby reducing undesired movement or "flopping" of anvil (560) when anvil (560) is in a fully opened position. Elastomeric layer (500) may be attached to tab (565) of anvil (560) using any suitable devices or methods, including but not limited to applying an adhesive between elastomeric layer (500) and tab (565), insert molding elastomeric layer (500) into tab (565) (which may include providing an opening in tab (565) similar to opening (671) in tab (672) described below), and overmolding elastomeric layer (500) onto tab (565).

Elastomeric layer (500) may comprise an elastomeric material that is compressible in response to a load being applied to the layer (500). The material of layer (500) may also be conformable to allow layer (500) to sufficiently occupy at least a portion of the gap around the components located at an interface of closure ring (570) and anvil (560). In preferred embodiments, layer (500) comprises a material that is suitable and acceptable for use in medical procedures, including surgical procedures of the type described herein. By way of example only, elastomeric layer (500) may comprise santoprene, polyurethane, isoprene, Versaflex GLS 360-135, some other compliant plastic material(s), some other rubber compliant material(s), foam, and/or any other suitable materials capable of improving the stability of anvil (560) by providing a resistive load sufficient to bias anvil (560) to remain in a fully opened position when anvil (560) is in a fully opened position thereby reducing undesired movement or "flopping" of anvil (560) when anvil (560) is in a fully opened position.

As shown in FIGS. 32-33, elastomeric layer (500) is positioned on anvil (560) such that elastomeric layer (500) is positioned distally relative to tab (565). As illustrated by FIGS. 34A-35B, when anvil (560) is assembled together with closure ring (570), elastomeric layer (500) is positioned at an interface between anvil (560) and closure ring (570). Specifically, as shown, elastomeric layer (500) is positioned between tab (572) of closure ring (570) and tab (565) of anvil (560).

Similar to anvil (260) described above, during opening and closing, anvil (560) pivots relative to a lower jaw similar to lower jaw (250) described above about an axis that is defined by pins (566), which are similar to pins (266) described above. Pins (566) are configured to interact with openings, such as openings (254), in the lower jaw. Accordingly, similar to anvil (260) described above, the pivot axis of anvil (560) translates along the path defined by the openings in the lower jaw while anvil (560) simultaneously pivots about that axis. In addition or in the alternative, the pivot axis may slide along the openings first, with anvil (560) then pivoting about the pivot axis after the pivot axis has slid a certain distance along the openings. It should be understood that such sliding/translating pivotal movement is encompassed within terms such as "pivot," "pivots," "pivotal," "pivotable," "pivoting," and the like. Of course, some versions may provide pivotal movement of anvil (560) about an axis that remains fixed and does not translate within a slot or channel, etc.

Figure 34A:
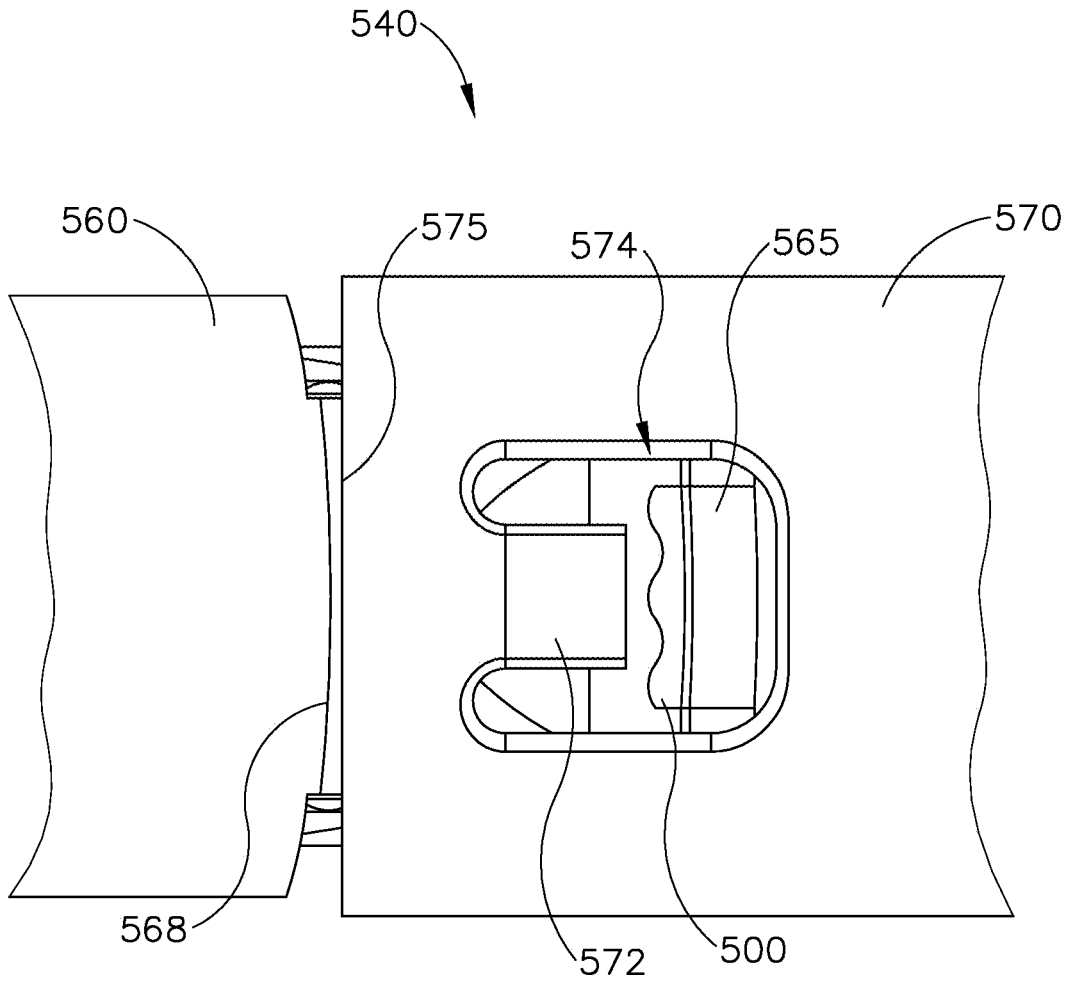
FIG. 34A depicts a detailed top plan view of an illustrative end effector that includes the anvil of FIG. 32 when the end effector is fully closed.
Figure 35A:
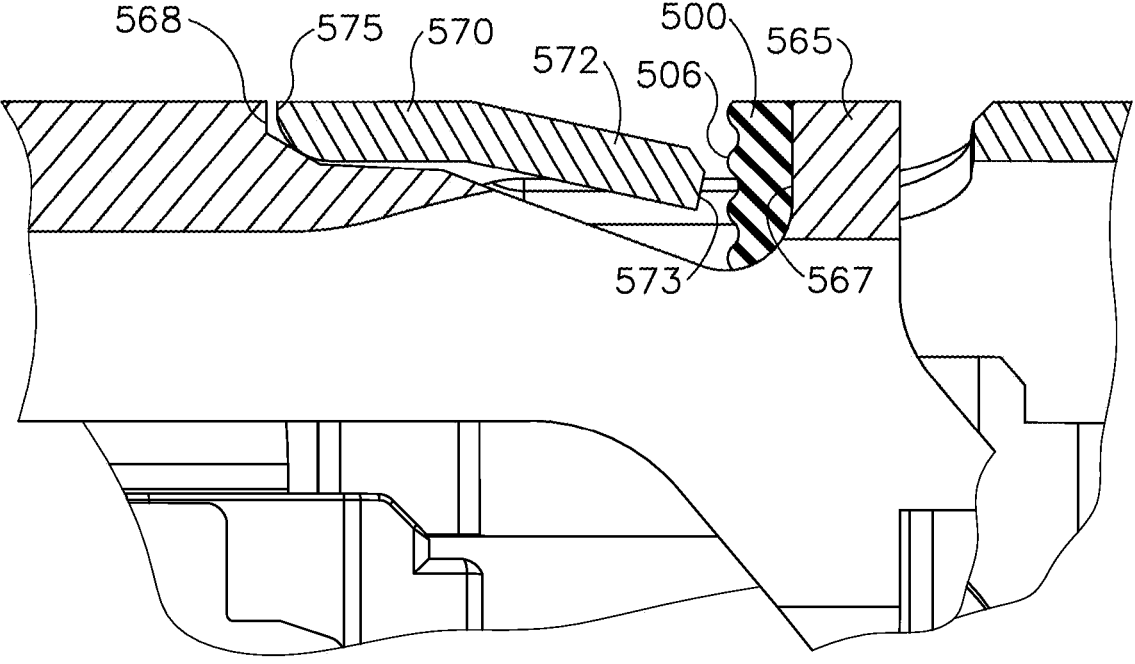
FIG. 35A depicts a detailed cross-sectional side view of the end effector of FIG. 34A when the end effector is fully closed.

FIGS. 34A and 35A depict the interaction between anvil (560) and closure ring (570) when anvil (560) is in a fully closed position. As shown in FIGS. 34A and 35A and as described above with regard to anvil (260) and closure ring (270), when anvil (560) is transitioned toward a fully closed position from a fully opened position and, consequently when anvil (560) is in a fully closed position, the vertical surface (575) of closure ring (570) engages vertical surface (568) of anvil (560) in order to urge anvil (560) distally, which causes anvil (560) to pivot toward a fully closed position, as described above with regard to end effector (240). As anvil (560) transitions from a fully opened position toward a fully closed position, tab (572) of closure ring (570) travels distally relative to tab (565) of anvil (560) before vertical surface (575) of closure ring (570) engages vertical surface (568) of anvil (560), which allows elastomeric layer (500) to expand distally to occupy at least a portion of the gap between tab (572) and tab (565). During at least a portion of the closure stroke (i.e., the transition of anvil (560) toward a fully closed position), distal surface (506) of elastomeric layer (500) remains in contact with proximal surface (573) located on the proximal end of tab (572) of closure ring (570). In some embodiments, elastomeric layer (500) is dimensioned such that distal surface (506) of elastomeric layer (500) remains in contact with proximal surface (573) of tab (572) of closure ring (570) during the entire closure stroke. By maintaining contact between elastomeric layer (500) and tab (572) of closure ring (570) during at least a portion of the closure stroke, elastomeric layer (500) is able to provide a force on closure ring (570) that can dampen the closure profile, thereby enabling a smooth closure stroke. In some versions, elastomeric layer (500) is formed of a material with lubricious properties, and/or elastomeric layer (500) is treated with a lubricant, to further provide a smooth closure stroke of anvil (560) during distal advancement of closure ring (570).

Figure 34B:
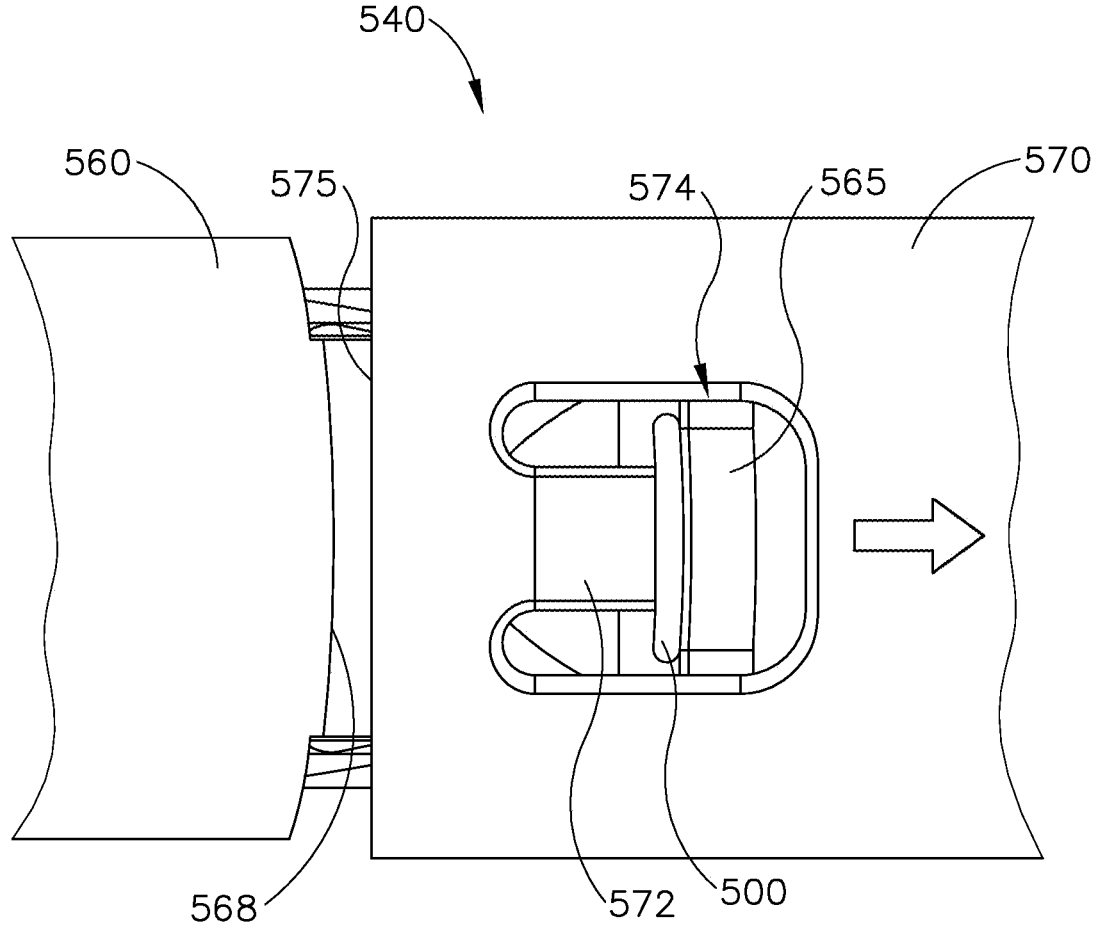
FIG. 34B depicts a detailed top plan view of the end effector of FIG. 34A when the end effector is fully opened.
Figure 35B:
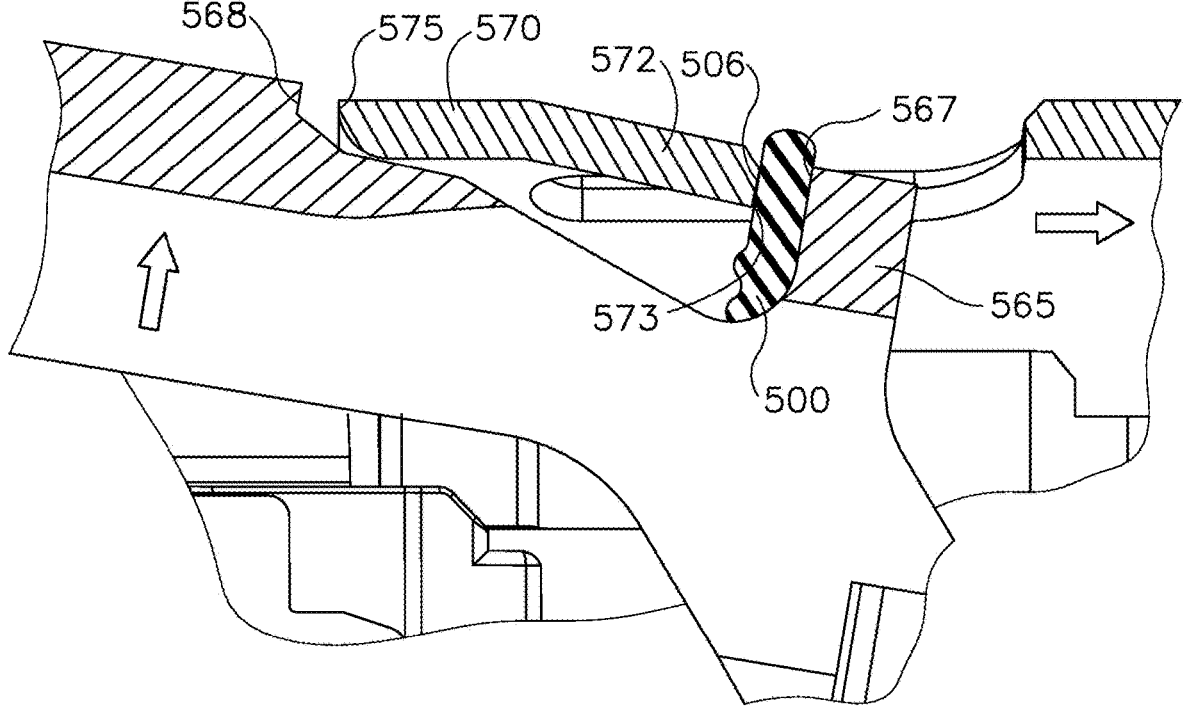
FIG. 35B depicts a detailed cross-sectional side view of the end effector of FIG. 34A when the end effector is fully opened.

Conversely, FIGS. 34B and 35B depict the interaction between anvil (560) and closure ring (570) when anvil (560) is in a fully opened position. As anvil (560) transitions from a fully closed position toward a fully opened position, tab (572) of closure ring (570) travels proximally relative to tab (565) of anvil (560). Accordingly, during at least a portion of the opening stroke (i.e., the transition of anvil (560) toward a fully opened position) elastomeric layer (500) is compressed between closure ring (570) and anvil (560). In some embodiments, elastomeric layer (500) is dimensioned such that distal surface (506) of elastomeric layer (500) is in contact with proximal surface (573) of tab (572) of closure ring (570) during the entire opening stroke. Specifically, as tab (572) of closure ring (570) travels toward tab (565) of anvil (560), elastomeric layer (500) is compressed between proximal surface (573) of tab (572) and distal surface (567) of tab (565). As a result of this compression, when anvil (560) is in a fully opened position, elastomeric layer (500) improves the stability of anvil (560) by providing a resistive load on anvil (560) sufficient to bias anvil (560) to remain in a fully opened position thereby reducing undesired movement or "flopping" of anvil (560) when anvil (560) is in a fully opened position. It will be understood that the resistive load provided by elastomeric layer (500) is able to be overcome during a closure stroke of anvil (560) such that anvil (560) is pivotable to a fully closed position. In conjunction with the compression of elastomeric layer (500), closure ring (570) also engages tab (565) through elastomeric layer (500) and drives anvil (560) proximally, thereby causing anvil (560) to pivot toward the fully opened position, as described above with regard to end effector (240). In some versions, a ribbed or ridged surface profile of distal surface (506) may provide a ratcheting feature during opening of anvil (560) and/or may provide further security to the open position of anvil (560). In other words, one or more ribs or ridges on distal surface (506) may further engage tab (572) to assist in holding anvil (560) in an open position. Alternatively, distal surface (506) may be flat or have any other suitable surface properties.

D. Illustrative Closure Ring with Layer of Elastomeric Material

Figure 36:
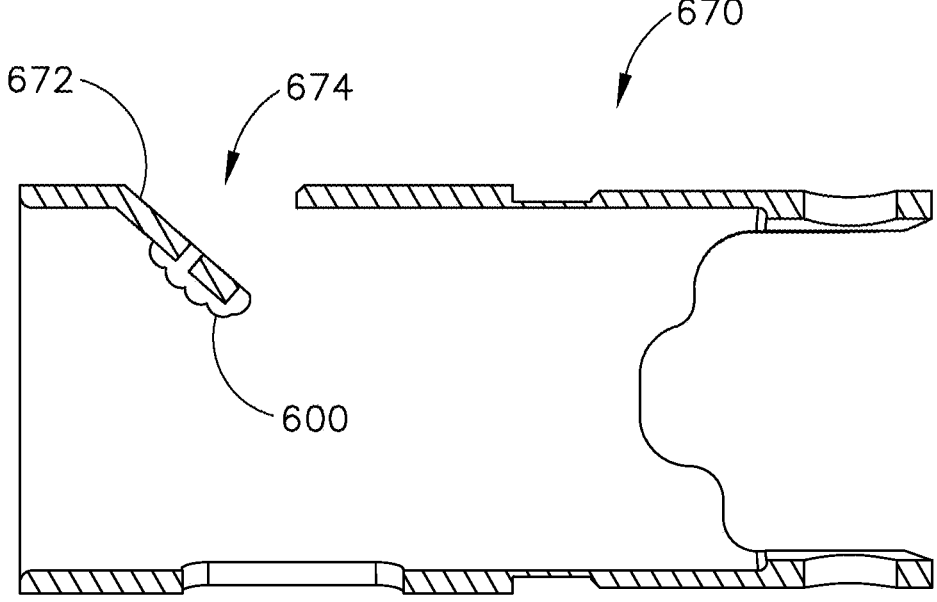
FIG. 36 depicts a cross-sectional side view of an illustrative closure ring with an elastomeric layer attached thereto.

FIG. 36 depicts an alternate illustrative layer of elastomeric material (600) configured to be used in conjunction with an illustrative end effector and closure ring, including but not limited to end effector (240) and closure ring (270) described above. In the illustrated embodiment, elastomeric layer (600) is positioned on a closure ring (670) that is substantially similar to closure ring (270) described above and includes a tab (672) positioned within an opening (674) similar to tab (272) and opening (274) described above. FIGS. 37A-38B depict detailed views of an end effector (640) comprising elastomeric layer (600), anvil (660), which is substantially similar to anvil (260) described above, and closure ring (670) and the interaction between elastomeric layer (600), anvil (660), and closure ring (670) when end effector (640) is in a fully closed position and a fully opened position.

As shown in FIGS. 36-38B, elastomeric layer (600) comprises a layer of elastomeric material applied to tab (672) of closure ring (670). Specifically, in the illustrated embodiment, elastomeric layer (600) is applied to proximal surface (673) of tab (672) and a portion of bottom surface (676) of tab (672). As shown, elastomeric layer (600) is substantially coextensive with proximal surface (673). It will be appreciated that in some embodiments, elastomeric layer (600) may cover only a portion of proximal surface (673) of tab (672) and/or may be limited to just proximal surface (673) instead of being applied to both proximal surface (673) and a portion of bottom surface (676), provided that a sufficient amount of elastomeric material is provided and a sufficient amount of proximal surface (673) is covered to improve the stability of anvil (660) by providing a resistive load on anvil (660) sufficient to bias anvil (660) to remain in a fully opened position when anvil (660) is in a fully opened position thereby reducing undesired movement or "flopping" of anvil (660) when anvil (660) is in a fully opened position. Elastomeric layer (600) may be attached to tab (672) of closure ring (670) using any suitable devices or methods, including but not limited to applying an adhesive between elastomeric layer (600) and tab (672), insert molding elastomeric layer (600) into tab (672), and overmolding elastomeric layer (600) onto tab (672). As shown, closure ring (670) includes an opening (671) in tab (672) configured to allow elastomeric layer (600) to be insert molded into tab (672). In other embodiments, particularly those where the elastomeric layer is attached to the tab of the closure ring using a device or method other than insert molding, such as adhesive, the opening in the tab may be omitted.

Elastomeric layer (600) may comprise an elastomeric material that is compressible in response to a load being applied to the layer (600). The material of layer (600) may also be conformable to allow layer (600) to sufficiently occupy at least a portion of the gap around the components located at an interface of closure ring (670) and anvil (660). In preferred embodiments, layer (600) comprises a material that is suitable and acceptable for use in medical procedures, including surgical procedures of the type described herein. By way of example only, elastomeric layer (600) may comprise santoprene, polyurethane, isoprene, Versaflex GLS 360-135, some other compliant plastic material(s), some other rubber compliant material(s), foam, and/or any other suitable materials capable of improving the stability of anvil (660) by providing a resistive load sufficient to bias the anvil to remain in a fully opened position when anvil (660) is in a fully opened position thereby reducing undesired movement or "flopping" of anvil (660) when anvil (660) is in a fully opened position.

As shown in FIG. 36, elastomeric layer (600) is positioned on closure ring (670) such that elastomeric layer (600) is positioned distally relative to tab (672). As illustrated by FIGS. 37A-38B, when anvil (660) is assembled together with closure ring (670), elastomeric layer (600) is positioned at an interface between anvil (660) and closure ring (670). Specifically, as shown, elastomeric layer (600) is positioned between tab (672) of closure ring (670) and tab (665) of anvil (660).

Figure 37A:
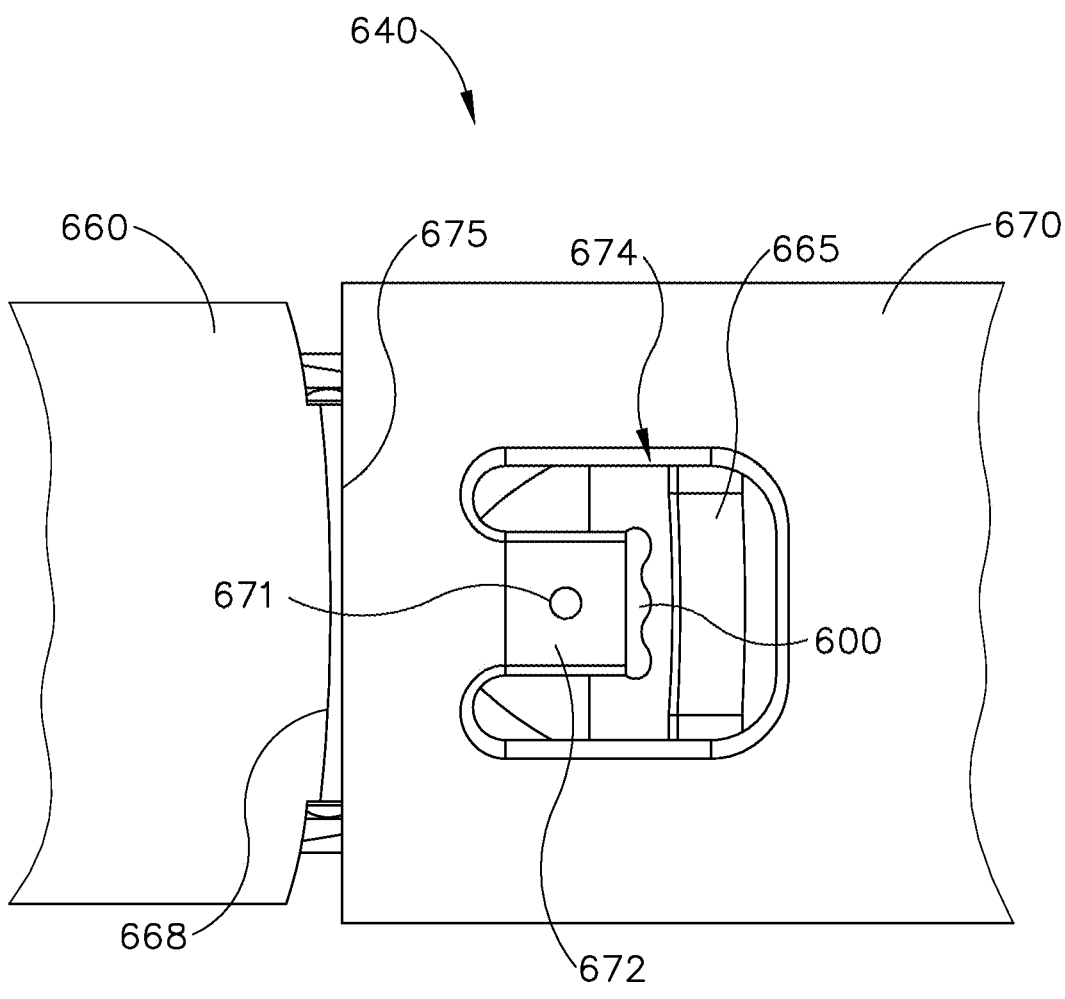
FIG. 37A depicts a detailed top plan view of an illustrative end effector that includes the closure ring of FIG. 36 when the end effector is fully closed.
Figure 38A:
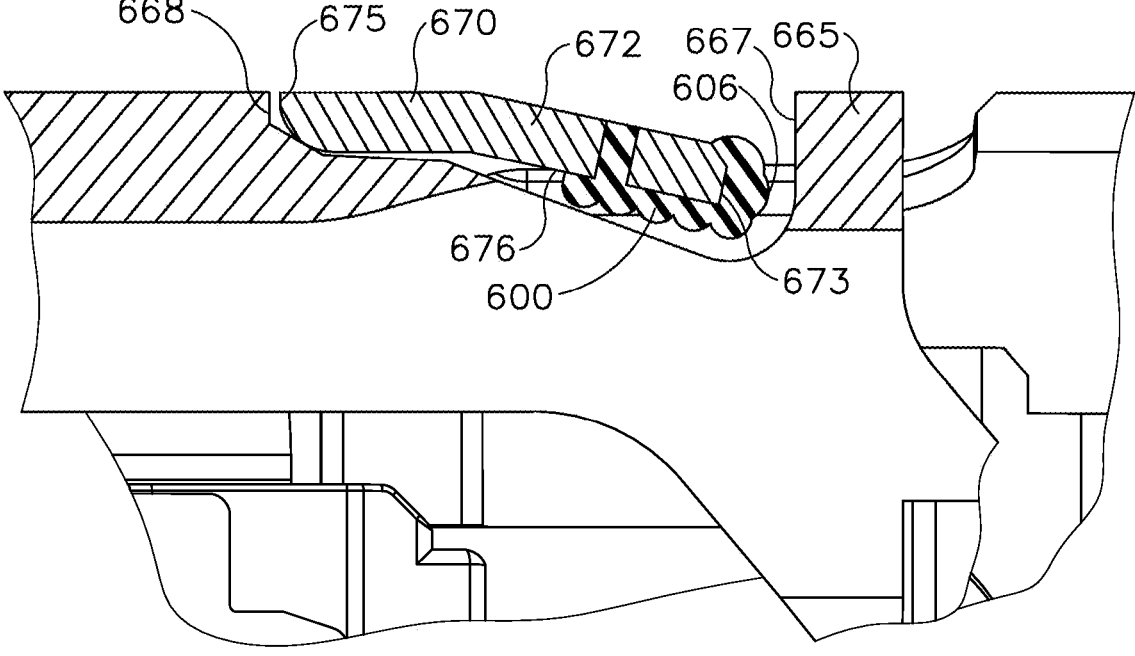
FIG. 38A depicts a detailed cross-sectional side view of the end effector of FIG. 37A when the end effector is fully closed.

FIGS. 37A and 38A depict the interaction between anvil (660) and closure ring (670) when anvil (660) is in a fully closed position. As shown in FIGS. 37A and 38A and as described above with regard to anvil (260) and closure ring (270), when anvil (660) is transitioned toward a fully closed position from a fully opened position and, consequently when anvil (660) is in a fully closed position, the vertical surface (675) of closure ring (670) engages vertical surface (668) of anvil (660) in order to urge anvil (660) distally, which causes anvil (660) to pivot toward a fully closed position, as described above with regard to end effector (240). As anvil (660) transitions from a fully opened position toward a fully closed position, tab (672) of closure ring (670) travels distally relative to tab (665) of anvil (660) before vertical surface (675) of closure ring (670) engages vertical surface (668) of anvil (660), which allows elastomeric layer (600) to expand proximally to occupy at least a portion of the gap between tab (672) and tab (665). During at least a portion of the closure stroke (i.e., the transition of anvil (660) toward a fully closed position), proximal surface (606) of elastomeric layer (600) remains in contact with distal surface (667) of tab (665). In some embodiments, elastomeric layer (600) is dimensioned such that proximal surface (606) of elastomeric layer (600) remains in contact with distal surface (667) of tab (665) of anvil (660) during the entire closure stroke. By maintaining contact between elastomeric layer (600) and tab (665) of anvil (660) during at least a portion of the closure stroke, elastomeric layer (600) is able to provide a force on anvil (660) that can dampen the closure profile, thereby enabling a smooth closure stroke. In some versions, elastomeric layer (600) is formed of a material with lubricious properties, and/or elastomeric layer (600) is treated with a lubricant, to further provide a smooth closure stroke of anvil (660) during distal advancement of closure ring (670).

Figure 37B:
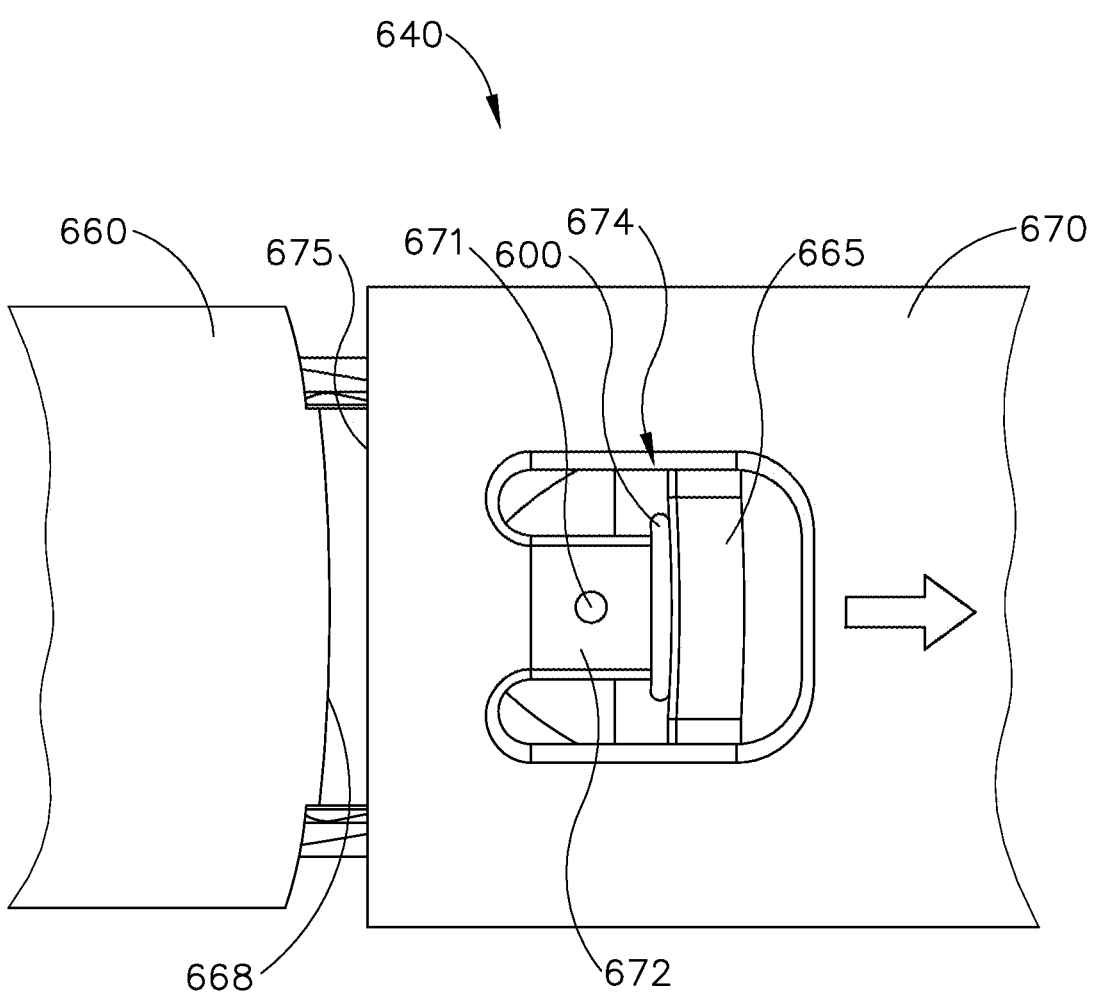
FIG. 37B depicts a detailed top plan view of the end effector of FIG. 37A when the end effector is fully opened.
Figure 38B:
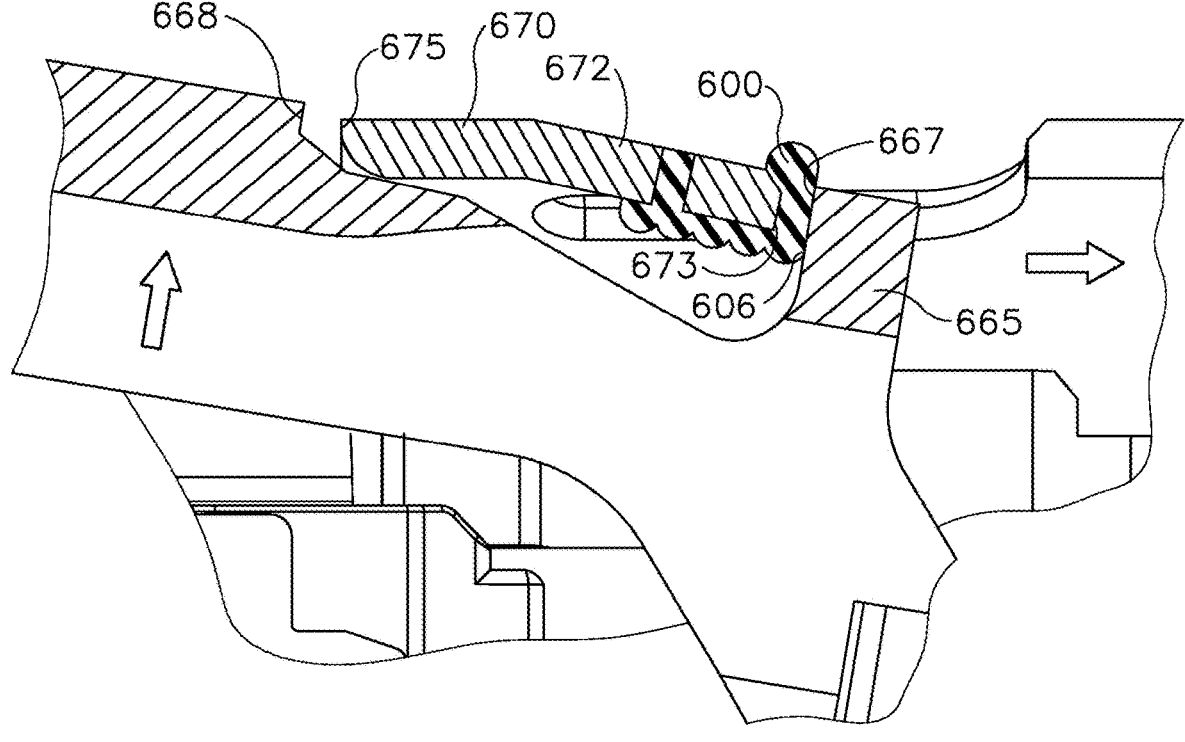
FIG. 38B depicts a detailed cross-sectional side view of the end effector of FIG. 37A when the end effector is fully opened.

Conversely, FIGS. 37B and 38B depict the interaction between anvil (660) and closure ring (670) when anvil (660) is in a fully opened position. As anvil (660) transitions from a fully closed position toward a fully opened position, tab (672) of closure ring (670) travels proximally relative to tab (665) of anvil (660). Accordingly, during at least a portion of the opening stroke (i.e., the transition of anvil (660) toward a fully opened position) elastomeric layer (600) is compressed between closure ring (670) and anvil (660). In some embodiments, elastomeric layer (600) is dimensioned such that proximal surface (606) of elastomeric layer (600) is in contact with distal surface (667) of tab (665) of closure ring (670) during the entire opening stroke. Specifically, as tab (672) of closure ring (670) travels toward tab (665) of anvil (660), elastomeric layer (600) is compressed between proximal surface (673) of tab (672) and distal surface (667) of tab (665). As a result of this compression, when anvil (660) is in a fully opened position, elastomeric layer (600) improves the stability of anvil (660) by providing a resistive load on anvil (660) sufficient to bias anvil (660) to remain in a fully opened position thereby reducing undesired movement or "flopping" of anvil (660) when anvil (660) is in a fully opened position. It will be understood that the resistive load provided by elastomeric layer (600) is able to be overcome during a closure stroke of anvil (660) such that anvil (660) is pivotable to a fully closed position. In conjunction with the compression of elastomeric layer (600), closure ring (670) also engages tab (665) through elastomeric layer (600) and drives anvil (660) proximally, thereby causing anvil (660) to pivot toward the fully opened position, as described above with regard to end effector (240). In some versions, elastomeric layer (600) has a ridged or ribbed surface profile, similar to layer (500) described above. Alternatively, elastomeric layer (600) may have a smooth surface profile or any other suitable kind of surface profile.

E. Illustrative End Effector with Torsion Springs

Figure 39:
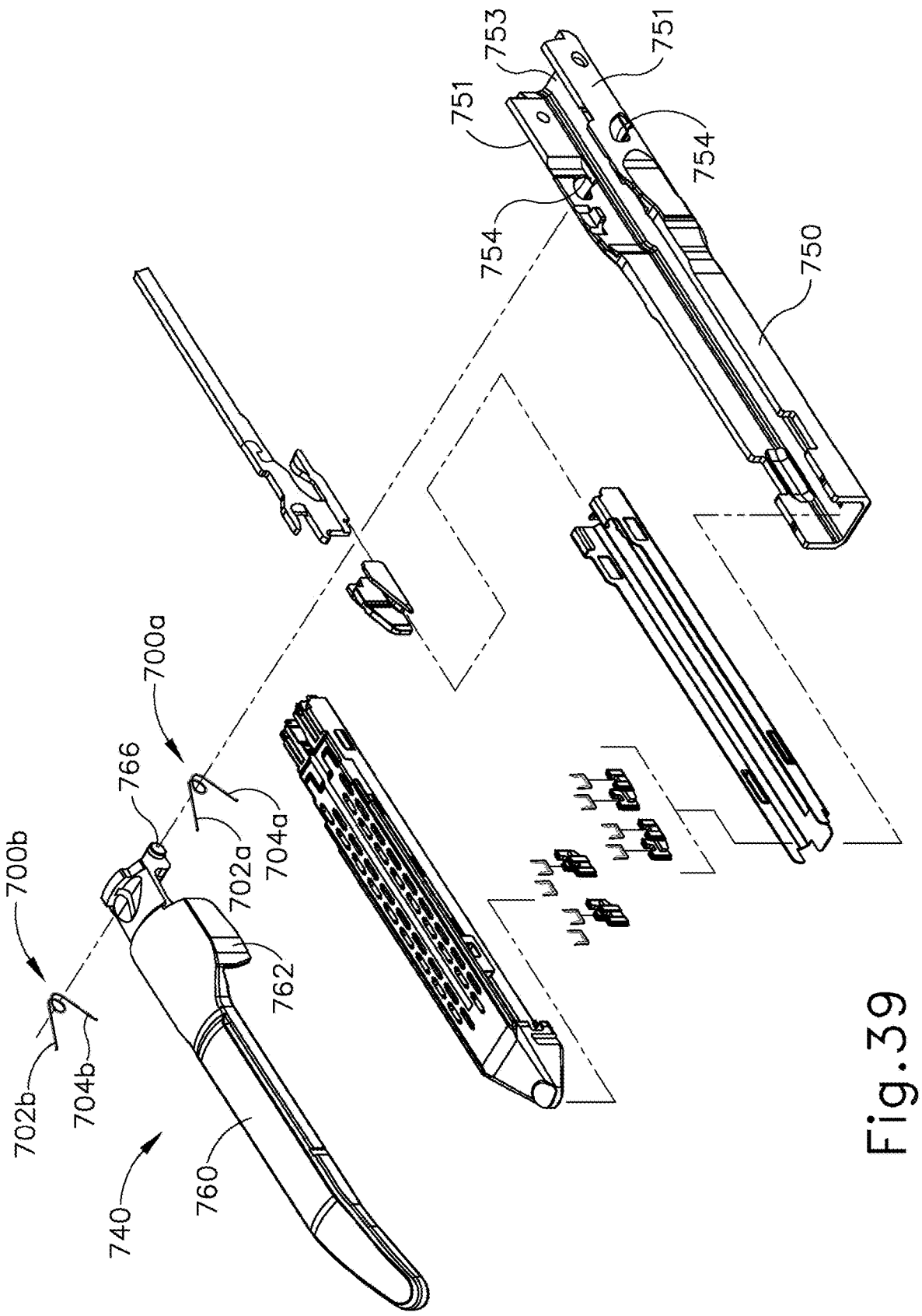
FIG. 39 depicts an exploded perspective view of an illustrative end effector that includes a pair of springs.
Figure 40:
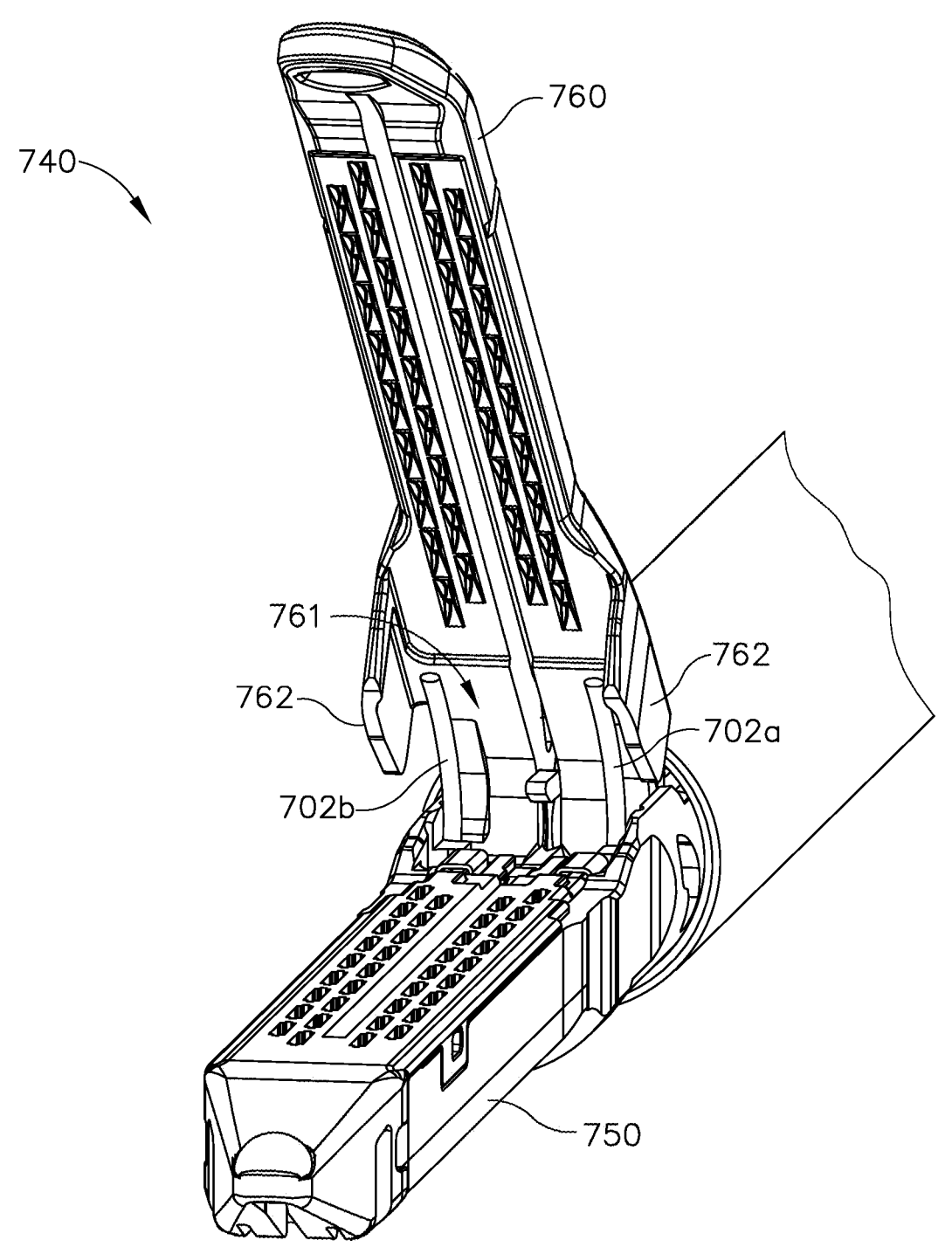
FIG. 40 depicts a perspective view of the end effector of FIG. 39 in an open position.
Figure 41A:
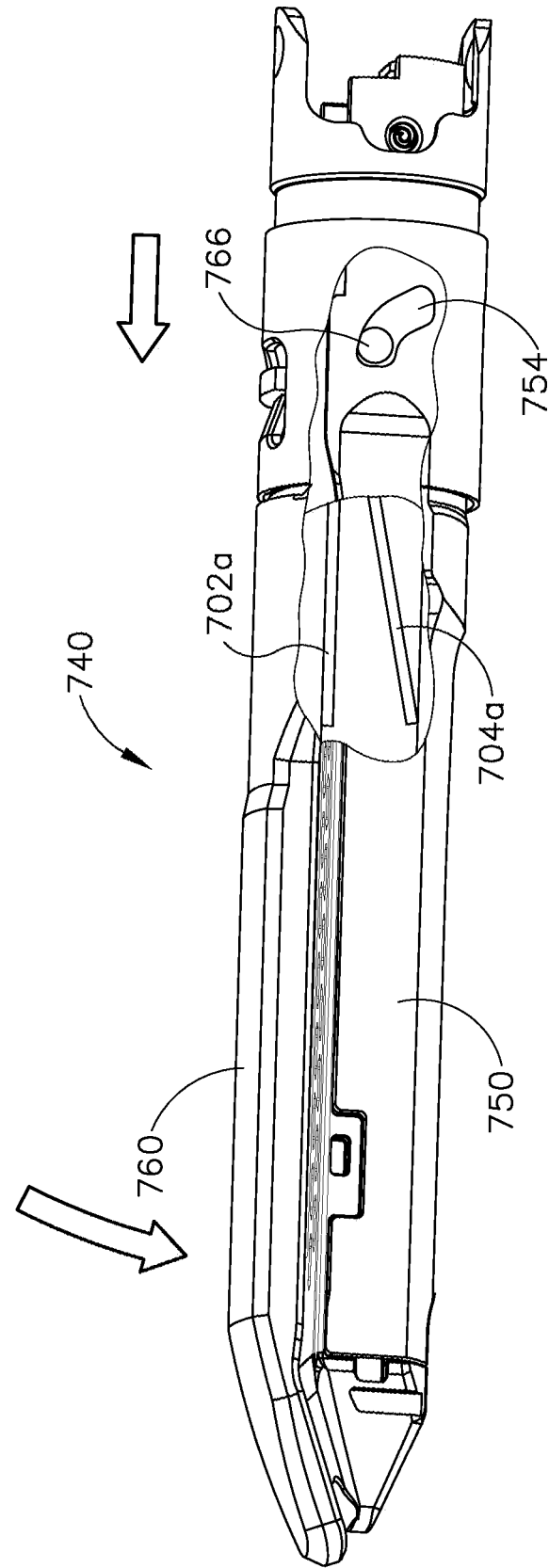
FIG. 41A depicts a perspective view of the end effector of FIG. 39 fully closed with a portion of the end effector removed to reveal the springs and other internal structures.
Figure 41B:
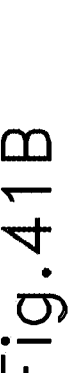
FIG. 41B depicts a perspective view of the end effector of FIG. 39 fully opened with a portion of the end effector removed to reveal the springs and other internal structures.

FIG. 39 depicts an illustrative resilient member comprising a pair of springs (700a, 700b) configured to be used in conjunction with an illustrative end effector, including but not limited to end effector (240) described above. In the illustrated embodiment, springs (700a, 700b) are positioned on an anvil (760) that is substantially similar to anvil (260) described above. FIGS. 40-41B depict different views of the interaction between springs (700a, 700b), anvil (760), and lower jaw (750), which is substantially similar to lower jaw (50) described above, when anvil (760) is in a fully closed position and a fully opened position. By way of example only, springs (700a, 700b) may be formed of spring steel, such as stainless spring steel strip in type 301 and type 420; or some other alloy. Alternatively, any other suitable material(s) may be used to form springs (700a, 700b).

FIGS. 39-41B depict end effector (740), which is substantially similar to end effectors (40, 240) described above. Except for the addition of springs (700a, 700b), the components of end effector (740) are substantially similar and function substantially similarly to those of end effectors (40, 240) described above. Accordingly, the description of those previously discussed components of end effector (740) will not be repeated here. Although the illustrated embodiment depicts a pair of springs (700a, 700b), which allows springs (700a, 700b) to provide a biasing force evenly on both sides of anvil (760), it will be appreciated that other embodiments may include any suitable number of springs, including one spring or three or more springs.

In the illustrated embodiment, each spring (700a, 700b) comprises an upper leg (702a, 702b) and a lower leg (704a, 704b). Springs (700a, 700b) are configured such that upper legs (702a, 702b) are angularly biased away from lower legs (704a, 704b) when springs (700a, 700b) are in an uncompressed state. Springs (700a, 700b) may be configured such that upper legs (702a, 702b) extend at an acute angle relative to lower legs (704a, 704b) when springs (700a, 700b) are in an uncompressed state. As shown, springs (700a, 700b) are positioned relative to anvil (760) such that upper leg (702a, 702b) of each respective spring (700a, 700b) engages and bears against anvil (760) and lower leg (704a, 704b) engages and bears against lower jaw (750). Specifically, each of the upper legs (702a, 702b) are positioned to the interior of flanges (762) so that they contact the interior surface (761) of anvil (760), while each of the lower legs (704a, 704b) are positioned to the interior of sidewalls (751) so that they contact the bottom surface (753) of lower jaw (750). Of course, upper legs (702a, 702b) may contact any suitable region of anvil (760) and/or any other component that is secured to anvil (760). Similarly, lower legs (704a, 704b) may contact any other region of lower jaw (750) and/or any other component that is secured to lower jaw (750). It should also be understood that any other suitable kind of spring(s) may be used, including but not limited to a cantilever spring that is mounted to anvil (760), lower jaw (750), or a cartridge disposed in lower jaw.

As shown, the interior surface (761) comprises the surface on the underside of anvil (760) that extends between the outer flanges (762) of anvil (760). Accordingly, springs (700a, 700b), apply angularly outwardly oriented forces on anvil (760) and lower jaw (750) that bias anvil (760) toward a fully opened position. As shown, springs (700a, 700b) are each positioned about a respective outwardly extending pin (766) of anvil (760), which are substantially similar to outwardly extending pins (66, 266) described above. In the illustrated embodiment, springs (700a, 700b) comprise helical torsion springs where at least a portion of the coil of each spring (700a, 700b) is positioned around a respective pin (766). Springs (700a, 700b) may be positioned about pins (766) between anvil (760) and the inner surface of the corresponding side wall (751) of lower jaw (750) when anvil (760) and lower jaw (750) are assembled together.

Springs (700a, 700b) are configured to provide a resistive load sufficient to bias anvil (760) to remain in a fully opened position when anvil (760) is in a fully opened position thereby reducing undesired movement or "flopping" of anvil (760) when anvil (760) is in a fully opened position. Springs (700a, 700b) may be configured to provide a substantially constant force on anvil (760) that biases anvil (760) toward a fully opened position by remaining in substantially constant contact with anvil (760). In addition, as illustrated by FIG. 41A, the resistive load provided by springs (700a, 700b) is able to be overcome during a closure stroke of end effector (740) (i.e., the transition of anvil (760) toward a fully closed position) such that anvil (760) is pivotable to a fully closed position. It will be understood that the resistive load provided by springs (700a, 700b) is able to be overcome during a closure stroke of the device, whether that closure stroke is effectuated by the distal translation of a closure ring, such as closure ring (270) described above, the distal translation of a knife member, such as knife member (80) described above, or a combination thereof. As shown in FIG. 41A, during a closure stroke of end effector (740), upper legs (702a, 702b) are compressed downwardly toward lower legs (704a, 704b) as anvil (760) pivots toward lower jaw (750) and into a fully closed position. Springs (700a, 700b) may be configured and positioned such that upper legs (702a, 702b) are substantially parallel relative to bottom surface (753) of lower jaw (750) and lower legs (704a, 704b) are positioned at an acute angle relative to bottom surface (753) of lower jaw (750) when anvil (760) is in a fully closed position. Conversely, as shown in FIG. 41B, during an opening stroke of end effector (740) (i.e., the transition of anvil (760) toward a fully opened position), upper legs (702a, 702b) expand upwardly away from respective lower legs (704a, 704b) as anvil (760) pivots away from lower jaw (750) toward a fully opened position. Springs (700a, 700b) may be configured and positioned such that upper legs (702a, 702b) are positioned at an acute angle relative to bottom surface (753) of lower jaw (750) and lower legs (704a, 704b) are substantially parallel with bottom surface (753) of lower jaw (750) when anvil (760) is in a fully opened position.

In the illustrated embodiment, because springs (700a, 700b) are positioned around pins (766), springs (700a, 700b) translate unitarily with anvil (760) in a distal direction as pins (766) travel along the corresponding openings (754) in sidewalls (751) of lower jaw (750) during a closure stroke of end effector (740). Correspondingly, springs (700a, 700b)

also translate unitarily with anvil (760) in a proximal direction as pins (766) travel along the corresponding openings (754) in sidewalls (751) of lower jaw (750) during an opening stroke of end effector (740).

F. Illustrative Staple Cartridge with Leaf Springs

Figure 42:
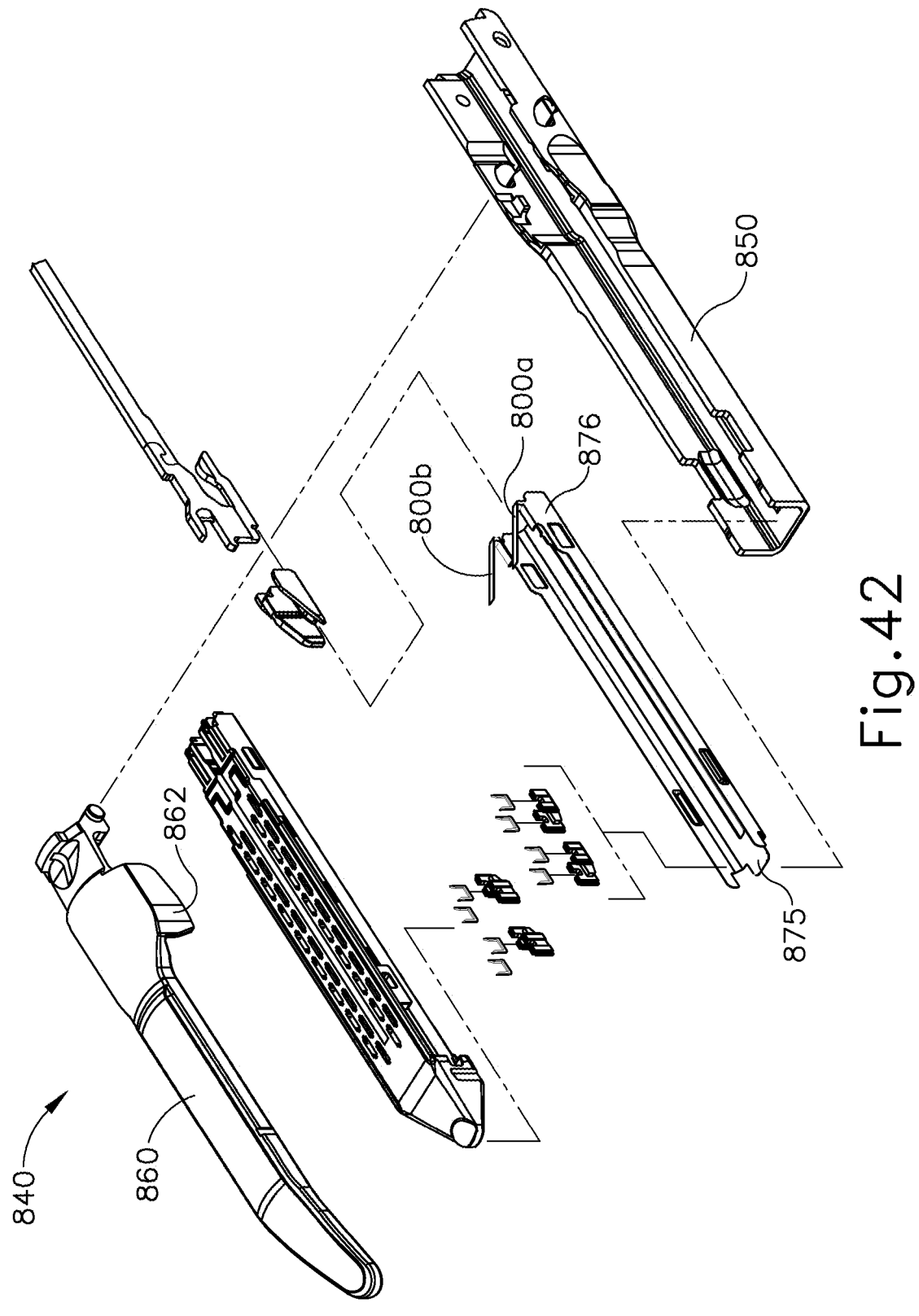
FIG. 42 depicts an exploded perspective view of an illustrative end effector that includes a tray comprising a pair of resilient arms.
Figure 43:
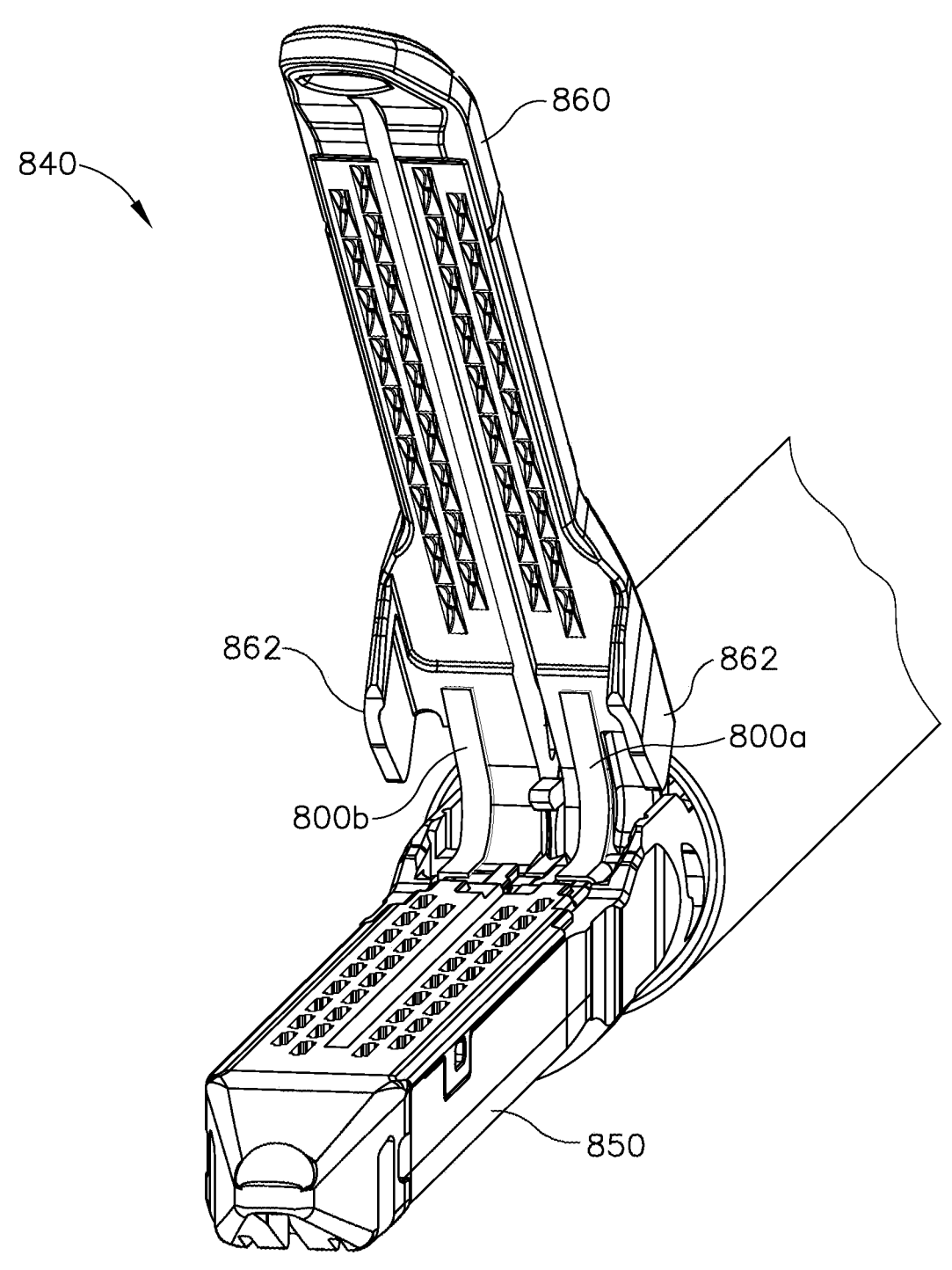
FIG. 43 depicts a perspective view of the end effector of FIG. 42 in an open position.
Figure 44A:
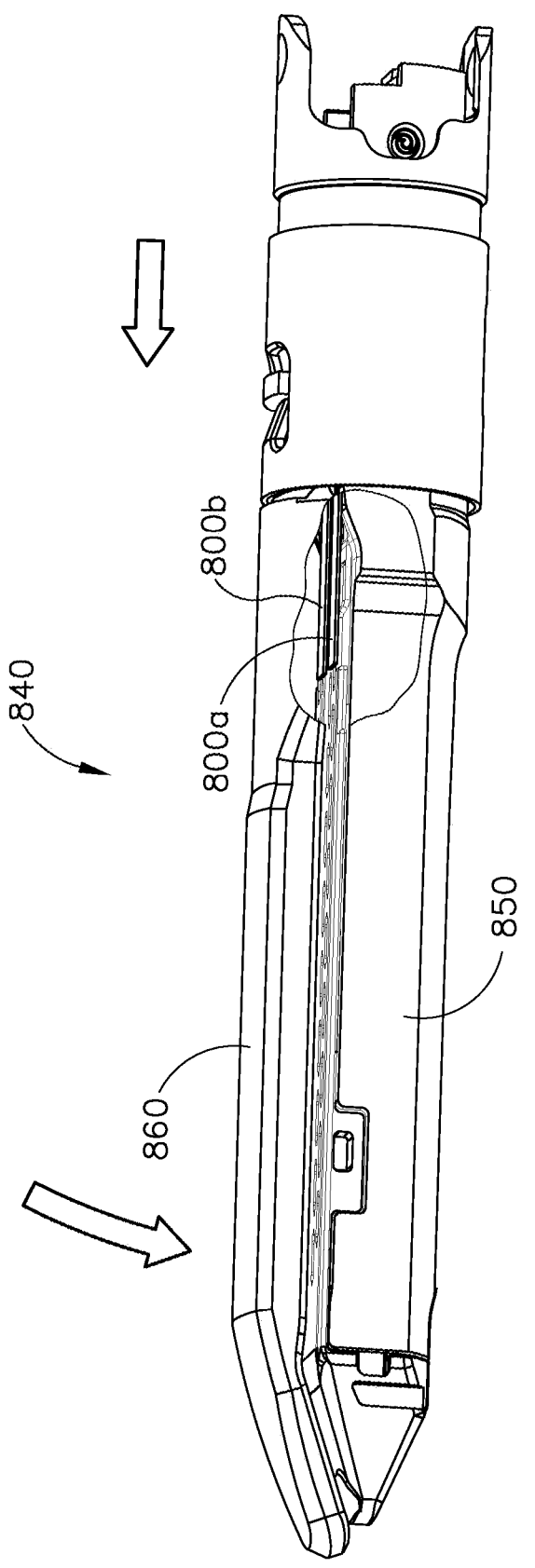
FIG. 44A depicts a perspective view of the end effector of FIG. 42 fully closed with a portion of the end effector removed to reveal the resilient arms and other internal structures.
Figure 44B:
FIG. 44B depicts a perspective view of the end effector of FIG. 42 fully opened with a portion of the end effector removed to reveal the resilient arms and other internal structures.

FIG. 42 depicts an alternate illustrative resilient member comprising a tray (876) comprising a pair or resilient arms (800a, 800b) configured to be used in conjunction with an illustrative end effector, including but not limited to end effector (240) described above. In the illustrated embodiment, tray (876) comprises a pair of resilient arms (800a, 800b) that extend away from tray (876) at an angle. Except for the addition of resilient arms (800a, 800b), tray (876) is substantially similar to tray (76) described above. Resilient arms (800a, 800b) may comprise structures that are integrally formed with tray (876) or structures that structures that are separate from and attached to tray (876). FIGS. 43-44B depict different views of the interaction between resilient arms (800a, 800b), anvil (860), and lower jaw (850), which is substantially similar to lower jaw (50) described above, when anvil (860) is in a closed position and an open position.

FIGS. 42-44B depict end effector (840), which is substantially similar to end effectors (40, 240) described above. Except for the addition of resilient arms (800a, 800b), the components of end effector (840) are substantially similar and function substantially similarly to those of end effectors (40, 240) described above. Accordingly, the description of those previously discussed components of end effector (840) will not be repeated here. Although the illustrated embodiment depicts a pair of resilient arms (800a, 800b), which allows resilient arms (800a, 800b) to provide a biasing force evenly on both sides of anvil (860), it will be appreciated that other embodiments may include any suitable number of resilient arms, including one resilient arm or three or more resilient arms.

In the illustrated embodiment, resilient arms (800a, 800b) are configured as leaf springs positioned at a proximal end of tray (876) and are configured such that resilient arms (800a, 800b) are biased away from tray (876) when resilient arms (800a, 800b) are in an uncompressed state. Resilient arms (800a, 800b) may be configured such that resilient arms (800a, 800b) extend at an acute angle relative to bottom surface (875) of tray (876) when resilient arms (800a, 800b) are in an uncompressed state. As shown, resilient arms (800a, 800b) are positioned relative to anvil (860) such that resilient arms (800a, 800b) engage anvil (860) when end effector (840), including tray (870), is fully assembled. Specifically, each of the resilient arms (800a, 800b) are positioned so that they contact the interior surface (861) of anvil (860). As shown, the interior surface (861) comprises the surface on the underside of anvil (860) that extends between the outer flanges (862) of anvil (860). Accordingly, resilient arms (800a, 800b) apply a force on anvil (860) that biases anvil (860) toward a fully opened position. In alternate embodiments, resilient arms (800a, 800b) could comprise separately formed springs that are attached to tray (876).

Resilient arms (800a, 800b) are configured to provide a resistive load sufficient to bias anvil (860) to remain in a fully opened position when anvil (860) is in a fully opened position thereby reducing undesired movement or "flopping" of anvil (860) when anvil (860) is in a fully opened position. Resilient arms (800a, 800b) may be configured to provide a substantially constant force on anvil (860) that biases anvil (860) toward a fully opened position by remaining in substantially constant contact with anvil (860). In addition, as illustrated by FIG. 44A, the resistive load provided by resilient arms (800a, 800b) is able to be overcome during a closure stroke of end effector (840) (i.e., the transition of anvil (860) toward a fully closed position) such that anvil (860) is pivotable to a fully closed position. It will be understood that the resistive load provided by resilient arms (800a, 800b) is able to be overcome during a closure stroke of the device, whether that closure stroke is effectuated by the distal translation of a closure ring, such as closure ring (270) described above, the distal translation of a knife member, such as knife member (80) described above, or a combination thereof. As shown in FIG. 44A, during a closure stroke of end effector (840), resilient arms (800a, 800b) are compressed downwardly toward tray (876) as anvil (860) pivots toward lower jaw (850) and into a fully closed position. Resilient arms (800a, 800b) may be configured and positioned such that resilient arms (800a, 800b) contact a respective sidewall or other structure of tray (876) and/or are substantially parallel relative to bottom surface (875) of tray (876) when anvil (860) is in a fully closed position. Conversely, as shown in FIG. 44B, during an opening stroke of end effector (840) (i.e., the transition of anvil (860) toward a fully opened position), resilient arms (800a, 800b) expand upwardly away from tray (876) as anvil (860) pivots away from lower jaw (850) toward a fully opened position. Resilient arms (800a, 800b) may be configured and positioned such that resilient arms (800a, 800b) are positioned at an acute angle relative to bottom surface (875) of tray (876) when anvil (860) is in a fully opened position.

IV. Illustrative Alternative End Effector

Figure 45:
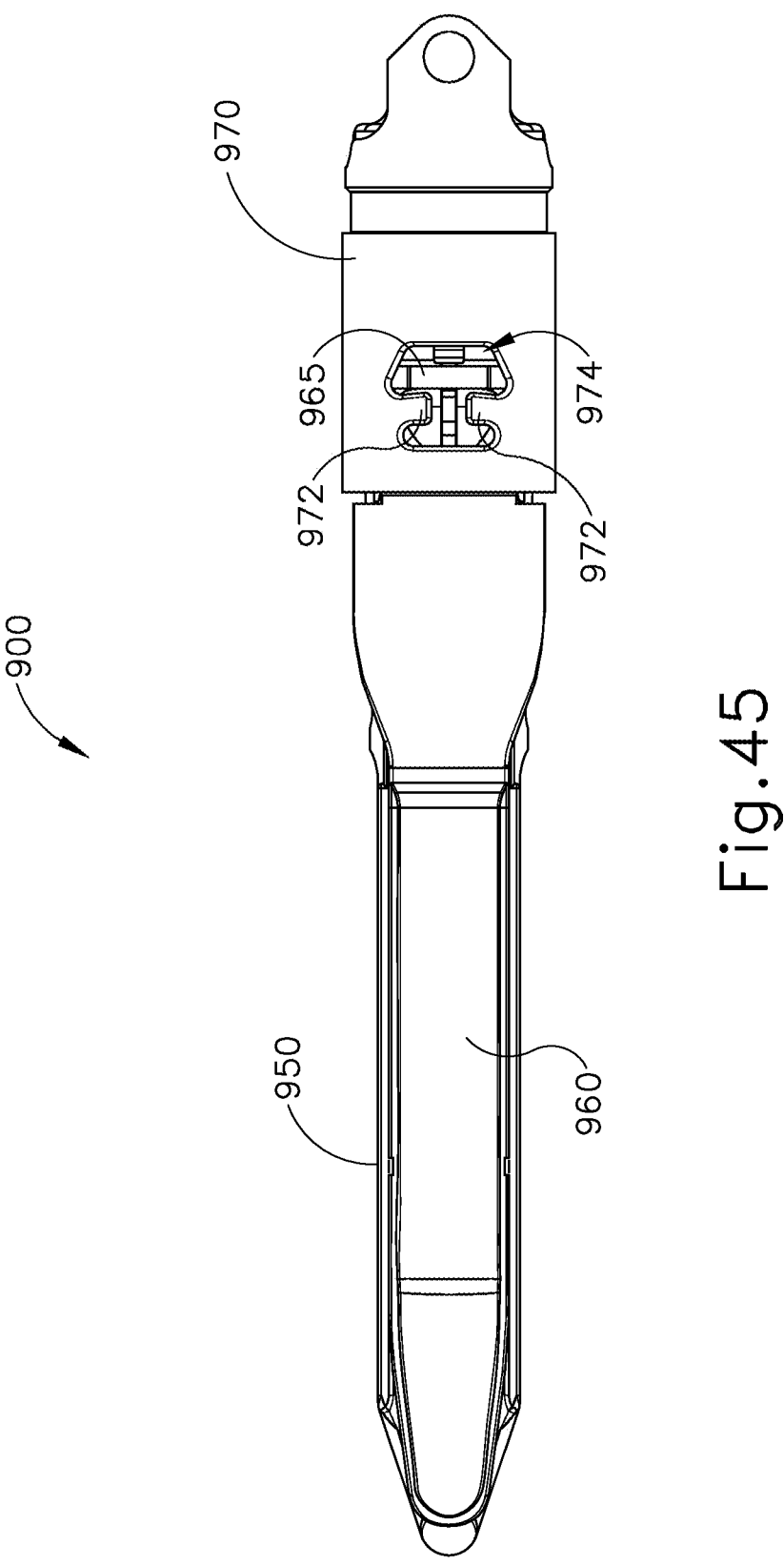
FIG. 45 depicts a top plan view of another illustrative end effector for use with the instrument of FIG. 1.

FIG. 45 depicts another illustrative end effector (900) that may be readily incorporated into surgical stapling and severing instrument (10). End effector (900) is substantially similar to end effectors (40, 240) described above. As a result, the components of end effector (900) are substantially similar and function substantially similarly to those of end effectors (40, 240) described above. Accordingly, the description of those previously discussed components of end effector (900) will not be repeated here. It should be understood that end effector (900) includes an anvil (960) a lower jaw (950), and a closure ring (970). Anvil (960) is identical to anvil (260) described above. Lower jaw (950) is identical to lower jaw (250) described above. Like closure ring (270) described above, closure ring (970) of the present example is operable to advance distally to close anvil (960) toward lower jaw (950); and to retract proximally to open anvil (960) away from lower jaw (950). End effector (900) may be coupled with shaft assembly (30) and may be driven just like end effectors (40, 240) described above.

Figure 46:
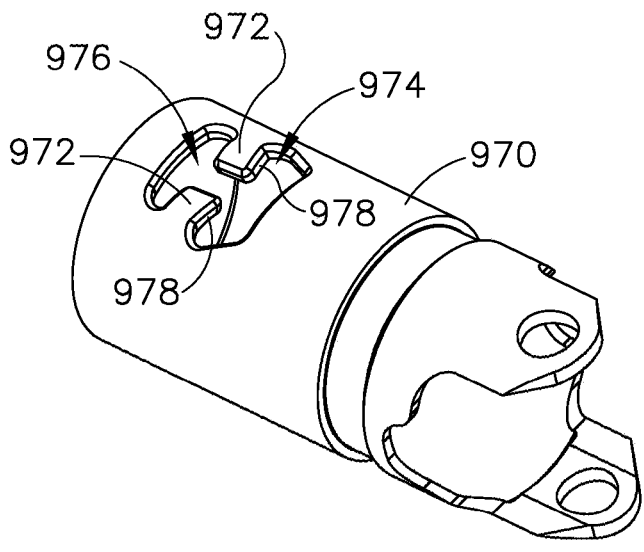
FIG. 46 depicts a perspective view of a closure ring of the end effector of FIG. 45.
Figure 47:
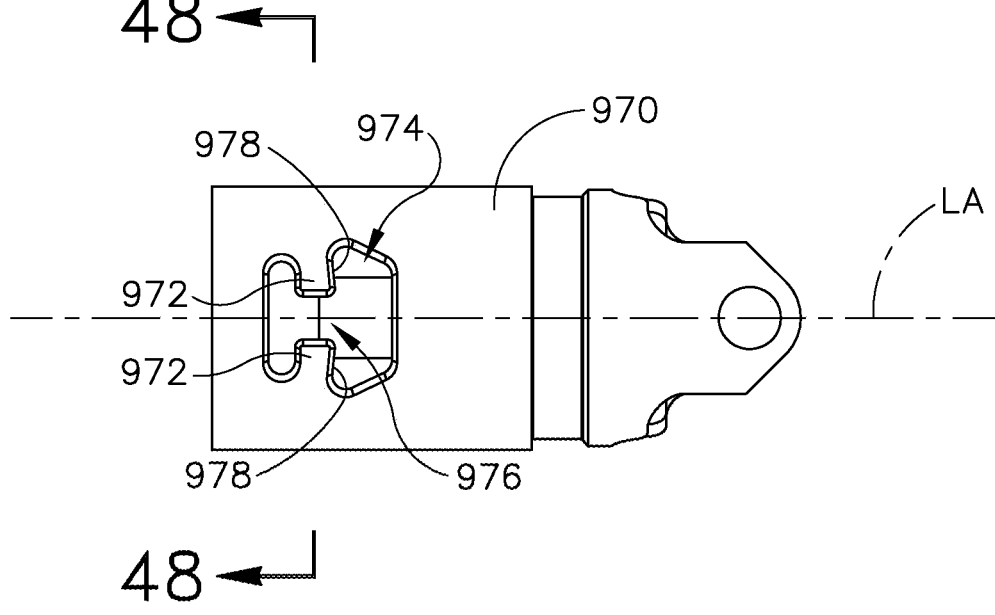
FIG. 47 depicts a top plan view of the closure ring of FIG. 46.
Figure 48:
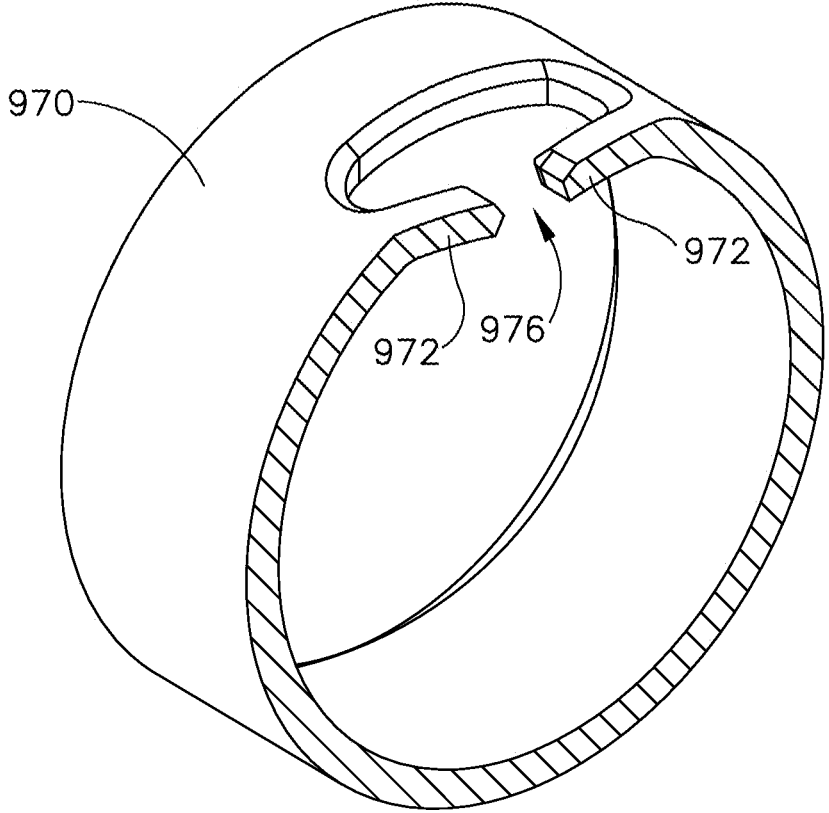
FIG. 48 depicts a cross-sectional view of the closure ring of FIG. 46, taken along line 48-48 of FIG. 47.

As best seen in FIGS. 46-47, closure ring (970) of the present example has a lateral hole or opening (974), similar to the lateral hole or opening (274) of closure ring (270). However, unlike closure ring (270), closure ring (970) has a pair of opposing tabs (972) instead of tab (272). Tabs (927) are oriented toward each other, along a common plane that extends perpendicularly relative to the longitudinal axis (LA) of closure ring (970). The free ends of tabs (927) are separated from each other, such that a gap (976) is defined between tabs (927). In some instances, this gap (976) is sized to accommodate longitudinal movement of knife member (80). In other words, knife member (80) may travel through gap (976) during longitudinal movement of knife member (80) in some versions. As best seen in FIG. 48, tabs (927) are also bent inwardly toward the longitudinal axis (LA) in this example. It should be understood that tabs (927) may function similar to tab (272). In particular, when closure ring (970) is retracted proximally, the proximal surfaces (978) of tabs (927) may engage the distal surface of tab (965) of anvil (960), such that tabs (927) may assist in driving anvil (960) from the closed position to the open position as closure ring (970) is retracted proximally. Tabs (927) may also remain engaged with tab (965) while anvil (960) is in the open position, such that tabs (927, 965) may cooperate to hold anvil (960) in the open position.

In view of the interchangeability of closure ring (270) with closure ring (970), it should be understood that closure ring (970) may be readily used with anvils (360, 460) and inserts (300, 400). Similarly, closure ring (970) may be readily used with anvil (560) having elastomeric layer (500). In addition, tabs (972) may each be modified to include an elastomeric layer similar to the way in which tab (672) of closure ring (670) includes elastomeric layer (600). Furthermore, end effector (900) may be modified to include springs (700a, 700b) like end effector (740). End effector (900) may also receive a staple cartridge that includes a tray with resilient arms, similar to tray (876) described above.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims. By way of example only, end effectors developed in accordance with the teachings herein may incorporate more than one of the various types of resilient members within a single end effector, including but not limited to a single end effector that includes an elastomeric insert or layer of elastomeric material and a pair of springs and/or resilient arms and a single end effector that includes a layer of elastomeric material on both the tab of the anvil and the tab of the closure ring.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the resilient members described above may be used in conjunction with a variety of end effectors. By way of example only, various teachings herein may be readily combined with one or more of the end effectors described in U.S. patent application Ser. No. 13/780,120, entitled "Jaw Closure Feature for End Effector of Surgical Instrument," filed Feb. 28, 2013, issued as U.S. Pat. No. 9,839,421 on Dec. 12, 2017, the disclosure of which was previously incorporated by reference herein above. Other suitable end effectors that can be used in conjunction with the resilient members disclosed herein will be apparent to those of ordinary skill in the art in view of the teachings herein.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/

0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013, the disclosure of which is incorporated by reference herein; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:

(a) a shaft comprising a closure driver configured to translate between a proximal position, an intermediate position, and a distal position, wherein the intermediate position of the closure driver is located between the distal position and the proximal position;

(b) an end effector extending distally from the shaft, wherein the end effector comprises:

(i) a first jaw, and (ii) a second jaw comprising an outwardly extending pin, wherein the first jaw and the second jaw are configured to move relative to each other between an open position and a closed position, wherein the closure driver is configured to translate from the proximal position into the distal position to transition the first jaw and the second jaw from the open position into the closed position;

(c) a jaw opening tab associated with the closure driver, wherein the jaw opening tab is configured to engage the second jaw as the closure driver translates proximally from the intermediate position toward the proximal position to thereby transition the first jaw and the second jaw toward the open position; and (d) a jaw opening biasing spring comprising a helical torsion spring having a coil, wherein the jaw opening biasing spring is configured to bias the first jaw and the second jaw toward the open position, wherein the jaw opening biasing spring is configured to drive the first jaw and the second jaw toward the open position while the closure driver translates from the distal position toward the intermediate position, wherein the coil of the helical torsion spring is positioned around the outwardly extending pin.

2. The surgical instrument of claim 1, wherein the helical torsion spring comprises a first leg engaged with an underside of the second jaw.

3. The surgical instrument of claim 1, wherein the helical torsion spring comprises a second leg engaged with the first jaw.

4. The surgical instrument of claim 1, wherein the jaw opening biasing spring comprises a cantilever spring.

5. The surgical instrument of claim 1, wherein the first jaw and the second jaw a pivotally coupled to each other such that the first jaw and the second jaw are configured to pivot relative to each other between the open position and the closed position.

6. The surgical instrument of claim 5, wherein the first jaw comprises a second tab, wherein the jaw opening tab is configured to engage the second tab of the first jaw as the closure driver actuates proximally from the intermediate position toward the proximal position to thereby transition the first jaw and the second jaw toward the open position.

7. The surgical instrument of claim 6, wherein the closure driver comprises a closure ring.

8. The surgical instrument of claim 7, wherein the closure ring defines an opening, wherein the second tab is housed within the opening defined by the closure ring.

9. The surgical instrument of claim 1, wherein the second jaw comprises an anvil.

10. The surgical instrument of claim 9, wherein the jaw opening biasing spring is interposed between the anvil and the first jaw.

11. The surgical instrument of claim 1, wherein the jaw opening biasing spring is integrated within the first jaw.

12. The surgical instrument of claim 1, wherein the jaw opening biasing spring is positioned at a proximal end of the first jaw.

13. A surgical instrument, comprising:

(a) a shaft comprising a closure driver configured to translate between a proximal position, an intermediate position, and a distal position, wherein the intermediate position of the closure driver is located between the distal position and the proximal position;

(b) an end effector extending distally from the shaft, wherein the end effector comprises:

(i) a first jaw, and (ii) a second jaw, wherein the first jaw and the second jaw are configured to move relative to each other between an open position and a closed position, wherein the closure driver is configured to translate from the proximal position into the distal position to transition the first jaw and the second jaw from the open position into the closed position;

(c) a jaw opening tab associated with the closure driver, wherein the jaw opening tab is configured to engage the second jaw as the closure driver translates proximally from the intermediate position toward the proximal position to thereby transition the first jaw and the second jaw toward the open position; and (d) a jaw opening biasing spring configured to bias the first jaw and the second jaw toward the open position, wherein the jaw opening biasing spring is configured to drive the first jaw and the second jaw toward the open position while the closure driver translates from the distal position toward the intermediate position, wherein the jaw opening biasing spring comprises a leaf spring integrally formed with the first jaw.

14. The surgical instrument of claim 13, wherein the first jaw comprises a tray, wherein the leaf spring is integrally formed with the tray of the first jaw.

15. The surgical instrument of claim 13, wherein the jaw opening biasing spring is positioned at a proximal end of the first jaw.

16. A surgical instrument, comprising:

(a) a shaft comprising a closure driver configured to translate between a proximal position, an intermediate position, and a distal position, wherein the intermediate position of the closure driver is located between the distal position and the proximal position;

(b) an end effector extending distally from the shaft, wherein the end effector comprises:

(i) a cartridge receiving jaw, and (ii) an anvil configured to pivot relative to the cartridge receiving jaw between an open position and a closed position, wherein the closure driver is configured to translate from the proximal position into the distal position to pivot the anvil from the open position into the closed position;

(c) a cam associated with the closure driver, wherein the cam is configured to engage the anvil as the closure driver actuates proximally from the intermediate position toward the proximal position to thereby pivot the anvil toward the open position; and (d) a spring configured to bias the anvil toward the open position, wherein the spring is configured to initially pivot the anvil from the closed position toward the open position while the closure driver translates from the distal position toward the intermediate position, wherein the spring is integrated into the cartridge receiving jaw.

17. The surgical instrument of claim 16, further comprising a handle attached to a proximal end of the shaft.

18. The surgical instrument of claim 17, wherein the shaft comprises a trigger configured to drive translation of the closure driver.

19. The surgical instrument of claim 16, wherein the end effector further comprises a translatable knife.

20. The surgical instrument of claim 16, wherein the spring is positioned at a proximal end of the cartridge receiving jaw.

* * * * *